United States Patent
Ko et al.

(10) Patent No.: US 7,312,222 B2
(45) Date of Patent: Dec. 25, 2007

(54) HETEROCYCLIC PIPERIDINES AS MODULATORS OF CHEMOKINE RECEPTOR ACTIVITY

(75) Inventors: Soo S. Ko, Hockessin, DE (US); George V. Delucca, Wilmington, DE (US); John V. Duncia, Hockessin, DE (US); Joseph B. Santella, III, Springfield, PA (US); Dean A. Wacker, Chadds Ford, PA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 113 days.

(21) Appl. No.: 10/809,772

(22) Filed: Mar. 25, 2004

(65) Prior Publication Data

US 2004/0186097 A1  Sep. 23, 2004

Related U.S. Application Data

(62) Division of application No. 09/465,949, filed on Dec. 17, 1999, now Pat. No. 6,331,545.

(60) Provisional application No. 60/112,714, filed on Dec. 18, 1998.

(51) Int. Cl.
*A61K 31/44* (2006.01)
*C07D 401/12* (2006.01)
*C07D 401/14* (2006.01)

(52) U.S. Cl. ............... 514/255.05; 514/256; 514/307; 514/314; 514/317; 514/318; 514/319; 514/320; 514/321; 514/322; 514/323; 514/324; 514/325; 544/334; 544/405; 546/149; 546/164; 546/180; 546/181; 546/187

(58) Field of Classification Search ............... 544/333, 544/405; 546/149, 164, 180, 181, 187; 514/255.05, 514/256, 307, 314, 317, 318, 319, 320, 321, 514/322, 323, 324, 325
See application file for complete search history.

(56) References Cited

U.S. PATENT DOCUMENTS

| | | | |
|---|---|---|---|
| 2,684,965 A | 7/1954 | Weston et al. | |
| 3,133,061 A | 5/1964 | Kirchner et al. | |
| 4,943,578 A | 7/1990 | Naylor et al. | |
| 5,116,842 A | 5/1992 | Naylor et al. | |
| 5,512,567 A | 4/1996 | Terada et al. | |
| 5,646,151 A | 7/1997 | Kruse et al. | |
| 5,688,955 A | 11/1997 | Kruse et al. | |
| 5,744,458 A | 4/1998 | Kruse et al. | |
| 5,770,735 A * | 6/1998 | Emonds-Alt et al. | ....... 546/191 |
| 6,759,411 B2 * | 7/2004 | Ko et al. | ......... 514/235.5 |

FOREIGN PATENT DOCUMENTS

| | | |
|---|---|---|
| DE | 2013179 | 10/1970 |
| EP | 0747357 | 6/1996 |
| JP | 3163067 | 7/1991 |
| JP | 3163068 | 7/1991 |
| WO | 93/20099 | 10/1993 |
| WO | 95/19344 | 7/1995 |
| WO | 97/17954 | 5/1997 |
| WO | 97/22597 | 6/1997 |
| WO | 97/24324 | 7/1997 |
| WO | 97/48681 | 12/1997 |
| WO | 98/25604 | 6/1998 |
| WO | 98/25617 | 6/1998 |
| WO | 98/27815 | 7/1998 |
| WO | 98/31364 | 7/1998 |
| WO | 99/04794 | 2/1999 |
| WO | 99/09984 | 3/1999 |

OTHER PUBLICATIONS

Khandelwal et al, Agents Acting on CNS, Indian J. Chem. 16B, pp. 1012-1014.
Birch et al., Preparation and Evaluation of Some Hydrophilic Phenylacetl-Piperazines as Peripherally Selective k-Opioid Receptor Agonists, Bioorganic & Medicinal Chemistry Letters, 1992, pp. 1275-1278, vol. 2, No. 10.
Naylor et al., A Potent New Class of k-Receptor Agonist: 4-Substututed 1-(Arylacetyle)-2-[(Dialkylamino)Methyl]Piperazines, J. Med. Chem., 1993, pp. 2075-2083, vol. 36.
Hesselgesser et al., Identification and Characterization of Small Molecule Functional Antagonists of the CCR1 Chemokine Receptor, The Journal of Biological Chemistry, 1998, pp. 15687-15692, vol. 273, No. 25.

* cited by examiner

*Primary Examiner*—Kahsay Habte
(74) *Attorney, Agent, or Firm*—Mary K. VanAtten

(57) ABSTRACT

The present application describes modulators of CCR3 of formula (I):

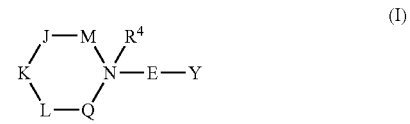

or pharmaceutically acceptable salt forms thereof, useful for the prevention of asthma and other allergic diseases.

43 Claims, No Drawings

HETEROCYCLIC PIPERIDINES AS MODULATORS OF CHEMOKINE RECEPTOR ACTIVITY

CROSS-REFERENCE TO RELATED APPLICATIONS

This application is a divisional of U.S. application Ser. No. 09/981,833 filed Oct. 18, 2001, now U.S. Pat. No. 6,759,411, which is a divisional of U.S. application Ser. No. 09/465,949, filed Dec. 17, 1999, now U.S. Pat. No. 6,331,545, which claims priority to Provisional Application Ser. No. 60/112,714, filed Dec. 18, 1998.

FIELD OF THE INVENTION

This invention relates generally to modulators of chemokine receptor activity, pharmaceutical compositions containing the same, and methods of using the same as agents for treatment and prevention of asthma and allergic diseases, as well as autoimmune pathologies such as rheumatoid arthritis and atherosclerosis.

BACKGROUND OF THE INVENTION

Chemokines are chemotactic cytokines, of molecular weight 6–15 kDa, that are released by a wide variety of cells to attract and activate, among other cell types, macrophages, T and B lymphocytes, eosinophils, basophils and neutrophils (reviewed in Luster, New Eng. J Med., 338, 436–445 (1998) and Rollins, Blood, 90, 909–928 (1997)). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (−1 and −2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a CXXXC chemokine) that do not fall into either of the major chemokine subfamilies.

The chemokines bind to specific cell-surface receptors belonging to the family of G-protein-coupled seven-transmembrane-domain proteins (reviewed in Horuk, Trends Pharm. Sci., 15, 159–165 (1994)) which are termed "chemokine receptors." On binding their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns: CCR-1 (or "CKR-1" or "CC-CKR-1") [MIP-1α, MCP-3, MCP-4, RANTES] (Ben-Barruch, et al., Cell, 72, 415–425 (1993), Luster, New Eng. J. Med., 338, 436–445 (1998)); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo et al., Proc. Natl. Acad. Sci. USA, 91, 2752–2756 (1994), Luster, New Eng. J. Med., 338, 436–445 (1998)); CCR-3 (or "CKR-3" or "CC-CKR-3") [eotaxin-1, eotaxin-2, RANTES, MCP-3, MCP-4] (Combadiere, et al., J. Biol. Chem., 270, 16491–16494 (1995), Luster, New Eng. J. Med., 338, 436–445 (1998)); CCR-4 (or "CKR-4" or "CC-CKR-4") [TARC, MIP-1α, RANTES, MCP-1] (Power et al., J. Biol. Chem., 270, 19495–19500 (1995), Luster, New Eng. J. Med., 338, 436–445 (1998)); CCR-5 (or "CKR-5" OR "CC-CKR-5") [MIP-1α, RANTES, MIP-1β] (Sanson, et al., Biochemistry, 35, 3362–3367 (1996)); CCR-6 (or "CKR-6" or "CC-CKR-6") [LARC] (Baba et al., J. Biol. Chem.", 272, 14893–14898 (1997)); CCR-7 (or "CKR-7" or "CC-CKR-7") [ELC] (Yoshie et al., J. Leukoc. Biol. 62, 634–644 (1997)); CCR-8 (or "CKR-8" or "CC-CKR-8") [I-309, TARC, MIP-1β] (Napolitano et al., J. Immunol., 157, 2759–2763 (1996), Bernardini et al., Eur. J. Immunol., 28, 582–588 (1998)); and CCR-10 (or "CKR-10" or "CC-CKR-10") [MCP-1, MCP-3] (Bonini et al, DNA and Cell Biol., 16, 1249–1256 (1997)).

In addition to the mammalian chemokine receptors, mammalian cytomegaloviruses, herpesviruses and poxviruses have been shown to express, in infected cells, proteins with the binding properties of chemokine receptors (reviewed by Wells and Schwartz, Curr. Opin. Biotech., 8, 741–748 (1997)). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

Chemokine receptors have been implicated as being important mediators of inflammatory, infectious, and immunoregulatory disorders and diseases, including asthma and allergic diseases, as well as autoimmune pathologies such as rheumatoid arthritis and atherosclerosis. For example, the chemokine receptor CCR-3 plays a pivotal role in attracting eosinophils to sites of allergic inflammation and in subsequently activating these cells. The chemokine ligands for CCR-3 induce a rapid increase in intracellular calcium concentration, increased expression of cellular adhesion molecules, cellular degranulation, and the promotion of eosinophil migration. Accordingly, agents which modulate chemokine receptors would be useful in such disorders and diseases. In addition, agents which modulate chemokine receptors would also be useful in infectious diseases by blocking infection of CCR3 expressing cells by HIV or in preventing the manipulation of immune cellular responses by viruses such as cytomegaloviruses.

A substantial body of art has accumulated over the past several decades with respect to substituted piperidines and pyrrolidines. These compounds have implicated in the treatment of a variety of disorders.

WO 98/25604 describes spiro-substituted azacycles which are useful as modulators of chemokine receptors:

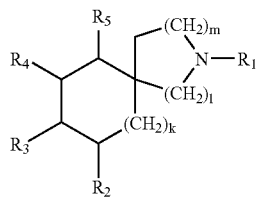

wherein $R_1$ is $C_{1-6}$ alkyl, optionally substituted with functional groups such as —$NR^6CONHR^7$, wherein $R^6$ and $R^7$ may be phenyl further substituted with hydroxy, alkyl, cyano, halo and haloalkyl. Such spiro compounds are not considered part of the present invention.

WO 98/31364 describes disubstituted piperidines which are useful as modulators of chemokine receptors:

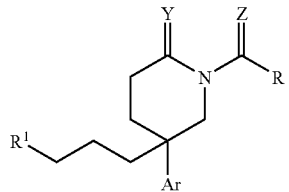

wherein $R^1$ is benzylpiperidine or benzylpyrrolidine. Such disubstituted piperidines ar not considered part of the present invention.

WO 96/26196 is directed to certain benzylpiperidines and piperazines as muscarinic antagonists:

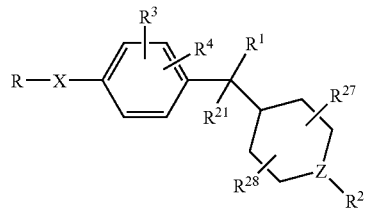

In these compounds as well as other muscarinic antagonists, the ring of $R^2$ is linked directly to the piperidine containing Y and Z. The compounds of the present invention do not include compounds of this type.

WO 95/19344 discloses tachykinin antagonists of formula:

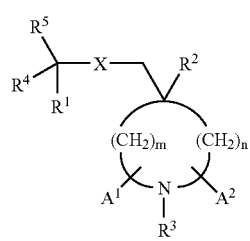

wherein X is O or $NR^{19}$, $R^1$ and $R^2$ are substituted phenyl, and $R^3$ may be $COR^9$, $CONR^{10}R^{11}$ and the like. Such compounds require this substitution at $R^1$, $R^2$, and X while $R^3$ groups do not represent those of the present invention.

Other tachykinin antagonists include those of WO 97/22597, in which the two piperidine or pyrroline rings must be linked directly through a bond:

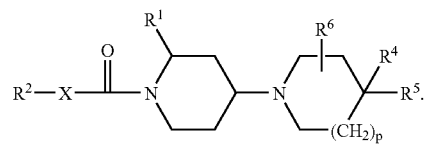

U.S. Pat. No. 5,576,319 discloses a method of treatment for schizophrenia comprising administering a compound of formula:

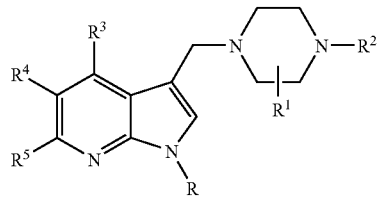

to a patient in need thereof. These compounds are not indicated as modulators of CCR3, and do not contain the necessary features of the present invention.

WO 97/06802 concerns oxido-squalene cyclase inhibitors of formula:

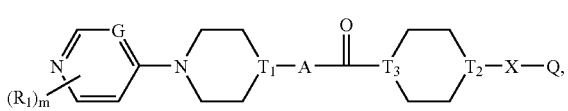

and WO 98/35959 concerns similar heterocyclic derivatives of formula:

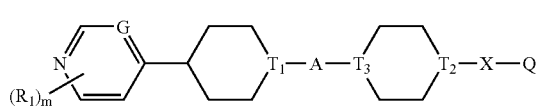

wherein $T_1$, $T_2$, and $T_3$ may be carbon or nitrogen, X may be methylene, Q is a carbocyclic ring, A may be absent and G is N or CH. Such compounds contain pyridine or pyridine derivatives directly off the piperidine rings. Further, the compounds of these references which bridge the pyridine analogously to the present invention require a carbonyl functionality in the linker.

Sulphonamide derivatives are implicated in WO 97/48681 as useful in the treatment of CNS disorders. The nitrogen bearing $R^1$ and $R^2$ of compounds of formula:

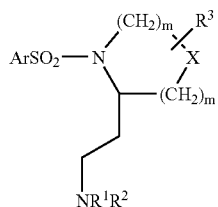

may be taken together to form a piperidine ring, however, such rings may only be substituted when an additional nitrogen is contained in the ring formed by $R^1$ and $R^2$.

The foregoing reference compounds are readily distinguished structurally by either the nature of the terminal functionality, attachment chain, or possible substitution of the present invention. The prior art does not disclose nor suggest the unique combination of structural fragments which embody these novel piperidines and pyrrolidines as having activity toward the chemokine receptors.

SUMMARY OF THE INVENTION

Accordingly, one object of the present invention is to provide novel agonists or antagonists of CCR-3, or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating allergic disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of formula I:

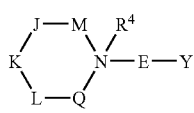
I or stereoisomers or pharmaceutically acceptable salts thereof, wherein M, J, K, L, Q, E, Y, and $R^4$ are defined below are effective modulators of chemokine activity.

DETAILED DESCRIPTION OF PREFERRED EMBODIMENTS

[1] Thus, in a first embodiment, the present invention provides novel compounds of formula I:

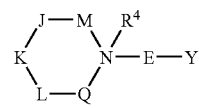
I or stereoisomers or pharmaceutically acceptable salts thereof, wherein:

M is absent or selected from $CH_2$, $CHR^5$, $CHR^{13}$, $CR^{13}R^{13}$, and $CR^5R^{13}$;

Q is selected from $CH_2$, $CHR^5$, $CHR^{13}$, $CR^{13}R^{13}$, and $CR^5R^{13}$;

J, K, and L are independently selected from $CH_2$, $CHR^5$, $CHR^6$, $CR^6R^6$ and $CR^5R^6$;

with the provisos:
1) at least one of M, J, K, L, or Q contains an $R^5$; and
2) when M is absent, J is selected from $CH_2$, $CHR^5$, $CHR^{13}$, and $CR^5R^{13}$;

E is $-(CR^7R^8)-(CR^9R^{10})_v-$;

Y is selected from:

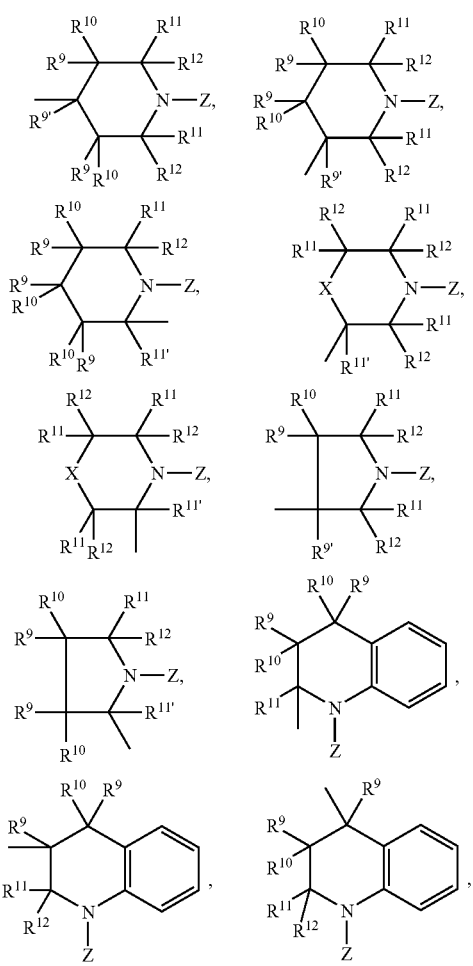

-continued

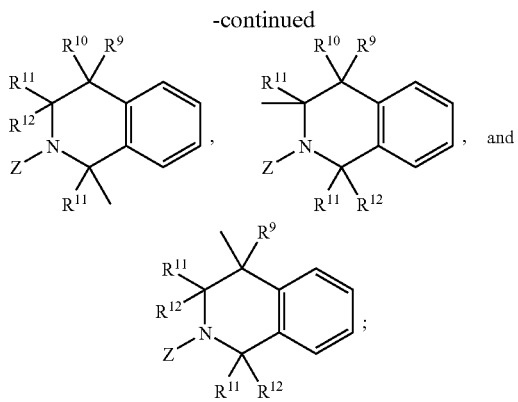

X is selected from NR$^{14}$, O, and S;

Z is selected from C(O)R$^3$, S(O)$_2$R$^3$, C(O)OR$^3$, C(O)NR$^2$R$^3$, C(=NR$^1$)NR$^2$R$^3$, C(=CHCN)NR$^2$R$^3$, C(=CHNO$_2$)NR$^2$R$^3$, C(=C(CN)$_2$)NR$^2$R$^3$, and (CR'R')$_r$-phenyl substituted with 0–5 R$^{15}$;

R', at each occurrence, is selected from H, C$_{1-6}$ alkyl, C$_{2-8}$ alkenyl, C$_{2-8}$ alkynyl, (CH$_2$)$_r$C$_{3-6}$ cycloalkyl, and (CH$_2$)$_r$ phenyl substituted with R$^{15e}$;

R$^1$ is selected from H, C$_{1-6}$ alkyl, C$_{3-6}$ cycloalkyl, OH, CN, and (CH$_2$)$_w$phenyl;

R$^2$ is selected from H, C$_{1-8}$ alkyl, C$_{2-8}$ alkenyl, C$_{2-8}$ alkynyl, (CH$_2$)$_r$C$_{3-6}$ cycloalkyl, and a (CH$_2$)$_r$—C$_{3-10}$ carbocyclic residue substituted with 0–5 R$^{2a}$;

R$^{2a}$, at each occurrence, is selected from C$_{1-4}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{2b}$R$^{2b}$, (CH$_2$)$_r$OH, (CH$_2$)$_r$OR$^{2c}$, (CH$_2$)$_r$SH, (CH$_2$)$_r$SR$^{2c}$, (CH$_2$)$_r$C(O)R$^{2b}$, (CH$_2$)$_r$C(O)NR$^{2b}$R$^{2b}$, (CH$_2$)$_r$NR$^{2b}$C(O)R$^{2b}$, (CH$_2$)$_r$C(O)OR$^{2b}$, (CH$_2$)$_r$OC(O)R$^{2c}$, (CH$_2$)$_r$CH(=NR$^{2b}$)NR$^{2b}$R$^{2b}$, (CH$_2$)$_r$NHC(=NR$^{2b}$)NR$^{2b}$R$^{2b}$, (CH$_2$)$_r$S(O)$_p$R$^{2c}$, (CH$_2$)$_r$S(O)$_2$NR$^{2b}$R$^{2b}$, (CH$_2$)$_r$NR$^{2b}$S(O)$_2$R$^{2c}$, and (CH$_2$)$_r$phenyl;

R$^{2b}$, at each occurrence, is selected from H, C$_{1-6}$ alkyl, C$_{3-6}$ cycloalkyl, and phenyl;

R$^{2c}$, at each occurrence, is selected from C$_{1-5}$ alkyl, C$_{3-6}$ cycloalkyl, and phenyl;

R$^3$ is selected from a CR$^{3'}$R$^{3''}$R$^{3'''}$, (CR$^{3'}$R$^{3''}$)$_r$—C$_{3-10}$ carbocyclic residue substituted with 0–5 R$^{15}$ and a (CR$^{3'}$R$^{3''}$)$_r$-5–10 membered heterocyclic system containing 1–4 heteroatoms selected from N, O, and S, substituted with 0–3 R$^{15}$;

R$^{3'}$ and R$^{3''}$, at each occurrence, are selected from H, C$_{1-6}$ alkyl, (CH$_2$)$_r$C$_{3-6}$ cycloalkyl, and phenyl;

R$^4$ is absent, taken with the nitrogen to which it is attached to form an N-oxide, or selected from C$_{1-8}$ alkyl, C$_{2-8}$ alkenyl, C$_{2-8}$ alkynyl, (CH$_2$)$_r$C$_{3-6}$ cycloalkyl, (CH$_2$)$_q$C(O)R$^{4b}$, (CH$_2$)$_q$C(O)NR$^{4a}$R$^{4a'}$, (CH$_2$)$_q$C(O)OR$^{4b}$, and a (CH$_2$)$_r$—C$_{3-10}$ carbocyclic residue substituted with 0–3 R$^{4c}$;

R$^{4a}$ and R$^{4a'}$, at each occurrence, are selected from H, C$_{1-6}$ alkyl, (CH$_2$)$_r$C$_{3-6}$ cycloalkyl, and phenyl;

R$^{4b}$, at each occurrence, is selected from C$_{1-6}$ alkyl, C$_{2-8}$ alkenyl, (CH$_2$)$_r$C$_{3-6}$ cycloalkyl, C$_{2-8}$ alkynyl, and phenyl;

R$^{4c}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, (CH$_2$)$_r$OH, (CH$_2$)$_r$SC$_{1-5}$ alkyl, (CH$_2$)$_r$NR$^{4a}$R$^{4a'}$, and (CH$_2$)$_r$phenyl;

R$^5$ is selected from a (CR$^{5'}$R$^{5''}$)$_t$—C$_{3-10}$ carbocyclic residue substituted with 0–5 R$^{16}$ and a (CR$^{5'}$R$^{5''}$)$_t$-5–10 membered heterocyclic system containing 1–4 heteroatoms selected from N, O, and S, substituted with 0–3 R$^{16}$;

R$^{5'}$ and R$^{5''}$, at each occurrence, are selected from H, C$_{1-6}$ alkyl, (CH$_2$)$_r$C$_{3-6}$ cycloalkyl, and phenyl;

R$^6$, at each occurrence, is selected from C$_{1-4}$ alkyl, C$_{2-8}$ alkenyl, C$_{2-8}$ alkynyl, (CH$_2$)$_r$C$_{3-6}$ cycloalkyl, (CF$_2$)$_r$CF$_3$, CN, (CH$_2$)$_r$NR$^{6a}$R$^{6a'}$, (CH$_2$)$_r$OH, (CH$_2$)$_r$OR$^{6b}$, SH, (CH$_2$)$_r$SR$^{6b}$, (CH$_2$)$_r$C(O)OH, (CH$_2$)$_r$C(O)R$^{6b}$, (CH$_2$)$_r$C(O)NR$^{6a}$R$^{6a'}$, (CH$_2$)$_r$NR$^{6d}$C(O)R$^{6a}$, (CH$_2$)$_r$C(O)OR$^{6b}$, (CH$_2$)$_r$OC(O)R$^{6b}$, (CH$_2$)$_r$S(O)$_p$R$^{6b}$, (CH$_2$)$_r$S(O)$_2$NR$^{6a}$R$^{6a'}$, (CH$_2$)$_r$NR$^{6d}$S(O)$_2$R$^{6b}$, and (CH$_2$)$_r$phenyl substituted with 0–3 R$^{6c}$;

R$^{6a}$ and R$^{6a'}$, at each occurrence, are selected from H, C$_{1-6}$ alkyl, C$_{3-6}$ cycloalkyl, and phenyl substituted with 0–3 R$^{6c}$;

R$^{6b}$, at each occurrence, is selected from C$_{1-6}$ alkyl, C$_{3-6}$ cycloalkyl, and phenyl substituted with 0–3 R$^{6c}$;

R$^{6c}$, at each occurrence, is selected from C$_{1-6}$ alkyl, C$_{3-6}$ cycloalkyl, Cl, F, Br, I, CN, NO$_2$, (CF$_2$)$_r$CF$_3$, (CH$_2$)$_r$OC$_{1-5}$ alkyl, (CH$_2$)$_r$OH, (CH$_2$)$_r$SC$_{1-5}$ alkyl, and (CH$_2$)$_r$NR$^{6a}$R$^{6d}$;

R$^{6d}$, at each occurrence, is selected from H, C$_{1-6}$ alkyl, and C$_{3-6}$ cycloalkyl;

R$^7$ is selected from H, C$_{1-8}$ alkyl, C$_{2-8}$ alkenyl, C$_{2-8}$ alkynyl, (CH$_2$)$_q$OH, (CH$_2$)$_q$SH, (CH$_2$)$_q$OR$^{7d}$, (CH$_2$)$_q$SR$^{7d}$, (CH$_2$)$_q$NR$^{7a}$R$^{7a'}$, (CH$_2$)$_r$C(O)OH, (CH$_2$)$_r$C(O)R$^{7b}$, (CH$_2$)$_r$C(O)NR$^{7a}$R$^{7a'}$, (CH$_2$)$_q$NR$^{7a}$C(O)R$^{7a}$, (CH$_2$)$_r$C(O)OR$^{7b}$, (CH$_2$)$_q$OC(O)R$^{7b}$, (CH$_2$)$_q$S(O)$_p$R$^{7b}$, (CH$_2$)$_q$S(O)$_2$NR$^{7a}$R$^{7a'}$, (CH$_2$)$_q$NR$^{7a}$S(O)$_2$R$^{7b}$, C$_{1-6}$ haloalkyl, a (CH$_2$)$_r$—C$_{3-10}$ carbocyclic residue substituted with 0–3 R$^{7c}$, and a (CH$_2$)$_r$-5–10 membered heterocyclic system containing 1–4 heteroatoms selected from N, O, and S, substituted with 0–2 R$^{7c}$;

R$^{7a}$ and R$^{7a'}$, at each occurrence, are selected from H, C$_{1-6}$ alkyl, C$_{2-8}$ alkenyl, C$_{2-8}$ alkynyl, (CH$_2$)$_r$C$_{3-6}$ cycloalkyl, a (CH$_2$)$_r$—C$_{3-10}$ carbocyclic residue substituted with 0–5 R$^{7e}$, and a (CH$_2$)$_r$-5–10 membered heterocyclic system containing 1–4 heteroatoms selected from N, O, and S, substituted with 0–3 R$^{7e}$;

R$^{7b}$, at each occurrence, is selected from C$_{1-6}$ alkyl, C$_{2-8}$ alkenyl, C$_{2-8}$ alkynyl, a (CH$_2$)$_r$—C$_{3-6}$ carbocyclic residue substituted with 0–2 R$^{7e}$, and a (CH$_2$)$_r$-5–6 membered heterocyclic system containing 1–4 heteroatoms selected from N, O, and S, substituted with 0–3 R$^{7e}$;

R$^{7c}$, at each occurrence, is selected from C$_{1-4}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{7f}$R$^{7f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{7b}$, (CH$_2$)$_r$C(O)NR$^{7f}$R$^{7f}$, (CH$_2$)$_r$NR$^{7f}$C(O)R$^{7a}$, (CH$_2$)$_r$C(O)OC$_{1-4}$ alkyl, (CH$_2$)$_r$OC(O)R$^{7b}$, (CH$_2$)$_r$C(=NR$^{7f}$)NR$^{7f}$R$^{7f}$, (CH$_2$)$_r$S(O)$_p$R$^{7b}$, (CH$_2$)$_r$NHC(=NR$^{7f}$)NR$^{7f}$R$^{7f}$, (CH$_2$)$_r$S(O)$_2$NR$^{7f}$R$^{7f}$, (CH$_2$)$_r$NR$^{7f}$S(O)$_2$R$^{7b}$, and (CH$_2$)$_r$phenyl substituted with 0–3 R$^{7e}$;

R$^{7d}$, at each occurrence, is selected from C$_{1-6}$ alkyl substituted with 0–3 R$^{7e}$, alkenyl, alkynyl, and a C$_{3-10}$ carbocyclic residue substituted with 0–3 R$^{7c}$;

R$^{7e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{7f}$R$^{7f}$, and (CH$_2$)$_r$phenyl;

R$^{7f}$, at each occurrence, is selected from H, C$_{1-5}$ alkyl, and C$_{3-6}$ cycloalkyl;

R$^8$ is selected from H, C$_{1-6}$ alkyl, C$_{3-6}$ cycloalkyl, and (CH$_2$)$_r$phenyl substituted with 0–3 R$^{8a}$;

R$^{8a}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{7f}$R$^{7f}$, and (CH$_2$)$_r$phenyl;

alternatively, R$^7$ and R$^8$ join to form C$_{3-7}$ cycloalkyl, or =NR$^{8b}$;

R$^{8b}$ is selected from H, C$_{1-6}$ alkyl, C$_{3-6}$ cycloalkyl, OH, CN, and (CH$_2$)$_r$-phenyl;

R$^9$ is independently selected from H, C$_{1-8}$ alkyl, C$_{2-8}$ alkenyl, C$_{2-8}$ alkynyl, F, Cl, Br, I, NO$_2$, CN, (CH$_2$)$_r$OH, (CH$_2$)$_r$SH, (CH$_2$)$_r$OR$^{9d}$, (CH$_2$)$_r$SR$^{9d}$, (CH$_2$)$_r$NR$^{9a}$R$^{9a'}$, (CH$_2$)$_r$C(O)OH, (CH$_2$)$_r$C(O)R$^{9b}$, (CH$_2$)$_r$C(O)NR$^{9a}$R$^{9a'}$, (CH$_2$)$_r$NR$^{9a}$C(O)R$^{9a}$, (CH$_2$)$_r$NR$^{9a}$C(O)H, (CH$_2$)$_r$C(O)OR$^{9b}$, (CH$_2$)$_r$OC(O)R$^{9b}$, (CH$_2$)$_r$S(O)$_p$R$^{9b}$, (CH$_2$)$_r$S(O)$_2$NR$^{9a}$R$^{9a'}$, (CH$_2$)$_r$NR$^{9a}$S(O)$_2$R$^{9b}$, C$_{1-6}$ haloalkyl, a (CH$_2$)$_r$—C$_{3-10}$ carbocyclic residue substituted with 0–5 R$^{9c}$, and a (CH$_2$)$_r$-5–10 membered heterocyclic system containing 1–4 heteroatoms selected from N, O, and S, substituted with 0–3 R$^{9c}$;

R$^{9'}$ is independently selected from H, C$_{1-8}$ alkyl, C$_{2-8}$ alkenyl, C$_{2-8}$ alkynyl, F, Cl, Br, I, NO$_2$, CN, (CH$_2$)$_r$OH, (CH$_2$)$_r$SH, (CH$_2$)$_r$OR$^{9d}$, (CH$_2$)$_r$SR$^{9d}$, (CH$_2$)$_r$NR$^{9a}$R$^{9a'}$, (CH$_2$)$_r$C(O)OH, (CH$_2$)$_r$C(O)R$^{9b}$, (CH$_2$)$_r$C(O)NR$^{9a}$R$^{9a'}$, (CH$_2$)$_r$NR$^{9a}$C(O)R$^{9a}$, (CH$_2$)$_r$NR$^{9a}$C(O)H, (CH$_2$)$_r$C(O)OR$^{9b}$, (CH$_2$)$_r$OC(O)R$^{9b}$, (CH$_2$)$_r$S(O)$_p$R$^{9b}$, (CH$_2$)$_r$S(O)$_2$NR$^{9a}$R$^{9a'}$, (CH$_2$)$_r$NR$^{9a}$S(O)$_2$R$^{9b}$, C$_{1-6}$ haloalkyl, (CH$_2$)$_r$—C$_{3-6}$ cycloalkyl, (CH$_2$)$_q$-phenyl substituted with 0–5 R$^{9c}$, and a (CH$_2$)$_q$-5–10 membered heterocyclic system containing 1–4 heteroatoms selected from N, O, and S, substituted with 0–3 R$^{9c}$;

R$^{9a}$ and R$^{9a'}$, at each occurrence, are selected from H, C$_{1-6}$ alkyl, C$_{2-8}$ alkenyl, C$_{2-8}$ alkynyl, a (CH$_2$)$_r$—C$_{3-10}$ carbocyclic residue substituted with 0–5 R$^{9e}$, and a (CH$_2$)$_r$-5–10 membered heterocyclic system containing 1–4 heteroatoms selected from N, O, and S, substituted with 0–3 R$^{9e}$;

R$^{9b}$, at each occurrence, is selected from C$_{1-6}$ alkyl, C$_{2-8}$ alkenyl, C$_{2-8}$ alkynyl, a (CH$_2$)$_r$—C$_{3-6}$ carbocyclic residue substituted with 0–2 R$^{9e}$, and a (CH$_2$)$_r$-5–6 membered heterocyclic system containing 1–4 heteroatoms selected from N, O, and S, substituted with 0–3 R$^{9e}$;

R$^{9c}$, at each occurrence, is selected from C$_{1-4}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{9f}$R$^{9f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{9b}$, (CH$_2$)$_r$C(O)NR$^{9f}$R$^{9f}$, (CH$_2$)$_r$NR$^{9f}$C(O)R$^{9a}$, (CH$_2$)$_r$C(O)OC$_{1-4}$ alkyl, (CH$_2$)$_r$OC(O)R$^{9b}$, (CH$_2$)$_r$C(=NR$^{9f}$)NR$^{9f}$R$^{9f}$, (CH$_2$)$_r$S(O)$_p$R$^{9b}$, (CH$_2$)$_r$NHC(=NR$^{9f}$)NR$^{9f}$R$^{9f}$, (CH$_2$)$_r$S(O)$_2$NR$^{9f}$R$^{9f}$, (CH$_2$)$_r$NR$^{9f}$S(O)$_2$R$^{9b}$, and (CH$_2$)$_r$phenyl substituted with 0–3 R$^{9e}$;

R$^{9d}$, at each occurrence, is selected from C$_{1-6}$ alkyl, C$_{2-6}$ alkenyl, C$_{2-6}$ alkynyl, a C$_{3-10}$ carbocyclic residue substituted with 0–3 R$^{9c}$, and a 5–6 membered heterocyclic system containing 1–4 heteroatoms selected from the group consisting of N, O, and S substituted with 0–3 R$^{9c}$;

R$^{9e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{9f}$R$^{9f}$, and (CH$_2$)$_r$phenyl;

R$^{9f}$, at each occurrence, is selected from H, C$_{1-5}$ alkyl, and C$_{3-6}$ cycloalkyl;

R$^{10}$ is independently selected from H, C$_{1-8}$ alkyl, C$_{2-8}$ alkenyl, C$_{2-8}$ alkynyl, F, Cl, Br, I, NO$_2$, CN, (CH$_2$)$_r$OH, (CH$_2$)$_r$OR$^{10d}$, (CH$_2$)$_r$SR$^{10d}$, (CH$_2$)$_r$NR$^{10a}$R$^{10a'}$, (CH$_2$)$_r$C(O)OH, (CH$_2$)$_r$C(O)R$^{10b}$, (CH$_2$)$_r$C(O)NR$^{10a}$R$^{10a'}$, (CH$_2$)$_r$NR$^{10a}$C(O)R$^{10a}$, (CH$_2$)$_r$NR$^{10a}$C(O)H, (CH$_2$)$_r$C(O)OR$^{10b}$, (CH$_2$)$_r$OC(O)R$^{10b}$, (CH$_2$)$_r$S(O)$_p$R$^{10b}$, (CH$_2$)$_r$S(O)$_2$NR$^{10a}$R$^{10a'}$, (CH$_2$)$_r$NR$^{10a}$S(O)$_2$R$^{10b}$, C$_{1-6}$ haloalkyl, a (CH$_2$)$_r$—C$_{3-10}$ carbocyclic residue substituted with 0–5 R$^{10c}$, and a (CH$_2$)$_r$-5–10 membered heterocyclic system containing 1–4 heteroatoms selected from N, O, and S, substituted with 0–3 R$^{10c}$;

R$^{10a}$ and R$^{10a'}$, at each occurrence, are selected from H, C$_{1-6}$ alkyl, C$_{2-8}$ alkenyl, C$_{2-8}$ alkynyl, a (CH$_2$)$_r$—C$_{3-10}$ carbocyclic residue substituted with 0–5 R$^{10e}$, and a (CH$_2$)$_r$-5–10 membered heterocyclic system containing 1–4 heteroatoms selected from N, O, and S, substituted with 0–3 R$^{10e}$;

R$^{10b}$, at each occurrence, is selected from C$_{1-6}$ alkyl, C$_{2-8}$ alkenyl, C$_{2-8}$ alkynyl, a (CH$_2$)$_r$—C$_{3-6}$ carbocyclic residue substituted with 0–2 R$^{10e}$, and a (CH$_2$)$_r$-5–6 membered heterocyclic system containing 1–4 heteroatoms selected from N, O, and S, substituted with 0–3 R$^{10e}$;

R$^{10c}$, at each occurrence, is selected from C$_{1-4}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{10f}$R$^{10f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{10b}$, (CH$_2$)$_r$C(O)NR$^{10f}$R$^{10f}$, (CH$_2$)$_r$NR$^{10f}$C(O)R$^{10a}$, (CH$_2$)$_r$C(O)OC$_{1-4}$ alkyl, (CH$_2$)$_r$OC(O)R$^{10b}$, (CH$_2$)$_r$C(=NR$^{10f}$)NR$^{10f}$R$^{10f}$, (CH$_2$)$_r$S(O)$_p$R$^{10b}$, (CH$_2$)$_r$NHC(=NR$^{10f}$)NR$^{10f}$R$^{10f}$, (CH$_2$)$_r$S(O)$_2$NR$^{10f}$R$^{10f}$, (CH$_2$)$_r$NR$^{10f}$S(O)$_2$R$^{10b}$, and (CH$_2$)$_r$phenyl substituted with 0–3 R$^{10e}$;

R$^{10d}$, at each occurrence, is selected from C$_{1-6}$ alkyl, C$_{2-6}$ alkenyl, C$_{2-6}$ alkynyl, a C$_{3-10}$ carbocyclic residue substituted with 0–3 R$^{10c}$, and a 5–6 membered heterocyclic system containing 1–4 heteroatoms selected from the group consisting of N, O, and S substituted with 0–3 R$^{10c}$;

R$^{10e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{10f}$R$^{10f}$, and (CH$_2$)$_r$phenyl;

R$^{10f}$, at each occurrence, is selected from H, C$_{1-5}$ alkyl, and C$_{3-6}$ cycloalkyl;

with the proviso that when R$^{10}$ is —OH, R$^9$ is not halogen, cyano, or bonded to the carbon to which it is attached through a heteroatom; alternatively, R$^9$ and R$^{10}$ join to form C$_{3-7}$ cycloalkyl;

R$^{11}$ is selected from H, C$_{1-8}$ alkyl, C$_{2-8}$ alkenyl, C$_{2-8}$ alkynyl, (CH$_2$)$_q$OH, (CH$_2$)$_q$SH, (CH$_2$)$_q$OR$^{11d}$, (CH$_2$)$_q$SR$^{11d}$, (CH$_2$)$_q$NR$^{11a}$R$^{11a'}$, (CH$_2$)$_r$C(O)OH, (CH$_2$)$_r$C(O)R$^{11b}$, (CH$_2$)$_r$C(O)NR$^{11a}$R$^{11a'}$, (CH$_2$)$_q$NR$^{11a}$C(O)R$^{11a}$, (CH$_2$)$_r$C(O)OR$^{11b}$, (CH$_2$)$_q$OC(O)R$^{11b}$, (CH$_2$)$_q$S(O)$_p$R$^{11b}$, (CH$_2$)$_q$S(O)$_2$NR$^{11a}$R$^{11a'}$, (CH$_2$)$_q$NR$^{11a}$S(O)$_2$R$^{11b}$, C$_{1-6}$ haloalkyl, a (CH$_2$)$_r$—C$_{3-10}$ carbocyclic residue substituted with 0–5 R$^{11c}$, and a (CH$_2$)$_r$-5–10 membered heterocyclic system containing 1–4 heteroatoms selected from N, O, and S, substituted with 0–3 R$^{11c}$;

R$^{11'}$ is selected from H, C$_{1-8}$ alkyl, C$_{2-8}$ alkenyl, C$_{2-8}$ alkynyl, (CH$_2$)$_q$OH, (CH$_2$)$_q$SH, (CH$_2$)$_q$OR$^{11d}$, (CH$_2$)$_q$SR$^{11d}$, (CH$_2$)$_q$NR$^{11a}$R$^{11a'}$, (CH$_2$)$_r$C(O)OH, (CH$_2$)$_r$C(O)R$^{11b}$, (CH$_2$)$_r$C(O)NR$^{11a}$R$^{11a'}$, (CH$_2$)$_q$NR$^{11a}$C(O)R$^{11a}$, (CH$_2$)$_r$C(O)OR$^{11b}$, (CH$_2$)$_q$OC(O)R$^{11b}$, (CH$_2$)$_q$S(O)$_p$R$^{11b}$, (CH$_2$)$_q$S(O)$_2$NR$^{11a}$R$^{11a'}$, (CH$_2$)$_q$NR$^{11a}$S(O)$_2$R$^{11b}$, C$_{1-6}$ haloalkyl, a (CH$_2$)$_r$—C$_{3-6}$ cycloalkyl, (CH$_2$)$_q$-phenyl substituted with 0–5 R$^{11c}$, and a (CH$_2$)$_q$-5–10 membered heterocyclic system containing 1–4 heteroatoms selected from N, O, and S, substituted with 0–3 R$^{11c}$;

R$^{11a}$ and R$^{11a'}$, at each occurrence, are selected from H, C$_{1-6}$ alkyl, C$_{2-8}$ alkenyl, C$_{2-8}$ alkynyl, a (CH$_2$)$_r$—C$_{3-10}$ carbocyclic residue substituted with 0–5 R$^{11e}$, and a (CH$_2$)$_r$-5–10 membered heterocyclic system containing 1–4 heteroatoms selected from N, O, and S, substituted with 0–3 R$^{11e}$;

R$^{11b}$, at each occurrence, is selected from C$_{1-6}$ alkyl, C$_{2-8}$ alkenyl, C$_{2-8}$ alkynyl, a (CH$_2$)$_r$—C$_{3-6}$ carbocyclic residue substituted with 0–2 $R^{11e}$, and a $(CH_2)_r$-5–6 membered heterocyclic system containing 1–4 heteroatoms selected from N, O, and S, substituted with 0–3 $R^{11e}$;

$R^{11c}$, at each occurrence, is selected from $C_{1-4}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{11f}R^{11f}$, $(CH_2)_rOH$, $(CH_2)_r$ $OC_{1-4}$ alkyl, $(CH_2)_rSC_{1-4}$ alkyl, $(CH_2)_rC(O)OH$, $(CH_2)_rC(O)R^{11b}$, $(CH_2)_rC(O)NR^{11f}R^{11f}$, $(CH_2)_rNR^{11f}C(O)R^{11a}$, $(CH_2)_rC(O)OC_{1-4}$ alkyl, $(CH_2)_rOC(O)R^{11b}$, $(CH_2)_rC(=NR^{11f})NR^{11f}R^{11f}$, $(CH_2)_rNHC(=NR^{11f})NR^{11f}R^{11f}$, $(CH_2)_rS(O)_pR^{11b}$, $(CH_2)_rS(O)_2NR^{11f}R^{11f}$, $(CH_2)_rNR^{11f}S(O)_2R^{11b}$, and $(CH_2)_r$phenyl substituted with 0–3 $R^{11e}$;

$R^{11d}$, at each occurrence, is selected from $C_{1-6}$ alkyl substituted with 0–3 $R^{11e}$, $C_{2-6}$ alkenyl, $C_{2-6}$ alkynyl, and a $C_{3-10}$ carbocyclic residue substituted with 0–3 $R^{11c}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{11f}R^{11f}$, and $(CH_2)_r$phenyl;

$R^{11f}$, at each occurrence, is selected from H, $C_{1-5}$ alkyl, and $C_{3-6}$ cycloalkyl;

$R^{12}$ is selected from H, $C_{1-6}$ alkyl, $(CH_2)_qOH$, $(CH_2)_rC_{3-6}$ cycloalkyl, and $(CH_2)_r$tphenyl substituted with 0–3 $R^{12a}$;

$R^{12a}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{9f}R^{9f}$, and $(CH_2)_r$phenyl;

$R^{13}$, at each occurrence, is selected from $C_{1-4}$ alkyl, $C_{2-8}$ alkenyl, $C_{2-8}$ alkynyl, $C_{3-6}$ cycloalkyl, $(CF_2)_wCF_3$, $CH_2NR^{13a}R^{13a'}$, $(CH_2)_rOH$, $(CH_2)_rOR^{13b}$, $(CH_2)_rSH$, $(CH_2)_rSR^{13b}$, $(CH_2)_wC(O)OH$, $(CH_2)_wC(O)R^{13b}$, $(CH_2)_wC(O)NR^{13a}R^{13'}$, $(CH_2)_rNR^{13d}C(O)R^{13a}$, $(CH_2)_wC(O)OR^{13b}$, $(CH_2)_rOC(O)R^{13b}$, $(CH_2)_wS(O)_pR^{13b}$, $(CH_2)_wS(O)_2NR^{13a}R^{13a'}$, $(CH_2)_rNR^{13d}S(O)_2R^{13b}$, and $(CH_2)_w$-phenyl substituted with 0–3 $R^{13c}$;

$R^{13a}$ and $R^{13a'}$, at each occurrence, are selected from H, $C_{1-6}$ alkyl, $C_{3-6}$ cycloalkyl, and phenyl substituted with 0–3 $R^{13c}$;

$R^{13b}$, at each occurrence, is selected from $C_{1-6}$ alkyl, $C_{3-6}$ cycloalkyl, and phenyl substituted with 0–3 $R^{13c}$;

$R^{13c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{13d}R^{13d}$;

$R^{13d}$, at each occurrence, is selected from H, $C_{1-6}$ alkyl, and $C_{3-6}$ cycloalkyl;

$R^{14}$ is selected from $C_{1-4}$ alkyl, $C_{2-8}$ alkenyl, $C_{2-8}$ alkynyl, $(CH_2)_rC_{3-6}$ cycloalkyl, $C(O)NR^{14a}R^{14a'}$, $C(O)R^{14b}$, $C(O)OC_{1-4}$ alkyl, $(CH_2)_rS(O)_pR^{14b}$, $(CH_2)_r$phenyl substituted with 0–3 $R^{14c}$;

$R^{14a}$ and $R^{14a'}$, at each occurrence, are selected from H, $C_{1-6}$ alkyl, $(CH_2)_rC_{3-6}$ cycloalkyl, and $(CH_2)_r$phenyl substituted with 0–3 $R^{14c}$, and a $(CH_2)_r$-5–10 membered heterocyclic system containing 1–4 heteroatoms selected from N, O, and S, substituted with 0–2 $R^{14c}$;

$R^{14b}$, at each occurrence, is selected from $C_{1-6}$ alkyl, $(CH_2)_rC_{3-6}$ cycloalkyl, and $(CH_2)_r$phenyl substituted with 0–3 $R^{14c}$, and a $(CH_2)_r$-5–10 membered heterocyclic system containing 1–4 heteroatoms selected from N, O, and S, substituted with 0–2 $R^{14}c$; and $R^{14c}$, at each occurrence, is selected from $C_{1-6}$ alkyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, $(CH_2)_w$phenyl;

$R^{15}$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{15a}R^{15a'}$, $(CHR')_rOH$, $(CHR')_rO$ $(CHR')_rR^{15d}$, $(CHR')_rSH$, $(CHR')_rC(O)H$, $(CHR')_rS$ $(CHR')_rR^{15d}$, $(CHR')_rC(O)OH$, $(CHR')_rC(O)(CHR')_rR^{15b}$, $(CHR')_rC(O)NR^{15a}R^{15a'}$, $(CHR')_rNR^{15f}C(O)$ $(CHR')_rR^{15b}$, $(CHR')_rC(O)O(CHR')_rR^{15d}$, $(CHR')_rOC(O)$ $(CHR')_rR^{15b}$, $(CHR')_rC(=NR^{15f})NR^{15a}R^{15a'}$, $(CHR')_r$ $NHC(=NR^{15f})NR^{15f}R^{15f}$, $(CHR')_rS(O)_p(CHR')_rR^{15b}$, $(CHR')_rS(O)_2NR^{15a}R^{15a'}$, $(CHR')_rNR^{15f}S(O)_2(CHR')_r$ $R^{15b}$, $C_{1-6}$ haloalkyl, $C_{2-8}$ alkenyl substituted with 0–3 R', $C_{2-8}$ alkynyl substituted with 0–3 R', $(CHR')_r$phenyl substituted with 0–3 $R^{15e}$, and a $(CH_2)_r$-5–10 membered heterocyclic system containing 1–4 heteroatoms selected from N, O, and S, substituted with 0–2 $R^{15e}$;

$R^{15a}$ and $R^{15a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{15e}$, and a $(CH_2)_r$-5–10 membered heterocyclic system containing 1–4 heteroatoms selected from N, O, and S, substituted with 0–2 $R^{15e}$;

$R^{15b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–3 $R^{15e}$, and $(CH_2)_r$-5–6 membered heterocyclic system containing 1–4 heteroatoms selected from N, O, and S, substituted with 0–2 $R^{15e}$;

$R^{15d}$, at each occurrence, is selected from $C_{2-8}$ alkenyl, $C_{2-8}$ alkynyl, $C_{1-6}$ alkyl substituted with 0–3 $R^{15e}$, a $(CH_2)_r$—$C_{3-10}$ carbocyclic residue substituted with 0–3 $R^{15e}$, and a $(CH_2)_r$-5–6 membered heterocyclic system containing 1–4 heteroatoms selected from N, O, and S, substituted with 0–3 $R^{15e}$;

$R^{15e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{15f}R^{15f}$, and $(CH_2)_r$phenyl;

$R^{15f}$, at each occurrence, is selected from H, $C_{1-5}$ alkyl, $C_{3-6}$ cycloalkyl, and phenyl;

$R^{16}$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{16a}R^{16a'}$, $(CHR')_rOH$, $(CHR')_rO$ $(CHR')_rR^{16d}$, $(CHR')_rSH$, $(CHR')_rC(O)H$, $(CHR')_rS$ $(CHR')_rR^{16d}$, $(CHR')_rC(O)OH$, $(CHR')_rC(O)(CHR')_r$ $R^{16b}$, $(CHR')_rC(O)NR^{16a}R^{16a'}$, $(CHR')_rNR^{16f}C(O)$ $(CHR')_rR^{16b}$, $(CHR')_rC(O)O(CHR')_rR^{16d}$, $(CHR')_rOC(O)$ $(CHR')_rR^{16b}$, $(CHR')_rC(=NR^{16f})NR^{16a}R^{16a'}$, $(CHR')_r$ $NHC(=NR^{16f})NR^{16f}R^{16f}$, $(CHR')_rS(O)_p(CHR')_rR^{16b}$, $(CHR')_rS(O)_2NR^{16a}R^{16a'}$, $(CHR')_rNR^{16f}S(O)_2(CHR')_r$ $R^{16b}$, $C_{1-6}$ haloalkyl, $C_{2-8}$ alkenyl substituted with 0–3 R', $C_{2-8}$ alkynyl substituted with 0–3 R', and $(CHR')_r$phenyl substituted with 0–3 $R^{16e}$;

$R^{16a}$ and $R^{16a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{16e}$, and a $(CH_2)_r$-5–10 membered heterocyclic system containing 1–4 heteroatoms selected from N, O, and S, substituted with 0–2 $R^{16e}$;

$R^{16b}$, at each occurrence, is selected from $C_{1-6}$ alkyl, $C_{2-8}$ alkenyl, $C_{2-8}$ alkynyl, a $(CH_2)_rC_{3-6}$ carbocyclic residue substituted with 0–3 $R^{16e}$, and a $(CH_2)_r$-5–6 membered heterocyclic system containing 1–4 heteroatoms selected from N, O, and S, substituted with 0–2 $R^{16e}$;

$R^{16d}$, at each occurrence, is selected from $C_{2-8}$ alkenyl, $C_{2-8}$ alkynyl, $C_{1-6}$ alkyl substituted with 0–3 $R^{16e}$, a $(CH_2)_r$—$C_{3-10}$ carbocyclic residue substituted with 0–3 $R^{16e}$, and a $(CH_2)_r$-5–6 membered heterocyclic system containing 1–4 heteroatoms selected from N, O, and S, substituted with 0–3 $R^{16e}$;

$R^{16e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{16}$R$^{16'}$, and (CH$_2$)$_r$phenyl;

R$^{16'}$, at each occurrence, is selected from H, C$_{1-5}$ alkyl, and C$_{3-6}$ cycloalkyl, and phenyl;

v is selected from 0, 1, and 2;

t is selected from 1 and 2;

w is selected from 0 and 1;

r is selected from 0, 1, 2, 3, 4, and 5;

q is selected from 1, 2, 3, 4, and 5; and p is selected from 1, 2, and 3.

[2] In a preferred embodiment, the present invention provides novel compounds of formula I, wherein:

Z is selected from C(O)R$^3$, S(O)$_2$R$^3$, C(O)OR$^3$, C(O)NR$^2$R$^3$, C(=NR$^1$)NR$^2$R$^3$, and (CR'R')$_t$-phenyl substituted with 0–5 R$^{15}$;

R$^4$ is absent, taken with the nitrogen to which it is attached to form an N-oxide, or selected from C$_{1-8}$ alkyl, (CH$_2$)$_r$C$_{3-6}$ cycloalkyl, and (CH$_2$)$_r$-phenyl substituted with 0–3 R$^{4c}$;

R$^{4c}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, (CH$_2$)$_r$OH, (CH$_2$)$_r$RC$_{1-5}$ alkyl, (CH$_2$)$_r$NR$^{4a}$R$^{4a'}$, and (CH$_2$)$_r$phenyl;

alternatively, R$^4$ joins with R$^7$, R$^9$, or R$^{11}$ to form a 5, 6 or 7 membered piperidinium spirocycle substituted with 0–3 R$^a$;

R$^2$ is independently selected from H and C$_{1-4}$ alkyl;

R$^6$, at each occurrence, is selected from C$_{1-4}$ alkyl, C$_{2-8}$ alkenyl, C$_{2-8}$ alkynyl, (CH$_2$)$_r$C$_{3-6}$ cycloalkyl, (CF$_2$)$_r$CF$_3$, CN, (CH$_2$)$_r$OH, (CH$_2$)$_r$OR$^{6b}$, (CH$_2$)$_r$C(O)R$^{6b}$, (CH$_2$)$_r$C(O)NR$^{6a}$R$^{6a'}$, (CH$_2$)$_r$NR$^{6d}$C(O)R$^{6a}$, and (CH$_2$)$_r$phenyl substituted with 0–3 R$^{6c}$;

R$^{6a}$ and R$^{6a'}$, at each occurrence, are selected from H, C$_{1-6}$ alkyl, C$_{3-6}$ cycloalkyl, and phenyl substituted with 0–3 R$^{6c}$;

R$^{6b}$, at each occurrence, is selected from C$_{1-6}$ alkyl, C$_{3-6}$ cycloalkyl, and phenyl substituted with 0–3 R$^{6c}$;

R$^{6c}$, at each occurrence, is selected from C$_{1-6}$ alkyl, C$_{3-6}$ cycloalkyl, Cl, F, Br, I, CN, NO$_2$, (CF$_2$)$_r$CF$_3$, (CH$_2$)$_r$OC$_{1-5}$ alkyl, (CH$_2$)$_r$OH, (CH$_2$)$_r$SC$_{1-5}$ alkyl, and (CH$_2$)$_r$NR$^{6d}$R$^{6d}$;

R$^{6d}$, at each occurrence, is selected from H, C$_{1-6}$ alkyl, and C$_{3-6}$ cycloalkyl;

R$^7$, is selected from H, C$_{1-3}$ alkyl, (CH$_2$)$_q$C$_{3-6}$ cycloalkyl, (CH$_2$)$_q$OH, (CH$_2$)$_q$OR$^{7d}$, (CH$_2$)$_q$NR$^{7a}$R$^{7a'}$, (CH$_2$)$_r$C(O)R$^{7b}$, (CH$_2$)$_r$C(O)NR$^{7a}$R$^{7a'}$, (CH$_2$)$_q$NR$^{7a}$C(O)R$^{7a}$, C$_{1-6}$ haloalkyl, (CH$_2$)$_r$phenyl with 0–2 R$^{7c}$;

R$^{7a}$ and R$^{7a'}$, at each occurrence, are selected from H, C$_{1-6}$ alkyl, (CH$_2$)$_r$C$_{3-6}$ cycloalkyl, a (CH$_2$)$_r$phenyl substituted with 0–3 R$^{7e}$;

R$^{7b}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, (CH$_2$)$_r$phenyl substituted with 0–3 R$^{7e}$;

R$^{7c}$, at each occurrence, is selected from C$_{1-4}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{7f}$R$^{7f}$, (CH$_2$)$_r$OH, (CH$_2$)$_r$OC$_{1-4}$ alkyl, (CH$_2$)$_r$C(O)R$^{7b}$, (CH$_2$)$_r$C(O)NR$^{7f}$R$^{7f}$, (CH$_2$)$_r$NR$^{7f}$C(O)R$^{7a}$, (CH$_2$)$_r$S(O)$_p$R$^{7b}$, (CH$_2$)$_r$S(O)$_2$NR$^{7f}$R$^{7f}$, (CH$_2$)$_r$NR$^{7f}$S(O)$_2$R$^{7b}$, and (CH$_2$)$_r$phenyl substituted with 0–2 R$^{7e}$;

R$^{7d}$, at each occurrence, is selected from C$_{1-6}$ alkyl, (CH$_2$)$_r$C$_{3-6}$ cycloalkyl, (CH$_2$)$_r$phenyl substituted with 0–3 R$^{7e}$;

R$^{7e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{7f}$R$^{7f}$, and (CH$_2$)$_r$phenyl;

R$^{7f}$, at each occurrence, is selected from H, C$_{1-5}$ alkyl, and C$_{3-6}$ cycloalkyl;

R$^8$ is H or joins with R$^7$ to form C$_{3-7}$ cycloalkyl or =NR$^{8b}$;

R$^9$, is selected from H, C$_{1-3}$ alkyl, (CH$_2$)$_q$C$_{3-6}$ cycloalkyl, (CH$_2$)$_q$OH, (CH$_2$)$_q$OR$^{9d}$, (CH$_2$)$_q$NR$^{9a}$R$^{9a'}$, (CH$_2$)$_r$C(O)R$^{9b}$, (CH$_2$)$_r$C(O)NR$^{9a}$R$^{9a'}$, (CH$_2$)$_q$NR$^{9a}$C(O)R$^{9a}$, C$_{1-6}$ haloalkyl, (CH$_2$)$_r$phenyl with 0–2 R$^{9c}$, (CH$_2$)$_r$-5–10 membered heterocyclic system containing 1–4 heteroatoms selected from N, O, and S, substituted with 0–3 R$^{15}$;

R$^{9'}$, is selected from H, C$_{1-3}$ alkyl, (CH$_2$)$_r$C$_{3-6}$ cycloalkyl, (CH$_2$)$_r$OH, (CH$_2$)$_r$OR$^{9d}$, (CH$_2$)$_r$NR$^{9a}$R$^{9a'}$, (CH$_2$)$_r$C(O)R$^{9b}$, (CH$_2$)$_r$C(O)NR$^{9a}$R$^{9a'}$, (CH$_2$)$_r$NR$^{9a}$C(O)R$^{9a}$, C$_{1-6}$ haloalkyl, (CH$_2$)$_r$phenyl with 0–2 R$^{9c}$, (CH$_2$)$_r$-5–10 membered heterocyclic system containing 1–4 heteroatoms selected from N, O, and S, substituted with 0–3 R$^{15}$;

R$^{9a}$ and R$^{9a'}$, at each occurrence, are selected from H, C$_{1-6}$ alkyl, (CH$_2$)$_r$C$_{3-6}$ cycloalkyl, a (CH$_2$)$_r$phenyl substituted with 0–3 R$^{9e}$;

R$^{9b}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, (CH$_2$)$_r$phenyl substituted with 0–3 R$^{9e}$;

R$^{9c}$, at each occurrence, is selected from C$_{1-4}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{9f}$R$^{9f}$, (CH$_2$)$_r$OH, (CH$_2$)$_r$OC$_{1-4}$ alkyl, (CH$_2$)$_r$C(O)R$^{9b}$, (CH$_2$)$_r$C(O)NR$^{9f}$R$^{9f}$, (CH$_2$)$_r$NR$^{9f}$C(O)R$^{9a}$, (CH$_2$)$_r$S(O)$_p$R$^{9b}$, (CH$_2$)$_r$S(O)$_2$NR$^{9f}$R$^{9f}$, (CH$_2$)$_r$NR$^{9f}$S(O)$_2$R$^{9b}$, and (CH$_2$)$_r$phenyl substituted with 0–2 R$^{9e}$;

R$^{9d}$, at each occurrence, is selected from C$_{1-6}$ alkyl, (CH$_2$)$_r$C$_{3-6}$ cycloalkyl, (CH$_2$)$_r$phenyl substituted with 0–3 R$^{9e}$;

R$^{9e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{9f}$R$^{9f}$, and (CH$_2$)$_r$phenyl;

R$^{9f}$, at each occurrence, is selected from H, C$_{1-5}$ alkyl and C$_{3-6}$ cycloalkyl;

R$^{10}$ is H or joins with R$^9$ to form C$_{3-7}$ cycloalkyl;

R$^{11}$, is selected from H, C$_{1-3}$ alkyl, (CH$_2$)$_q$C$_{3-6}$ cycloalkyl, (CH$_2$)$_q$OH, (CH$_2$)$_q$OR$^{11d}$, (CH$_2$)$_q$NR$^{11a}$R$^{11a'}$, (CH$_2$)$_r$C(O)R$^{11b}$, (CH$_2$)$_r$C(O)NR$^{11a}$R$^{11a'}$, (CH$_2$)$_q$NR$^{11a}$C(O)R$^{11a}$, C$_{1-6}$ haloalkyl, (CH$_2$)$_r$phenyl with 0–2 R$^{11c}$, (CH$_2$)$_r$-5–10 membered heterocyclic system containing 1–4 heteroatoms selected from N, O, and S, substituted with 0–3 R$^{15}$;

R$^{11'}$, is selected from H, C$_{1-3}$ alkyl, (CH$_2$)$_q$C$_{3-6}$ cycloalkyl, (CH$_2$)$_q$OH, (CH$_2$)$_q$OR$^{11d}$, (CH$_2$)$_q$NR$^{11a}$R$^{11a'}$, (CH$_2$)$_r$C(O)R$^{11b}$, (CH$_2$)$_r$C(O)NR$^{11a}$R$^{11a'}$, (CH$_2$)$_q$NR$^{11a}$C(O)R$^{11a}$, C$_{1-6}$ haloalkyl, (CH$_2$)$_r$phenyl with 0–2 R$^{11c}$, (CH$_2$)$_r$-5–10 membered heterocyclic system containing 1–4 heteroatoms selected from N, O, and S, substituted with 0–3 R$^{15}$;

R$^{11a}$ and R$^{11a'}$, at each occurrence, are selected from H, C$_{1-6}$ alkyl, (CH$_2$)$_r$C$_{3-6}$ cycloalkyl, a (CH$_2$)$_r$phenyl substituted with 0–3 R$^{11e}$;

R$^{11b}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, (CH$_2$)$_r$phenyl substituted with 0–3 R$^{11e}$;

R$^{11c}$, at each occurrence, is selected from C$_{1-4}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{11f}$R$^{11f}$, (CH$_2$)$_r$OH, (CH$_2$)$_r$OC$_{1-4}$ alkyl, (CH$_2$)$_r$C(O)R$^{11b}$, (CH$_2$)$_r$C(O)NR$^{11f}$R$^{11f}$, (CH$_2$)$_r$NR$^{11f}$C(O)R$^{11a}$, (CH$_2$)$_r$S(O)$_p$R$^{11b}$, (CH$_2$)$_r$S(O)$_2$NR$^{11f}$R$^{11f}$, (CH$_2$)$_r$NR$^{11f}$S(O)$_2$R$^{11b}$, and (CH$_2$)$_r$phenyl substituted with 0–2 R$^{11e}$;

R$^{11d}$, at each occurrence, is selected from C$_{1-6}$ alkyl, (CH$_2$)$_r$C$_{3-6}$ cycloalkyl, (CH$_2$)$_r$phenyl substituted with 0–3 R$^{11e}$;

R$^{11e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{11f}$R$^{11f'}$, and (CH$_2$)$_r$phenyl;

R$^{11f}$, at each occurrence, is selected from H, C$_{1-5}$ alkyl and C$_{3-6}$ cycloalkyl;

R$^{12}$ is H or joins with R$^{11}$ to form C$_{3-7}$ cycloalkyl;

R$^{13}$, at each occurrence, is selected from C$_{1-4}$ alkyl, C$_{3-6}$ cycloalkyl, (CH$_2$)$_q$NR$^{13a}$R$^{13a'}$, (CH$_2$)$_q$OH, (CH$_2$)$_q$OR$^{13b}$, (CH$_2$)$_w$C(O)R$^{13b}$, (CH$_2$)$_w$C(O)NR$^{13a}$R$^{13a'}$, (CH$_2$)$_q$NR$^{13d}$C(O)R$^{13a}$, (CH$_2$)$_w$S(O)$_2$NR$^{13a}$R$^{13a'}$, (CH$_2$)$_q$NR$^{13d}$S(O)$_2$R$^{13b}$, and (CH$_2$)$_w$-phenyl substituted with 0–3 R$^{13c}$;

R$^{13a}$ and R$^{13a'}$, at each occurrence, are selected from H, C$_{1-6}$ alkyl, C$_{3-6}$ cycloalkyl, and phenyl substituted with 0–3 R$^{13c}$;

R$^{13b}$, at each occurrence, is selected from C$_{1-6}$ alkyl, C$_{3-6}$ cycloalkyl, and phenyl substituted with 0–3 R$^{13c}$;

R$^{13c}$, at each occurrence, is selected from C$_{1-6}$ alkyl, C$_{3-6}$ cycloalkyl, Cl, F, Br, I, CN, NO$_2$, (CF$_2$)$_r$CF$_3$, (CH$_2$)$_r$OC$_{1-5}$ alkyl, (CH$_2$)$_r$OH, and (CH$_2$)$_r$NR$^{13d}$R$^{13d'}$;

R$^{13d}$, at each occurrence, is selected from H, C$_{1-6}$ alkyl, and C$_{3-6}$ cycloalkyl;

v is selected from 1 and 2;

q is selected from 1, 2, and 3; and r is selected from 0, 1, 2, and 3.

[3] In a more preferred embodiment, the present invention provides novel compounds of formula I, wherein:

R$^3$ is selected from a (CR$^{3'}$H)$_r$-carbocyclic residue substituted with 0–5 R$^{15}$, wherein the carbocyclic residue is selected from phenyl, C$_{3-6}$ cycloalkyl, naphthyl, and adamantyl; and a (CR$^{3'}$H)$_r$-heterocyclic system substituted with 0–3 R$^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, isoindolyl, piperidinyl, pyrrazolyl, 1,2,4-triazolyl, 1,2,3-triazolyl, tetrazolyl, thiazolyl, oxazolyl, pyrazinyl, and pyrimidinyl; and R$^5$ is selected from (CR$^{5'}$H)$_r$-phenyl substituted with 0–5 R$^{16}$; and a (CR$^{5'}$H)$_r$-heterocyclic system substituted with 0–3 R$^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, isoindolyl, piperidinyl, pyrrazolyl, 1,2,4-triazolyl, 1,2,3-triazolyl, tetrazolyl, thiazolyl, oxazolyl, pyrazinyl, and pyrimidinyl.

[4] In a further more preferred embodiment, the present invention provides novel compounds of formula I, wherein:

Y is selected from:

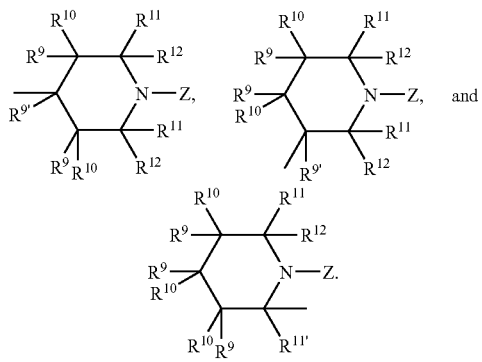

[5] In an even further more preferred embodiment, the present invention provides novel compounds of formula I, wherein:

R$^9$ is selected from H, C$_{1-4}$ alkyl, and (CH$_2$)$_r$phenyl;

R$^{10}$ is selected from H, C$_{1-4}$ alkyl, and (CH$_2$)$_r$phenyl;

R$^{11}$ is selected from H, C$_{1-4}$ alkyl, and (CH$_2$)$_r$phenyl; and

R$^{12}$ is selected from H, C$_{1-4}$ alkyl, and (CH$_2$)$_r$phenyl.

[6] In an even further more preferred embodiment, the present invention provides novel compounds of formula I-i:

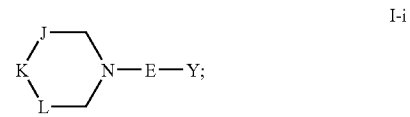

I-i wherein:

R$^{16}$, at each occurrence, is selected from C$_{1-8}$ alkyl, (CH$_2$)$_r$C$_{3-6}$ cycloalkyl, CF$_3$, Cl, Br, I, F, (CH$_2$)$_r$NR$^{16a}$R$^{16a'}$, NO$_2$, CN, OH, (CH$_2$)$_r$OR$^{16d}$, (CH$_2$)$_r$C(O)R$^{16b}$, (CH$_2$)$_r$C(O)NR$^{16a}$R$^{16a'}$, (CH$_2$)$_r$NR$^{16f}$C(O)R$^{16b}$, (CH$_2$)$_r$S(O)$_p$R$^{16b}$, (CH$_2$)$_r$S(O)$_2$NR$^{16a}$R$^{16a'}$, (CH$_2$)$_r$NR$^{16f}$S(O)$_2$R$^{16b}$, and (CH$_2$)$_r$phenyl substituted with 0–3 R$^{16e}$;

R$^{16a}$ and R$^{16a'}$, at each occurrence, are selected from H, C$_{1-6}$ alkyl, C$_{3-6}$ cycloalkyl, and (CH$_2$)$_r$phenyl substituted with 0–3 R$^{16e}$;

R$^{16b}$, at each occurrence, is selected from H, C$_{1-6}$ alkyl, C$_{3-6}$ cycloalkyl, and (CH$_2$)$_r$phenyl substituted with 0–3 R$^{16e}$;

R$^{16d}$, at each occurrence, is selected from C$_{1-6}$ alkyl and phenyl;

R$^{16e}$, at each occurrence, is selected from C$_{1-6}$ alkyl, Cl, F, Br, I, CN, NO$_2$, (CF$_2$)$_r$CF$_3$, OH, and (CH$_2$)$_r$OC$_{1-5}$ alkyl; and R$^{16f}$, at each occurrence, is selected from H, and C$_{1-5}$ alkyl.

[7] In a preferred embodiment of formula I-i, the present invention provides novel compounds, wherein:

R$^3$ is a C$_{3-10}$ carbocyclic residue substituted with 0–3 R$^{15}$, wherein the carbocyclic residue is selected from cyclopropyl, cyclopentyl, cyclohexyl, phenyl, and adamantyl;

R$^{15}$, at each occurrence, is selected from C$_{1-8}$ alkyl, (CH$_2$)$_r$C$_{3-6}$ cycloalkyl, CF$_3$, Cl, Br, I, F, (CH$_2$)$_r$NR$^{15a}$R$^{15a'}$, NO$_2$, CN, OH, (CH$_2$)$_r$OR$^{15d}$, (CH$_2$)$_r$C(O)R$^{15b}$, (CH$_2$)$_r$C(O)NR$^{15a}$R$^{15a'}$, (CH$_2$)$_r$NR$^{15f}$C(O)R$^{15b}$, (CH$_2$)$_r$S(O)$_p$R$^{15b}$, (CH$_2$)$_r$S(O)$_2$NR$^{15a}$R$^{15a'}$, (CH$_2$)$_r$NR$^{15f}$S(O)$_2$R$^{15b}$, (CH$_2$)$_r$phenyl substituted with 0–3 R$^{15e}$, and a (CH$_2$)$_r$-5–6 membered heterocyclic system containing 1–4 heteroatoms selected from N, O, and S, substituted with 0–2 R$^{15e}$;

R$^{15a}$ and R$^{15a'}$, at each occurrence, are selected from H, C$_{1-6}$ alkyl, C$_{3-6}$ cycloalkyl, and (CH$_2$)$_r$phenyl substituted with 0–3 R$^{15e}$;

R$^{15b}$, at each occurrence, is selected from H, C$_{1-6}$ alkyl, C$_{3-6}$ cycloalkyl, and (CH$_2$)$_r$phenyl substituted with 0–3 R$^{15e}$;

R$^{15d}$, at each occurrence, is selected from C$_{1-6}$ alkyl and phenyl;

R$^{15e}$, at each occurrence, is selected from C$_{1-6}$ alkyl, Cl, F, Br, I, CN, NO$_2$, (CF$_2$)$_r$CF$_3$, OH, and (CH$_2$)$_r$OC$_{1-5}$ alkyl; and R$^{15f}$, at each occurrence, is selected from H, and C$_{1-5}$ alkyl;

R$^5$ is CH$_2$-phenyl substituted with 0–3 R$^{16}$; and r is selected from 0, 1, and 2.

[8] In a more preferred embodiment of formula I-i, the present invention provides novel compounds, wherein:

E is —CH$_2$—; and

Y is

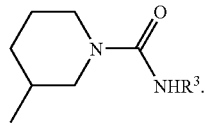

[9] In another even more preferred embodiment, the present invention provides novel compounds of formula I-ii:

I-ii

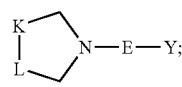

wherein:
$R^{16}$, at each occurrence, is selected from $C_{1-8}$ alkyl, $(CH_2)_r$ $C_{3-6}$ cycloalkyl, $CF_3$, Cl, Br, I, F, $(CH_2)_rNR^{16a}R^{16a'}$, $NO_2$, CN, OH, $(CH_2)_rOR^{16d}$, $(CH_2)_rC(O)R^{16b}$, $(CH_2)_rC(O)NR^{16a}R^{16a'}$, $(CH_2)_rNR^{16f}C(O)R^{16b}$, $(CH_2)_rS(O)_pR^{16b}$, $(CH_2)_rS(O)_2NR^{16a}R^{16a'}$, $(CH_2)_rNR^{16f}S(O)_2R^{16b}$, and $(CH_2)_r$phenyl substituted with 0–3 $R^{16e}$;

$R^{16a}$ and $R^{16a'}$, at each occurrence, are selected from H, $C_{1-6}$ alkyl, $C_{3-6}$ cycloalkyl, and $(CH_2)_r$phenyl substituted with 0–3 $R^{16e}$;

$R^{16b}$, at each occurrence, is selected from H, $C_{1-6}$ alkyl, $C_{3-6}$ cycloalkyl, and $(CH_2)_r$phenyl substituted with 0–3 $R^{16e}$;

$R^{16d}$, at each occurrence, is selected from $C_{1-6}$ alkyl and phenyl;

$R^{16e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{16f}$, at each occurrence, is selected from H, and $C_{1-5}$ alkyl.

[10] In a preferred embodiment of formula I-ii, the present invention provides novel compounds, wherein:
$R^3$ is a $C_{3-10}$ carbocyclic residue substituted with 0–3 $R^{15}$, wherein the carbocyclic residue is selected from cyclopropyl, cyclopentyl, cyclohexyl, phenyl, and adamantyl;

$R^{15}$, at each occurrence, is selected from $C_{1-8}$ alkyl, $(CH_2)_r$ $C_{3-6}$ cycloalkyl, $CF_3$, Cl, Br, I, F, $(CH_2)_rNR^{15a}R^{15a'}$, $NO_2$, CN, OH, $(CH_2)_rOR^{15d}$, $(CH_2)_rC(O)R^{15b}$, $(CH_2)_rC(O)NR^{15a}R^{15a'}$, $(CH_2)_rNR^{15f}C(O)R^{15b}$, $(CH_2)_rS(O)_pR^{15b}$, $(CH_2)_rS(O)_2NR^{15a}R^{15a'}$, $(CH_2)_rNR^{15f}S(O)_2R^{15b}$, $(CH_2)_r$phenyl substituted with 0–3 $R^{15e}$, and a $(CH_2)_r$-5–6 membered heterocyclic system containing 1–4 heteroatoms selected from N, O, and S, substituted with 0–2 $R^{15e}$;

$R^{15a}$ and $R^{15a'}$, at each occurrence, are selected from H, $C_{1-6}$ alkyl, $C_{3-6}$ cycloalkyl, and $(CH_2)_r$phenyl substituted with 0–3 $R^{15e}$;

$R^{15b}$, at each occurrence, is selected from H, $C_{1-6}$ alkyl, $C_{3-6}$ cycloalkyl, and $(CH_2)_r$phenyl substituted with 0–3 $R^{15e}$;

$R^{15d}$, at each occurrence, is selected from $C_{1-6}$ alkyl and phenyl;

$R^{15e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{15f}$, at each occurrence, is selected from H, and $C_{1-5}$ alkyl;
$R^5$ is $CH_2$-phenyl substituted with 0–3 $R^{16}$; and
r is selected from 0, 1, and 2.

[11] In a more preferred embodiment of formula I-ii, the present invention provides novel compounds, wherein:
E is —$CH_2$—; and Y is

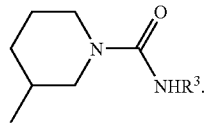

[12] In another further more preferred embodiment, the present invention provides novel compounds of formula I, wherein:
Y is selected from:

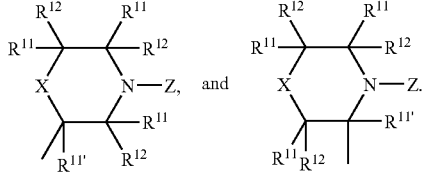

[13] In an even more preferred embodiment, the present invention provides novel compounds of formula I, wherein:
$R^9$ is selected from H, $C_{1-4}$ alkyl, and $(CH_2)_r$phenyl;
$R^{10}$ is selected from H, $C_{1-4}$ alkyl, and $(CH_2)_r$phenyl;
$R^{11}$ is selected from H, $C_{1-4}$ alkyl, and $(CH_2)_r$phenyl; and
$R^{12}$ is selected from H, $C_{1-4}$ alkyl, and $(CH_2)_r$phenyl.

[14] In an even more preferred embodiment, the present invention provides novel compounds of formula I-i:

I-i

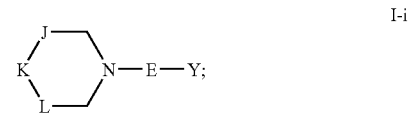

wherein:
$R^{16}$, at each occurrence, is selected from $C_{1-8}$ alkyl, $(CH_2)_r$ $C_{3-6}$ cycloalkyl, $CF_3$, Cl, Br, I, F, $(CH_2)_rNR^{16a}R^{16a'}$, $NO_2$, CN, OH, $(CH_2)_rOR^{16d}$, $(CH_2)_rC(O)R^{16b}$, $(CH_2)_rC(O)NR^{16a}R^{16a'}$, $(CH_2)_rNR^{16f}C(O)R^{16b}$, $(CH_2)_rS(O)_pR^{16b}$, $(CH_2)_rS(O)_2NR^{16a}R^{16a'}$, $(CH_2)_rNR^{16f}S(O)_2R^{16b}$, and $(CH_2)_r$phenyl substituted with 0–3 $R^{16e}$;

$R^{16a}$ and $R^{16a'}$, at each occurrence, are selected from H, $C_{1-6}$ alkyl, $C_{3-6}$ cycloalkyl, and $(CH_2)_r$phenyl substituted with 0–3 $R^{16e}$;

$R^{16b}$, at each occurrence, is selected from H, $C_{1-6}$ alkyl, $C_{3-6}$ cycloalkyl, and $(CH_2)_r$phenyl substituted with 0–3 $R^{16e}$;

$R^{16d}$, at each occurrence, is selected from $C_{1-6}$ alkyl and phenyl;

$R^{16e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{16f}$, at each occurrence, is selected from H, and $C_{1-5}$ alkyl.

[15] In a preferred embodiment of formula I-i, the present invention provides novel compounds, wherein:
$R^3$ is a $C_{3-10}$ carbocyclic residue substituted with 0–3 $R^{15}$, wherein the carbocyclic residue is selected from cyclopropyl, cyclopentyl, cyclohexyl, phenyl, and adamantyl;

$R^{15}$, at each occurrence, is selected from $C_{1-8}$ alkyl, $(CH_2)_r$ $C_{3-6}$ cycloalkyl, $CF_3$, Cl, Br, I, F, $(CH_2)_rNR^{15a}R^{15a'}$, CN, OH, $(CH_2)_rOR^{15d}$, $(CH_2)_rC(O)R^{15b}$, $(CH_2)_rC(O)NR^{15a}R^{15a'}$, $(CH_2)_rNR^{15f}C(O)R^{15b}$, $(CH_2)_rS(O)_pR^{15b}$, $(CH_2)_rS(O)_2NR^{15a}R^{15a'}$, $(CH_2)_rNR^{15f}S(O)_2R^{15b}$, $(CH_2)_r$phenyl substituted with 0–3 $R^{15e}$, and a $(CH_2)_r$-5–6 membered heterocyclic system containing 1–4 heteroatoms selected from N, O, and S, substituted with 0–2 $R^{15e}$;

$R^{15a}$ and $R^{15a'}$, at each occurrence, are selected from H, $C_{1-6}$ alkyl, $C_{3-6}$ cycloalkyl, and $(CH_2)_r$phenyl substituted with 0–3 $R^{15e}$;

$R^{15b}$, at each occurrence, is selected from H, $C_{1-6}$ alkyl, $C_{3-6}$ cycloalkyl, and $(CH_2)_r$phenyl substituted with 0–3 $R^{15e}$;

$R^{15d}$, at each occurrence, is selected from $C_{1-6}$ alkyl and phenyl;

$R^{15e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{15f}$, at each occurrence, is selected from H, and $C_{1-5}$ alkyl;

$R^5$ is $CH_2$-phenyl substituted with 0–3 $R^{16}$; and r is selected from 0, 1, and 2.

[16] In a more preferred embodiment of formula (I-i), the present invention provides novel compounds, wherein:

E is —$CH_2$—; and

Y is

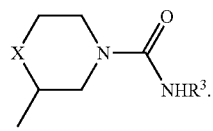

[17] In an even more preferred embodiment, the present invention provides novel compounds of formula I-ii:

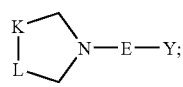

I-ii wherein:

$R^{16}$, at each occurrence, is selected from $C_{1-8}$ alkyl, $(CH_2)_r$$C_{3-6}$ cycloalkyl, $CF_3$, Cl, Br, I, F, $(CH_2)_rNR^{16a}R^{16a'}$, $NO_2$, CN, OH, $(CH_2)_rOR^{16d}$, $(CH_2)_rC(O)R^{16b}$, $(CH_2)_rC(O)NR^{16a}R^{16a'}$, $(CH_2)_rNR^{16f}C(O)R^{16b}$, $(CH_2)_rS(O)_pR^{16b}$, $(CH_2)_rS(O)_2NR^{16a}R^{16a'}$, $(CH_2)_rNR^{16f}S(O)_2R^{16b}$, and $(CH_2)_r$phenyl substituted with 0–3 $R^{16e}$;

$R^{16a}$ and $R^{16a'}$, at each occurrence, are selected from H, $C_{1-6}$ alkyl, $C_{3-6}$ cycloalkyl, and $(CH_2)_r$phenyl substituted with 0–3 $R^{16e}$;

$R^{16b}$, at each occurrence, is selected from H, $C_{1-6}$ alkyl, $C_{3-6}$ cycloalkyl, and $(CH_2)_r$phenyl substituted with 0–3 $R^{16e}$;

$R^{16d}$, at each occurrence, is selected from $C_{1-6}$ alkyl and phenyl;

$R^{16e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{16f}$, at each occurrence, is selected from H, and $C_{1-5}$ alkyl.

[18] In a preferred embodiment of formula I-ii, the present invention provides novel compounds, wherein:

$R^3$ is a $C_{3-10}$ carbocyclic residue substituted with 0–3 $R^{15}$, wherein the carbocyclic residue is selected from cyclopropyl, cyclopentyl, cyclohexyl, phenyl, and adamantyl;

$R^{15}$, at each occurrence, is selected from $C_{1-8}$ alkyl, $(CH_2)_r$$C_{3-6}$ cycloalkyl, $CF_3$, Cl, Br, I, F, $(CH_2)_rNR^{15a}R^{15a'}$, $NO_2$, CN, OH, $(CH_2)_rOR^{15d}$, $(CH_2)_rC(O)R^{15b}$, $(CH_2)_rC(O)NR^{15a}R^{15a'}$, $(CH_2)_rNR^{15f}C(O)R^{15b}$, $(CH_2)_rS(O)_pR^{15b}$, $(CH_2)_rS(O)_2NR^{15a}R^{15a'}$, $(CH_2)_rNR^{15f}S(O)_2R^{15b}$, $(CH_2)_r$phenyl substituted with 0–3 $R^{15e}$, and a $(CH_2)_r$-5–6 membered heterocyclic system containing 1–4 heteroatoms selected from N, O, and S, substituted with 0–2 $R^{15e}$;

$R^{15a}$ and $R^{15a'}$, at each occurrence, are selected from H, $C_{1-6}$ alkyl, $C_{3-6}$ cycloalkyl, and $(CH_2)_r$phenyl substituted with 0–3 $R^{15e}$;

$R^{15b}$, at each occurrence, is selected from H, $C_{1-6}$ alkyl, $C_{3-6}$ cycloalkyl, and $(CH_2)_r$phenyl substituted with 0–3 $R^{15e}$;

$R^{15d}$, at each occurrence, is selected from $C_{1-6}$ alkyl and phenyl;

$R^{15e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{15f}$, at each occurrence, is selected from H, and $C_{1-5}$ alkyl;

$R^5$ is $CH_2$-phenyl substituted with 0–3 $R^{16}$; and r is selected from 0, 1, and 2.

[19] In a more preferred embodiment of formula I-ii, the present invention provides novel compounds, wherein:

E is —$CH_2$—; and

Y is

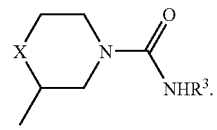

[20] In another further more preferred embodiment, the present invention provides novel compounds of formula I, wherein:

Y is selected from

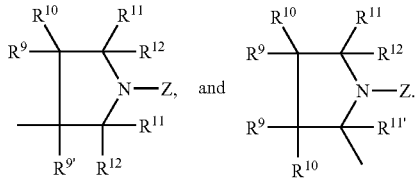

and

[21] In an even further more preferred embodiment, the present invention provides novel compounds of formula I, wherein:

$R^9$ is selected from H, $C_{1-4}$ alkyl, and $(CH_2)_r$phenyl;

$R^{10}$ is selected from H, $C_{1-4}$ alkyl, and $(CH_2)_r$phenyl;

$R^{11}$ is selected from H, $C_{1-4}$ alkyl, and $(CH_2)_r$phenyl; and $R^{12}$ is selected from H, $C_{1-4}$ alkyl, and $(CH_2)_r$phenyl.

[22] In an even further more preferred embodiment, the present invention provides novel compounds of formula I-i:

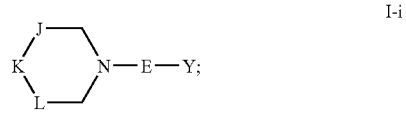

I-i wherein:

$R^{16}$, at each occurrence, is selected from $C_{1-8}$ alkyl, $(CH_2)_r$$C_{3-6}$ cycloalkyl, $CF_3$, Cl, Br, I, F, $(CH_2)_rNR^{16a}R^{16a'}$, $NO_2$, CN, OH, $(CH_2)_rOR^{16d}$, $(CH_2)_rC(O)R^{16b}$, $(CH_2)_rC(O)NR^{16a}R^{16a'}$, $(CH_2)_rNR^{16f}C(O)R^{16b}$, $(CH_2)_rS(O)_pR^{16b}$, $(CH_2)_rS(O)_2NR^{16a}R^{16a'}$, $(CH_2)_rNR^{16f}S(O)_2R^{16b}$, and $(CH_2)_r$phenyl substituted with 0–3 $R^{16e}$;

$R^{16a}$ and $R^{16a'}$, at each occurrence, are selected from H, $C_{1-6}$ alkyl, $C_{3-6}$ cycloalkyl, and $(CH_2)_r$phenyl substituted with 0–3 $R^{16e}$;

$R^{16b}$, at each occurrence, is selected from H, $C_{1-6}$ alkyl, $C_{3-6}$ cycloalkyl, and $(CH_2)_r$phenyl substituted with 0–3 $R^{16e}$;

$R^{16d}$, at each occurrence, is selected from $C_{1-6}$ alkyl and phenyl;

$R^{16e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{16f}$, at each occurrence, is selected from H, and $C_{1-5}$ alkyl.

[23] In a preferred embodiment of formula I-i, the present invention provides novel compounds, wherein:

$R^3$ is a $C_{3-10}$ carbocyclic residue substituted with 0–3 $R^{15}$, wherein the carbocyclic residue is selected from cyclopropyl, cyclopentyl, cyclohexyl, phenyl, and adamantyl;

$R^{15}$, at each occurrence, is selected from $C_{1-8}$ alkyl, $(CH_2)_r$ $C_{3-6}$ cycloalkyl, $CF_3$, Cl, Br, I, F, $(CH_2)_rNR^{15a}R^{15a'}$, $NO_2$, CN, OH, $(CH_2)_rOR^{15d}$, $(CH_2)_rC(O)R^{15b}$, $(CH_2)_rC(O)NR^{15a}R^{15a'}$, $(CH_2)_rNR^{15f}C(O)R^{15b}$, $(CH_2)_rS(O)_pR^{15b}$, $(CH_2)_rS(O)_2NR^{15a}R^{15a'}$, $(CH_2)_rNR^{15f}S(O)_2R^{15b}$, and $(CH_2)_r$phenyl substituted with 0–3 $R^{15e}$, and a $(CH_2)_r$-5–6 membered heterocyclic system containing 1–4 heteroatoms selected from N, O, and S, substituted with 0–2 $R^{15e}$;

$R^{15a}$ and $R^{15a'}$, at each occurrence, are selected from H, $C_{1-6}$ alkyl, $C_{3-6}$ cycloalkyl, and $(CH_2)_r$phenyl substituted with 0–3 $R^{15e}$;

$R^{15b}$, at each occurrence, is selected from H, $C_{1-6}$ alkyl, $C_{3-6}$ cycloalkyl, and $(CH_2)_r$phenyl substituted with 0–3 $R^{15e}$;

$R^{15d}$, at each occurrence, is selected from $C_{1-6}$ alkyl and phenyl;

$R^{15e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{15f}$, at each occurrence, is selected from H, and $C_{1-5}$ alkyl;

$R^5$ is $CH_2$-phenyl substituted with 0–3 $R^{16}$; and r is selected from 0, 1, and 2.

[24] In a more preferred embodiment of formula I-i, the present invention provides novel compounds, wherein:

E is —$CH_2$—; and

Y is

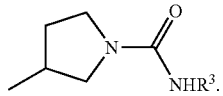

[25] In another even further more preferred embodiment, the present invention provides novel compounds of formula I-ii:

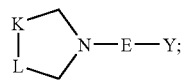

I-ii wherein:

$R^{16}$, at each occurrence, is selected from $C_{1-8}$ alkyl, $(CH_2)_r$ $C_{3-6}$ cycloalkyl, $CF_3$, Cl, Br, I, F, $(CH_2)_rNR^{16a}R^{16a'}$, $NO_2$, CN, OH, $(CH_2)_rOR^{16d}$, $(CH_2)_rC(O)R^{16b}$, $(CH_2)_rC(O)NR^{16a}R^{16a'}$, $(CH_2)_rNR^{16f}C(O)R^{16b}$, $(CH_2)_rS(O)_pR^{16b}$, $(CH_2)_rS(O)_2NR^{16a}R^{16a'}$, $(CH_2)_rNR^{16f}S(O)_2R^{16b}$, and $(CH_2)_r$phenyl substituted with 0–3 $R^{16e}$;

$R^{16a}$ and $R^{16a'}$, at each occurrence, are selected from H, $C_{1-6}$ alkyl, $C_{3-6}$ cycloalkyl, and $(CH_2)_r$phenyl substituted with 0–3 $R^{16e}$;

$R^{16b}$, at each occurrence, is selected from H, $C_{1-6}$ alkyl, $C_{3-6}$ cycloalkyl, and $(CH_2)_r$phenyl substituted with 0–3 $R^{16e}$;

$R^{16d}$, at each occurrence, is selected from $C_{1-6}$ alkyl and phenyl;

$R^{16e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{16f}$, at each occurrence, is selected from H, and $C_{1-5}$ alkyl.

[26] In a preferred embodiment of formula I-ii, the present invention provides novel compounds, wherein:

$R^3$ is a $C_{3-10}$ carbocyclic residue substituted with 0–3 $R^{15}$, wherein the carbocyclic residue is selected from cyclopropyl, cyclopentyl, cyclohexyl, phenyl, and adamantyl;

$R^{15}$, at each occurrence, is selected from $C_{1-8}$ alkyl, $(CH_2)_r$ $C_{3-6}$ cycloalkyl, $CF_3$, Cl, Br, I, F, $(CH_2)_rNR^{15a}R^{15a'}$, $NO_2$, CN, OH, $(CH_2)_rOR^{15d}$, $(CH_2)_rC(O)R^{15b}$, $(CH_2)_rC(O)NR^{15a}R^{15a}$, $(CH_2)_rNR^{15f}C(O)R^{15b}$, $(CH_2)_rS(O)_pR^{15b}$, $(CH_2)_rS(O)_2NR^{15a}R^{15a'}$, $(CH_2)_rNR^{15f}S(O)_2R^{15b}$, and $(CH_2)_r$phenyl substituted with 0–3 $R^{15e}$, and a $(CH_2)_r$-5–6 membered heterocyclic system containing 1–4 heteroatoms selected from N, O, and S, substituted with 0–2 $R^{15e}$;

$R^{15a}$ and $R^{15a'}$, at each occurrence, are selected from H, $C_{1-6}$ alkyl, $C_{3-6}$ cycloalkyl, and $(CH_2)_r$phenyl substituted with 0–3 $R^{15e}$;

$R^{15b}$, at each occurrence, is selected from H, $C_{1-6}$ alkyl, $C_{3-6}$ cycloalkyl, and $(CH_2)_r$phenyl substituted with 0–3 $R^{15e}$;

$R^{15d}$, at each occurrence, is selected from $C_{1-6}$ alkyl and phenyl;

$R^{15e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{15f}$, at each occurrence, is selected from H, and $C_{1-5}$ alkyl;

$R^5$ is $CH_2$-phenyl substituted with 0–3 $R^{16}$; and r is selected from 0, 1, and 2.

[27] In a more preferred embodiment of formula I-ii, the present invention provides novel compounds, wherein:

E is —$CH_2$—; and

Y is

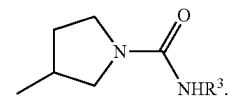

[28] In another further more preferred embodiment, the present invention provides novel compounds of formula I, wherein:

Y is selected from:

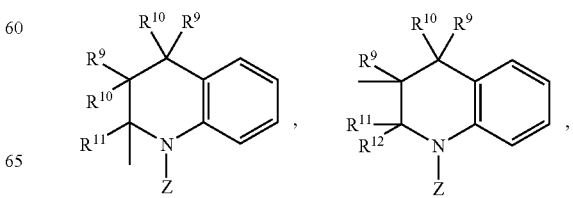

-continued

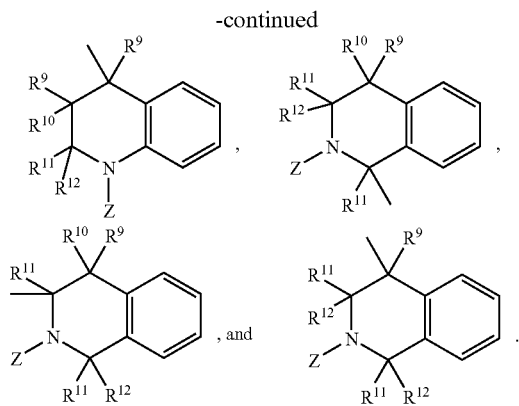

[29] In an even further more preferred embodiment, the present invention provides novel compounds of formula I, wherein:
$R^9$ is selected from H, $C_{1-4}$ alkyl, and $(CH_2)_r$phenyl;
$R^{10}$ is selected from H, $C_{1-4}$ alkyl, and $(CH_2)_r$phenyl;
$R^{11}$ is selected from H, $C_{1-4}$ alkyl, and $(CH_2)_r$phenyl; and
$R^{12}$ is selected from H, $C_{1-4}$ alkyl, and $(CH_2)_r$phenyl.

[30] In an even further more preferred embodiment, the present invention provides novel compounds of formula I-i:

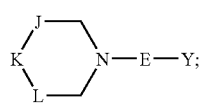
I-i wherein:
$R^{16}$, at each occurrence, is selected from $C_{1-8}$ alkyl, $(CH_2)_r$ $C_{3-6}$ cycloalkyl, $CF_3$, Cl, Br, I, F, $(CH_2)_rNR^{16a}R^{16a'}$, $NO_2$, CN, OH, $(CH_2)_rOR^{16d}$, $(CH_2)_rC(O)R^{16b}$, $(CH_2)_rC(O)NR^{16a}R^{16a'}$, $(CH_2)_rNR^{16f}C(O)R^{16b}$, $(CH_2)_rS(O)_pR^{16b}$, $(CH_2)_rS(O)_2NR^{16a}R^{16a'}$, $(CH_2)_rNR^{16f}S(O)_2R^{16b}$, and $(CH_2)_r$phenyl substituted with 0–3 $R^{16e}$;
$R^{16a}$ and $R^{16a'}$, at each occurrence, are selected from H, $C_{1-6}$ alkyl, $C_{3-6}$ cycloalkyl, and $(CH_2)_r$phenyl substituted with 0–3 $R^{16e}$;
$R^{16b}$, at each occurrence, is selected from H, $C_{1-6}$ alkyl, $C_{3-6}$ cycloalkyl, and $(CH_2)_r$phenyl substituted with 0–3 $R^{16e}$;
$R^{16d}$, at each occurrence, is selected from $C_{1-6}$ alkyl and phenyl;
$R^{16e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and
$R^{16f}$, at each occurrence, is selected from H, and $C_{1-5}$ alkyl.

[31] In a preferred embodiment of formula I-i, the present invention provides novel compounds, wherein:
$R^3$ is a $C_{3-10}$ carbocyclic residue substituted with 0–3 $R^{15}$, wherein the carbocyclic residue is selected from cyclopropyl, cyclopentyl, cyclohexyl, phenyl, and adamantyl;
$R^{15}$, at each occurrence, is selected from $C_{1-8}$ alkyl, $(CH_2)_r$ $C_{3-6}$ cycloalkyl, $CF_3$, Cl, Br, I, F, $(CH_2)_rNR^{15a}R^{15a'}$, $NO_2$, CN, OH, $(CH_2)_rOR^{15d}$, $(CH_2)_rC(O)R^{15b}$, $(CH_2)_rC(O)NR^{15a}R^{15a'}$, $(CH_2)_rNR^{15f}C(O)R^{15b}$, $(CH_2)_rS(O)_pR^{15b}$, $(CH_2)_rS(O)_2NR^{15a}R^{15a'}$, $(CH_2)_rNR^{15f}S(O)_2R^{15b}$, $(CH_2)_r$phenyl substituted with 0–3 $R^{15e}$, and a $(CH_2)_r$-5–6 membered heterocyclic system containing 1–4 heteroatoms selected from N, O, and S, substituted with 0–2 $R^{15e}$;
$R^{15a}$ and $R^{15a'}$, at each occurrence, are selected from H, $C_{1-6}$ alkyl, $C_{3-6}$ cycloalkyl, and $(CH_2)_r$phenyl substituted with 0–3 $R^{15e}$;
$R^{15b}$, at each occurrence, is selected from H, $C_{1-6}$ alkyl, $C_{3-6}$ cycloalkyl, and $(CH_2)_r$phenyl substituted with 0–3 $R^{15e}$;
$R^{15d}$, at each occurrence, is selected from $C_{1-6}$ alkyl and phenyl;
$R^{15e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and
$R^{15f}$, at each occurrence, is selected from H, and $C_{1-5}$ alkyl;
$R^5$ is $CH_2$-phenyl substituted with 0–3 $R^{16}$; and
r is selected from 0, 1, and 2.

[32] In a more preferred embodiment of formula I-i, the present invention provides novel compounds, wherein:
E is $-CH_2-$; and
Y is

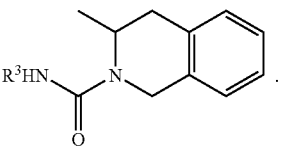

[33] In another even further more preferred embodiment, the present invention provides novel compounds of formula I-ii:

I-ii wherein:

$R^{16}$, at each occurrence, is selected from $C_{1-8}$ alkyl, $(CH_2)_r$ $C_{3-6}$ cycloalkyl, $CF_3$, Cl, Br, I, F, $(CH_2)_rNR^{16a}R^{16a'}$, $NO_2$, CN, OH, $(CH_2)_rOR^{16d}$, $(CH_2)_rC(O)R^{16b}$, $(CH_2)_rC(O)NR^{16a}R^{16a'}$, $(CH_2)_rNR^{16f}C(O)R^{16b}$, $(CH_2)_rS(O)_pR^{16b}$, $(CH_2)_rS(O)_2NR^{16a}R^{16a'}$, $(CH_2)_rNR^{16f}S(O)_2R^{16b}$, $(CH_2)_r$phenyl substituted with 0–3 $R^{16e}$, and a $(CH_2)_r$-5–6 membered heterocyclic system containing 1–4 heteroatoms selected from N, O, and S, substituted with 0–2 $R^{15e}$;
$R^{16a}$ and $R^{16a'}$, at each occurrence, are selected from H, $C_{1-6}$ alkyl, $C_{3-6}$ cycloalkyl, and $(CH_2)_r$phenyl substituted with 0–3 $R^{16e}$;
$R^{16b}$, at each occurrence, is selected from H, $C_{1-6}$ alkyl, $C_{3-6}$ cycloalkyl, and $(CH_2)_r$phenyl substituted with 0–3 $R^{16e}$;
$R^{16d}$, at each occurrence, is selected from $C_{1-6}$ alkyl and phenyl;
$R^{16e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and
$R^{16f}$, at each occurrence, is selected from H, and $C_{1-5}$ alkyl.

[34] In a preferred embodiment of formula I-ii, the present invention provides novel compounds, wherein:
$R^3$ is a $C_{3-10}$ carbocyclic residue substituted with 0–3 $R^{15}$, wherein the carbocyclic residue is selected from cyclopropyl, cyclopentyl, cyclohexyl, phenyl, and adamantyl;
$R^{15}$, at each occurrence, is selected from $C_{1-8}$ alkyl, $(CH_2)_r$ $C_{3-6}$ cycloalkyl, $CF_3$, Cl, Br, I, F, $(CH_2)_rNR^{15a}R^{15a'}$, $NO_2$, CN, OH, $(CH_2)_rOR^{15d}$, $(CH_2)_rC(O)R^{15b}$, $(CH_2)_rC(O)NR^{15a}R^{15a'}$, $(CH_2)_rNR^{15f}C(O)R^{15b}$, $(CH_2)_rS(O)_pR^{15b}$, $(CH_2)_rS(O)_2NR^{15a}R^{15a'}$, $(CH_2)_rNR^{15f}S(O)_2R^{15b}$, (CH$_2$)$_r$-phenyl substituted with 0–3 R$^{15e}$, and a (CH$_2$)$_r$-5–6 membered heterocyclic system containing 1–4 heteroatoms selected from N, O, and S, substituted with 0–2 R$^{15e}$;

R$^{15a}$ and R$^{15a'}$, at each occurrence, are selected from H, C$_{1-6}$ alkyl, C$_{3-6}$ cycloalkyl, and (CH$_2$)$_r$phenyl substituted with 0–3 R$^{15e}$;

R$^{15b}$, at each occurrence, is selected from H, C$_{1-6}$ alkyl, C$_{3-6}$ cycloalkyl, and (CH$_2$)$_r$phenyl substituted with 0–3 R$^{15e}$;

R$^{15d}$, at each occurrence, is selected from C$_{1-6}$ alkyl and phenyl;

R$^{15e}$, at each occurrence, is selected from C$_{1-6}$ alkyl, Cl, F, Br, I, CN, NO$_2$, (CF$_2$)$_r$CF$_3$, OH, and (CH$_2$)$_r$OC$_{1-5}$ alkyl; and R$^{15f}$, at each occurrence, is selected from H, and C$_{1-5}$ alkyl;

R$^5$ is CH$_2$-phenyl substituted with 0–3 R$^{16}$; and r is selected from 0, 1, and 2.

[35] In a more preferred embodiment of formula I-ii, the present invention provides novel compounds, wherein:

E is —CH$_2$—; and

Y is

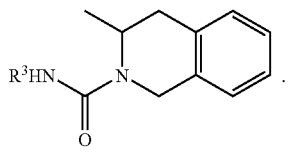

[36] In certain preferred embodiments of formula I, the present invention provides novel compounds, wherein:

R$^4$ is absent; and

R$^9$, R$^{9'}$, R$^{10}$, R$^{11}$, R$^{11'}$, R$^{12}$ and R$^{13}$ are H.

[37] In certain preferred embodiments of formula I, the present invention provides novel compounds, wherein:

R$^{16}$, at each occurrence, is selected from C$_{1-8}$ alkyl, (CH$_2$)$_r$C$_{3-6}$ cycloalkyl, CF$_3$, Cl, Br, I, F, (CH$_2$)$_r$NR$^{16a}$R$^{16a'}$, NO$_2$, CN, OH, (CH$_2$)$_r$OR$^{16d}$, (CH$_2$)$_r$C(O)R$^{16b}$, (CH$_2$)$_r$C(O)NR$^{16a}$R$^{16a'}$, (CH$_2$)$_r$NR$^{16f}$C(O)R$^{16b}$, (CH$_2$)$_r$S(O)$_p$R$^{16b}$, (CH$_2$)$_r$S(O)$_2$NR$^{16a}$R$^{16a'}$, (CH$_2$)$_r$NR$^{16f}$S(O)$_2$R$^{16b}$, and (CH$_2$)$_r$phenyl substituted with 0–3 R$^{16e}$;

R$^{16a}$ and R$^{16a'}$, at each occurrence, are selected from H, C$_{1-6}$ alkyl, C$_{3-6}$ cycloalkyl, and (CH$_2$)$_r$phenyl substituted with 0–3 R$^{16e}$;

R$^{16b}$, at each occurrence, is selected from H, C$_{1-6}$ alkyl, C$_{3-6}$ cycloalkyl, and (CH$_2$)$_r$phenyl substituted with 0–3 R$^{16e}$;

R$^{16d}$, at each occurrence, is selected from C$_{1-6}$ alkyl and phenyl;

R$^{16e}$, at each occurrence, is selected from C$_{1-6}$ alkyl, Cl, F, Br, I, CN, NO$_2$, (CF$_2$)$_r$CF$_3$, OH, and (CH$_2$)$_r$OC$_{1-5}$ alkyl; and R$^{16f}$, at each occurrence, is selected from H, and C$_{1-5}$ alkyl.

[38] In certain preferred embodiments of formula I, the present invention provides novel compounds, wherein: R$^5$ is CH$_2$-phenyl substituted with 0–3 R$^{16}$.

[39] In certain preferred embodiments of formula I, the present invention provides novel compounds, wherein R$^3$ is selected from a carbocyclic residue substituted with 0–3 R$^{15}$, wherein the carbocyclic residue is selected from phenyl and C$_{3-6}$ cycloalkyl; and a heterocyclic system substituted with 0–3 R$^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, isoindolyl, piperidinyl, pyrrazolyl, 1,2,4-triazolyl, 1,2,3-triazolyl, tetrazolyl, thiazolyl, oxazolyl, pyrazinyl, and pyrimidinyl.

[40] In certain preferred embodiments of formula I, the present invention provides novel compounds, wherein:

R$^{15}$, at each occurrence, is selected from C$_{1-8}$ alkyl, (CH$_2$)$_r$C$_{3-6}$ cycloalkyl, CF$_3$, Cl, Br, I, F, (CH$_2$)$_r$NR$^{15a}$R$^{15a'}$, NO$_2$, CN, OH, (CH$_2$)$_r$OR$^{15d}$, (CH$_2$)$_r$C(O)R$^{15b}$, (CH$_2$)$_r$C(O)NR$^{15a}$R$^{15a'}$, (CH$_2$)$_r$NR$^{15f}$C(O)R$^{15b}$, (CH$_2$)$_r$S(O)$_p$R$^{15b}$, (CH$_2$)$_r$S(O)$_2$NR$^{15a}$R$^{15a'}$, (CH$_2$)$_r$NR$^{15f}$S(O)$_2$R$^{15b}$, (CH$_2$)$_r$phenyl substituted with 0–3 R$^{15e}$, and a (CH$_2$)$_r$-5–6 membered heterocyclic system containing 1–4 heteroatoms selected from N, O, and S, substituted with 0–2 R$^{15e}$;

R$^{15a}$ and R$^{15a'}$, at each occurrence, are selected from H, C$_{1-6}$ alkyl, C$_{3-6}$ cycloalkyl, and (CH$_2$)$_r$phenyl substituted with 0–3 R$^{15e}$;

R$^{15b}$, at each occurrence, is selected from H, C$_{1-6}$ alkyl, C$_{3-6}$ cycloalkyl, and (CH$_2$)$_r$phenyl substituted with 0–3 R$^{15e}$;

R$^{15d}$, at each occurrence, is selected from C$_{1-6}$ alkyl and phenyl;

R$^{15e}$, at each occurrence, is selected from C$_{1-6}$ alkyl, Cl, F, Br, I, CN, NO$_2$, (CF$_2$)$_r$CF$_3$, OH, and (CH$_2$)$_r$OC$_{1-5}$ alkyl; and R$^{15f}$, at each occurrence, is selected from H, and C$_{1-5}$ alkyl.

[41] In certain preferred embodiments of formula I, the present invention provides novel compounds, wherein E is —CR$^7$R$^8$—. In other preferred embodiments, E is —CH$_2$—.

[42] In certain preferred embodiments of formula I, the present invention provides novel compounds, wherein Z is selected from C(O)NR$^2$R$^3$, C(=NR$^1$)NR$^2$R$^3$, C(=CHCN)NR$^2$R$^3$, C(=CHNO$_2$)NR$^2$R$^3$, and C(=C(CN)$_2$)NR$^2$R$^3$.

[43] In certain preferred embodiments of formula I, the present invention provides novel compounds, wherein:

R$^6$ is H; and when K is CHR$^5$, either:
1) M is absent, or
2) Z is other than C(O)NR$^2$R$^3$.

[44] In certain preferred embodiments of formula I, the present invention provides novel compounds, wherein Y is selected from:

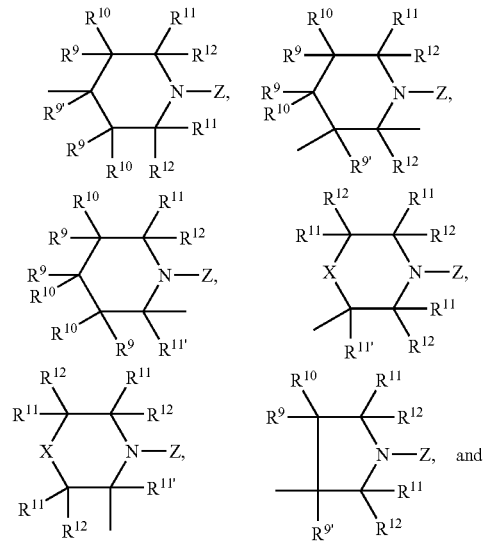

-continued

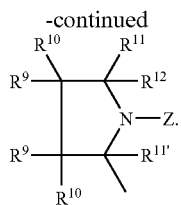

[45] In certain preferred embodiments of formula I, the present invention provides novel compounds, wherein Y is selected from:

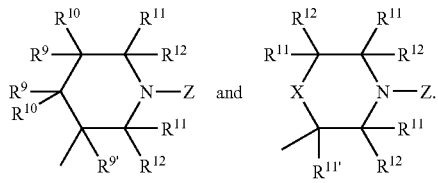

[46] In certain preferred embodiments of formula I, the present invention provides novel compounds, wherein:

$R^{16}$, at each occurrence, is selected from $C_{1-8}$ alkyl, $(CH_2)_r$ $C_{3-6}$ cycloalkyl, $CF_3$, Cl, Br, I, F, $(CH_2)_rNR^{16a}R^{16a'}$, CN, OH, $OCF_3$, $(CH_2)_rOR^{6d}$, $(CH_2)_rC(O)R^{16b}$;

$R^{16a}$ and $R^{16a'}$, at each occurrence, are selected from H, $C_{1-6}$ alkyl, and $C_{3-6}$ cycloalkyl;

$R^{16b}$, at each occurrence, is selected from H, $C_{1-6}$ alkyl, $C_{3-6}$ cycloalkyl, and $(CH_2)_r$phenyl substituted with 0–3 $R^{16e}$;

$R^{16d}$, at each occurrence, is selected from $C_{1-6}$ alkyl and phenyl.

[47] In certain preferred embodiments of formula I, the present invention provides novel compounds, wherein $R^{16}$ is selected from F, Cl, Br, $OCF_3$, and $CF_3$.

[48] In certain preferred embodiments of formula I, the present invention provides novel compounds, wherein:

$R^{15}$, at each occurrence, is selected from CN, $C(O)R^{15b}$, and a $(CH_2)_r$-5-6 membered heterocyclic system containing 1–4 heteroatoms selected from N, O, and S, substituted with 0–2 $R^{15e}$;

$R^{15b}$, at each occurrence, is selected from H, $C_{1-6}$ alkyl, $C_{3-6}$ cycloalkyl, and $(CH_2)_r$phenyl substituted with 0–3 $R^{15e}$; and $R^{15e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl.

[49] In certain preferred embodiments of formula I, the present invention provides novel compounds, wherein:

J and Q are $CH_2$; and

M is absent or $CH_2$.

[50] In certain preferred embodiments of formula I, the present invention provides novel compounds, wherein K is $CH_2$.

[51] In certain preferred embodiments of formula I, the present invention provides novel compounds, wherein Z is selected from $C(=NR^1)NR^2R^3$.

[52] In certain preferred embodiments of formula I, the present invention provides novel compounds, wherein wherein Z is selected from $C(=C(CN)_2)NR^2R^3$.

[53] In certain more preferred embodiments of formula I, the present invention provides novel compounds, wherein Z is selected from $C(=NCN)NHR^3$.

[54] In certain preferred embodiments of formula I, the present invention provides novel compounds, wherein $R^3$ is phenyl substituted with 0–3 $R^{15}$.

[55] In certain even more preferred embodiments, the present invention provides novel compounds of formula I selected from:

(+/−)-N-phenyl-3-[[4-(phenylmethyl)-1-piperidinyl]methyl]-1-piperidinecarboxamide, (+/−)-N-(3-methoxyphenyl)-3-[[4-(phenylmethyl)-1-piperidinyl]methyl]-1-piperidinecarboxamide, (+/−)-N-(3-carboethoxyphenyl)-3-[[4-(phenylmethyl)-1-piperidinyl]methyl]-1-piperidinecarboxamide, (+/−)-N-(3-cyanophenyl)-3-[[4-(phenylmethyl)-1-piperidinyl]methyl]-1-piperidinecarboxamide, (+/−)-N-(1-adamantyl)-3-[[4-(phenylmethyl)-1-piperidinyl]methyl]-1-piperidinecarboxamide, N-phenyl-4-[[4-(phenylmethyl)-1-piperidinyl]methyl]-1-piperidinecarboxamide, N-(3-cyanophenyl)-4-[[4-(phenylmethyl)-1-piperidinyl]methyl]-1-piperidinecarboxamide, N-(1-adamantyl)-4-[[4-(phenylmethyl)-1-piperidinyl]methyl]-1-piperidinecarboxamide, N-(3-methoxyphenyl)-4-[[4-(phenylmethyl)-1-piperidinyl]methyl]-1-piperidinecarboxamide, N-(3-carboethoxyphenyl)-4-[[4-(phenylmethyl)-1-piperidinyl]methyl]-1-piperidinecarboxamide, 1-benzoyl-4-[[4-(phenylmethyl)-1-piperidinyl]methyl]piperidine, 1-phenylacetyl-4-[[4-(phenylmethyl)-1-piperidinyl]methyl]piperidine, 1-(3,4-dimethoxybenzoyl)-4-[[4-(phenylmethyl)-1-piperidinyl]methyl]piperidine, 1-(3,5-dichlorobenzoyl)-4-[[4-(phenylmethyl)-1-piperidinyl]methyl]piperidine, 1-(3,5-difluorobenzoyl)-4-[[4-(phenylmethyl)-1-piperidinyl]methyl]piperidine, 1-(3,5-dimethoxybenzoyl)-4-[[4-(phenylmethyl)-1-piperidinyl]methyl]piperidine, 1-(3,4-methylenedioxybenzoyl)-4-[[4-(phenylmethyl)-1-piperidinyl]methyl]piperidine, 1-(2-thiophenesulfonyl)-4-[[(4-(phenylmethyl)-1-piperidinyl]methyl]-piperidinecarboxamide, 1-(3-methoxyphenylacetyl)-4-[[4-(phenylmethyl)-1-piperidinyl]methyl]piperidine, 1-(4-methoxyphenylacetyl)-4-[[4-(phenylmethyl)-1-piperidinyl]methyl]piperidine, (+/−)-N-phenyl-3-[[4-[(4-fluorophenyl)methyl]-1-piperidinyl]methyl]-1-piperidinecarboxamide, (+/−)-N-(3-cyanophenyl)-3-[[4-[(4-fluorophenyl)methyl]-1-piperidinyl]methyl]-1-piperidinecarboxamide, (+/−)-N-(1-adamantylphenyl)-3-[[4-[(4-fluorophenyl)methyl]-1-piperidinyl]methyl]-1-piperidinecarboxamide, (+/−)-N-(3-carboethoxyphenyl)-3-[[4-[(4-fluorophenyl)methyl]-1-piperidinyl]methyl]-1-piperidinecarboxamide, (+/−)-N-(4-fluorophenyl)-3-[[4-[(4-fluorophenyl)methyl]-1-piperidinyl]methyl]-1-piperidinecarboxamide, (+/−)-N-(3-methoxyphenyl)-3-[[4-[(4-fluorophenyl)methyl]-1-piperidinyl]methyl]-1-piperidinecarboxamide, (+/−)-N-(3-cyanophenyl)-3-[[4-[(4-fluorophenyl)methyl]-1-piperidinyl]ethyl]-1-piperidinecarboxamide, (+/−)-N-(3-carboethoxyphenyl)-3-[[4-[(4-fluorophenyl)methyl]-1-piperidinyl]ethyl]-1-piperidinecarboxamide, (+/−)-N-(4-carboethoxyphenyl)-3-[[4-[(4-fluorophenyl)methyl]-1-piperidinyl]ethyl]-1-piperidinecarboxamide, (+/−)-N-(4-fluorophenyl)-3-[[4-[(4-fluorophenyl)methyl]-1-piperidinyl]ethyl]-1-piperidinecarboxamide, (+/−)-N-(1-adamantylphenyl)-3-[[4-[(4-fluorophenyl)methyl]-1-piperidinyl]ethyl]-1-piperidinecarboxamide,
(+/−)-N-phenyl-3-[[4-[(4-fluorophenyl)methyl]-1-piperidinyl]ethyl]-1-piperidinecarboxamide,
(+/−)-N-(3-methoxyphenyl)-3-[[4-[(4-fluorophenyl)methyl]-1-piperidinyl]ethyl]-1-piperidinecarboxamide,
(+/−)-1-phenylsulfonyl-3-[[4-[(4-fluorophenyl)methyl]-1-piperidinyl]ethyl]-piperidinecarboxamide,
(+/−)-1-benzoyl-3-[[4-[(4-fluorophenyl)methyl]-1-piperidinyl]ethyl]-1-piperidinecarboxamide,
(+/−)-1-benzyloxycarbonyl-3-[[4-[(4-fluorophenyl)methyl]-1-piperidinyl]ethyl]-1-piperidinecarboxamide,
(+/−)-N-phenyl-3-[[4-[(4-fluorophenyl)methyl]-1-piperidinyl]methyl]-1-pyrrolidinecarboxamide,
(+/−)-N-(3-cyanophenyl)-3-[[4-[(4-fluorophenyl)methyl]-1-piperidinyl]methyl]-1-pyrrolidinecarboxamide,
(+/−)-N-(3-methoxyphenyl)-3-[[4-[(4-fluorophenyl)methyl]-1-piperidinyl]methyl]-1-pyrrolidinecarboxamide,
(+/−)-N-(4-fluorophenyl)-3-[[4-[(4-fluorophenyl)methyl]-1-piperidinyl]methyl]-1-piperidinecarboxamide,
(+/−)-N-(3-carboethoxyphenyl)-3-[[4-[(4-fluorophenyl)methyl]1-piperidinyl]methyl]-1-pyrrolidinecarboxamide,
(+/−)-N-(4-carboethoxyphenyl)-3-[[4-[(4-fluorophenyl)methyl]-1-piperidinyl]methyl]-1-pyrrolidinecarboxamide,
(+/−)-N-(1-adamantylphenyl)-3-[[4-[(4-fluorophenyl)methyl]-1-piperidinyl]methyl]-1-pyrrolidinecarboxamide,
(+/−)-N-phenyl-2-[[4-[(4-fluorophenyl)methyl]-1-piperidinyl]ethyl]-1-piperidinecarboxamide,
(+/−)-N-(3-cyanophenyl)-2-[[4-[(4-fluorophenyl)methyl]-1-piperidinyl]ethyl]-1-piperidinecarboxamide,
(+/−)-N-(3-methoxyphenyl)-2-[[4-[(4-fluorophenyl)methyl]-1-piperidinyl]ethyl]-1-piperidinecarboxamide,
(+/−)-N-(4-fluorophenyl)-2-[[4-[(4-fluorophenyl)methyl]-1-piperidinyl]ethyl]-1-piperidinecarboxamide,
(+/−)-N-(3-carboethoxyphenyl)-2-[[4-[(4-fluorophenyl)methyl]-1-piperidinyl]ethyl]-1-piperidinecarboxamide,
(+/−)-N-(4-carboethoxyphenyl)-2-[[4-[(4-fluorophenyl)methyl]-1-piperidinyl]ethyl]-1-piperidinecarboxamide,
(+/−)-N-(1-adamantylphenyl)-2-[[4-[(4-fluorophenyl)methyl]-1-piperidinyl]ethyl]-1-piperidinecarboxamide,
(+/−)-N-phenyl-2-[[4-[(4-fluorophenyl)methyl]-1-piperidinyl]methyl]-1-piperidinecarboxamide,
(+/−)-N-(3-cyanophenyl)-2-[[4-[(4-fluorophenyl)methyl]-1-piperidinyl]methyl]-1-piperidinecarboxamide,
(+/−)-N-(3-methoxyphenyl)-2-[[4-[(4-fluorophenyl)methyl]-1-piperidinyl]methyl]-1-piperidinecarboxamide,
(+/−)-N-(4-fluorophenyl)-2-[[4-[(4-fluorophenyl)methyl]-1-piperidinyl]methyl]-1-piperidinecarboxamide,
(+/−)-N-(3-carboethoxyphenyl)-2-[[4-[(4-fluorophenyl)methyl]-1-piperidinyl]methyl]-1-piperidinecarboxamide,
(+/−)-N-(4-carboethoxyphenyl)-2-[[4-[(4-fluorophenyl)methyl]-1-piperidinyl]methyl]-1-piperidinecarboxamide,
(+/−)-N-(1-adamantylphenyl)-2-[[4-[(4-fluorophenyl)methyl]-1-piperidinyl]methyl]-1-piperidinecarboxamide,
(+/−)-N-(3-cyanophenyl)-2-[[4-[(4-fluorophenyl)methyl]-1-piperidinyl]methyl]-4-morpholinecarboxamide,
(+/−)-N-(3-carboethoxyphenyl)-2-[[4-[(4-fluorophenyl)methyl]-1-piperidinyl]methyl]-4-morpholinecarboxamide,
(+/−)-N-(4-carboethoxyphenyl)-2-[[4-[(4-fluorophenyl)methyl]-1-piperidinyl]methyl]-4-morpholinecarboxamide,
(+/−)-N-(4-fluorophenyl)-2-[[4-[(4-fluorophenyl)methyl]-1-piperidinyl]methyl]-4-morpholinecarboxamide,
(+/−)-N-(1-adamantylphenyl)-2-[[4-[(4-fluorophenyl)methyl]-1-piperidinyl]methyl]-4-morpholinecarboxamide,
(+/−)-N-phenyl-2-[[4-[(4-fluorophenyl)methyl]-1-piperidinyl]methyl]-4-morpholinecarboxamide,
(+/−)-N-(3-methoxyphenyl)-2-[[4-[(4-fluorophenyl)methyl]-1-piperidinyl]methyl]-4-morpholinecarboxamide,
(+/−)-N-(3-cyanophenyl)-3-[[4-[(4-fluorophenyl)methyl]-1-piperidinyl]methyl]-3-hydroxy-1-piperidinecarboxamide,
(+/−)-N-(3-carboethoxyphenyl)-3-[[4-[(4-fluorophenyl)methyl]-1-piperidinyl]methyl]-3-hydroxy-1-piperidinecarboxamide,
(+/−)-N-(4-carboethoxyphenyl)-3-[[4-[(4-fluorophenyl)methyl]-1-piperidinyl]methyl]-3-hydroxy-1-piperidinecarboxamide,
(+/−)-N-(4-fluorophenyl)-3-[[4-[(4-fluorophenyl)methyl]-1-piperidinyl]methyl]-3-hydroxy-1-piperidinecarboxamide,
(+/−)-N-phenyl-3-[[4-[(4-fluorophenyl)methyl]-1-piperidinyl]methyl]-3-hydroxy-1-piperidinecarboxamide,
(+/−)-N-(3-methoxyphenyl)-3-[[4-[(4-fluorophenyl)methyl]-1-piperidinyl]methyl]-3-hydroxy-1-piperidinecarboxamide,
(+/−)-N-(3-cyanophenyl)-3-[[4-[(4-fluorophenyl)methyl]-1-piperidinyl]methyl]-3-phenylmethyl-1-piperidine-carboxamide,
(+/−)-N-(4-fluorophenyl)-3-[[4-[(4-fluorophenyl)methyl]-1-piperidinyl]methyl]-3-phenylmethyl-1-piperidine-carboxamide,
(+/−)-N-phenyl-3-[[4-[(4-fluorophenyl)methyl]-1-piperidinyl]methyl]-3-phenylmethyl-1-piperidinecarboxamide,
(+/−)-N-(3-methoxyphenyl)-3-[[4-[(4-fluorophenyl)methyl]-1-piperidinyl]methyl]-3-phenylmethyl-1-piperidine-carboxamide,
(+/−)-(cis)-N-(3-cyanophenyl)-3-[[4-[(4-fluorophenyl)methyl]-1-piperidinyl]methyl]-2-phenylmethyl-1-piperidine-carboxamide,
(+/−)-(cis)-N-(3-carboethoxyphenyl)-3-[[4-[(4-fluorophenyl)methyl]-1-piperidinyl]methyl]-2-phenylmethyl-1-piperidinecarboxamide,
(+/−)-(cis)-N-(4-carboethoxyphenyl)-3-[[4-[(4-fluorophenyl)methyl]-1-piperidinyl]methyl]-2-phenylmethyl-1-piperidinecarboxamide,
(+/−)-(cis)-N-(4-fluorophenyl)-3-[[4-[(4-fluorophenyl)methyl]-1-piperidinyl]methyl]-2-phenylmethyl-1-piperidine carboxamide,
(+/−)-(cis)-N-phenyl-3-[[4-[(4-fluorophenyl)methyl]-1-piperidinyl]methyl]-2-phenylmethyl-1-piperidine-carboxamide,
(+/−)-(cis)-N-(3-methoxyphenyl)-3-[[4-[(4-fluorophenyl)methyl]-1-piperidinyl]methyl]-2-phenylmethyl-1-piperidinecarboxamide,
(+/−)-(trans)-N-(3-cyanophenyl)-3-[[4-[(4-fluorophenyl)methyl]-1-piperidinyl]methyl]-2-phenylmethyl-1-piperidinecarboxamide,
(+/−)-(trans)-N-(3-carboethoxyphenyl)-3-[[4-((4-fluorophenyl)methyl]-1-piperidinyl]methyl]-2-phenylmethyl-1-piperidinecarboxamide,
(+/−)-(trans)-N-(4-carboethoxyphenyl)-3-[[4-[(4-fluorophenyl)methyl]-1-piperidinyl]methyl]-2-phenylmethyl-1-piperidinecarboxamide,
(+/−)-(trans)-N-(4-fluorophenyl)-3-[[4-[(4-fluorophenyl)methyl]-1-piperidinyl]methyl]-2-phenylmethyl-1-piperidinecarboxamide,
(+/−)-(trans)-N-phenyl-3-[[4-[(4-fluorophenyl)methyl]-1-piperidinyl]methyl]-2-phenylmethyl-1-piperidine carboxamide,
(+/−)-(trans)-N-(3-methoxyphenyl)-3-[[4-[(4-fluorophenyl)methyl]-1-piperidinyl]methyl]-2-phenylmethyl-1-piperidinecarboxamide, (+/−)-(trans)-N-(3-acetylphenyl)-3-[[4-[(4-fluorophenyl)methyl]-1-piperidinyl]methyl]-2-phenylmethyl-1-piperidinecarboxamide, (+/−)-N-(3-cyanophenyl)-3-[[4-[(4-fluorophenyl)methyl]-1-piperidinyl]methyl]-3,4-dihydro-2(1H)isoquinoline-carboxamide, (+/−)-N-(phenyl)-3-[[4-[(4-fluorophenyl)methyl]-1-piperidinyl]methyl]-3,4-dihydro-2(1H) isoquinolinecarboxamide, (+/−)-N-(3-methoxyphenyl)-3-[[4-[(4-fluorophenyl)methyl]-1-piperidinyl]methyl]-3,4-dihydro-2(1H)isoquinoline-carboxamide, (+/−)-3-[[4-[(4-fluorophenyl)methyl]-1-piperidinyl]methyl]-1,2,3,4-tetrahydro-2-(phenylacetyl)isoquinoline, (+/−)-3-[[4-[(4-fluorophenyl)methyl]-1-piperidinyl]methyl]-1,2,3,4-tetrahydro-2-(phenylmethylsulfonyl)isoquinoline, (+/−)-Phenyl-3-[[4-[(4-fluorophenyl)methyl]-1-piperidinyl]methyl]-3,4-dihydro-2(1H) isoquinolinecarboxylate, (+/−)-N-(4-cyanophenyl)-3-[[4-[(4-fluorophenyl)methyl]-1-piperidinyl]methyl]-3,4-dihydro-2(1H) isoquinoline-carboxamide, (+/−)-N-(4-fluorophenyl)-3-[[4-[(4-fluorophenyl)methyl]-1-piperidinyl]methyl]-3,4-dihydro-2(1H)isoquinoline-carboxamide, (+/−)-N-(3-cyanophenyl)-3-[2-[4-[(phenyl)methyl]-1-piperidinyl]ethyl]-3,4-dihydro-2(1H)-isoquinoline-carboxamide, (+/−)-3-[[4-[(phenyl)methyl]-1-piperidinyl]ethyl]-1,2,3,4-tetrahydro-2-(phenylsulfonyl)isoquinoline, (+/−)-N-(4-fluorophenyl)-3-[2-[4-[(phenyl)methyl]-1-piperidinyl]ethyl]-3,4-dihydro-2(1H)-isoquinoline-carboxamide, (+/−)-N-(phenyl)-3-[2-[4-[(phenyl)methyl]-1-piperidinyl]ethyl]-3,4-dihydro-2(1H)-isoquinolinecarboxamide, (+/−)-3-[[4-[(phenyl)methyl]-1-piperidinyl]ethyl]-1,2,3,4-tetrahydro-2-(2-thiophenesulfonyl)isoquinoline, (+/−)-3-[[4-[(phenyl)methyl]-1-piperidinyl]ethyl]-1,2,3,4-tetrahydro-2-(phenacetyl)isoquinoline, (+/−)-N-(3-methoxyphenyl)-3-[2-[4-[(phenyl)methyl]-1-piperidinyl]ethyl]-3,4-dihydro-2(1H)-isoquinoline-carboxamide, (+/−)-N-(phenyl)-3-[2-[4-[(4-fluorophenyl)methyl]-1-piperidinyl]ethyl]-3,4-dihydro-2(1H)-isoquinoline-carboxamide, (+/−)-N-(3-methoxyphenyl)-3-[2-[4-[(4-fluorophenyl)methyl]-1-piperidinyl]ethyl]-3,4-dihydro-2(1H)-isoquinoline-carboxamide, (+/−)-N-(3-cyanophenyl)-3-[2-[4-[(4-fluorophenyl)methyl]-1-piperidinyl]ethyl]-3,4-dihydro-2(1H)-isoquinoline-carboxamide, (+/−)-3-[[4-[(4-fluorophenyl)methyl]-1-piperidinyl]ethyl]-1,2,3,4-tetrahydro-2-(phenylmethylsulfonyl)isoquinoline, (+/−)-Phenyl-3-[2-[4-[(4-fluorophenyl)methyl]-1-piperidinyl]ethyl]-3,4-dihydro-2(1H)-isoquinoline-carboxylate, (+/−)-N-(3-carboethoxyphenyl)-3-[2-[4-[(phenyl)methyl]-1-piperidinyl]ethyl]-3,4-dihydro-2(1H)-isoquinoline-carboxamide, (+/−)-N-(3-carboethoxyphenyl)-3-[2-[4-[(4-fluorophenyl)methyl]-1-piperidinyl]ethyl]-3,4-dihydro-2(1H)-isoquinolinecarboxamide, (+/−)-N-(3-cyanophenyl)-4-[2-[4-(phenylmethyl)-1-piperidinyl]ethyl]-3,4-dihydro-2(1H)-isoquinolinecarboxamide, (+/−)-4-[2-[4-(phenylmethyl)-1-piperidinyl]ethyl]-3,4-dihydro-2(1H)phenylsulfonyl isoquinoline, (+/−)-N-(4-fluorophenyl)-4-[2-[4-(phenylmethyl)-1-piperidinyl]ethyl]-3,4-dihydro-2(1H)-isoquinolinecarboxamide, (+/−)-N-(phenyl)-4-[2-[4-(phenylmethyl)-1-piperidinyl]ethyl]-3,4-dihydro-2(1H)-isoquinolinecarboxamide, (+/−)-N-(3-methoxyphenyl)-4-[2-[4-(phenylmethyl)-1-piperidinyl]ethyl]-3,4-dihydro-2(1H)-isoquinoline-carboxamide, (+/−)-Phenyl-4-[2-[4-(phenylmethyl)-1-piperidinyl]ethyl]-3,4-dihydro-2(1H)-isoquinolinecarboxylate, (+/−)-4-[2-[4-(phenylmethyl)-1-piperidinyl]ethyl]-3,4-dihydro-2(1H)phenacetyl isoquinoline, (+/−)-N-(3-cyanophenyl)-4-[2-[4-(4-fluorophenylmethyl)-1-piperidinyl]ethyl]-3,4-dihydro-2(1H)-isoquinoline-carboxamide, (+/−)-4-[2-[4-(4-fluorophenylmethyl)-1-piperidinyl]ethyl]-3,4-dihydro-2(1H)-[phenyl]sulfonyl isoquinoline, (+/−)-4-[2-[4-(4-fluorophenylmethyl)-1-piperidinyl]ethyl]-3,4-dihydro-2(1H)[phenacetyl]isoquinoline, (+/−)-4-[2-[4-(4-fluorophenylmethyl)-1-piperidinyl]ethyl]-3,4-dihydro-2(1H)-[phenylmethyl]sulfonylisoquinoline, (+/−)-N-(4-carbethoxyphenyl)-4-[2-[4-(4-fluorophenylmethyl)-1-piperidinyl]ethyl]-3,4-dihydro-2(1H)-isoquinoline-carboxamide, (+/−)-N-(4-fluorophenyl)-4-[2-[4-(phenylmethyl)-1-piperidinyl]ethyl]-3,4-dihydro-2(1H)-isoquinolinecarboxamide, (2R)-2-{[4-(4-fluorobenzyl)-1-piperidinyl]methyl}-4-[(2R)-3,3,3-trifluoro-2-methoxy-2-phenylpropanoyl] morpholine, (2R)-N-(3-acetylphenyl)-2-{[4-(4-fluorobenzyl)-1-piperidinyl]methyl}-4-morpholinecarboxamide, (2R)-2-{[4-(4-fluorobenzyl)-1-piperidinyl]methyl}-N-(3-methoxyphenyl)-4-morpholinecarboxamide, (2R)-N-(3-cyanophenyl)-2-{[4-(4-fluorobenzyl)-1-piperidinyl]methyl}-4-morpholinecarboxamide, (2R)-2-{[4-(4-fluorobenzyl)-1-piperidinyl]methyl}-N-(4-fluorophenyl)-4-morpholinecarboxamide, (2R)-2-{[4-(4-fluorobenzyl)-1-piperidinyl]methyl}-N-phenyl-4-morpholinecarboxamide, (2R)-N-(3-cyanophenyl)-2-{[(3S)-3-(4-fluorobenzyl)piperidinyl]methyl}-4-morpholinecarboxamide, (2R)-N-(3-acetylphenyl)-2-{[(3S)-3-(4-fluorobenzyl)piperidinyl]methyl}-4-morpholinecarboxamide, (2R)-N-(3-acetylphenyl)-2-{[(3S)-3-(4-fluorobenzyl)piperidinyl]methyl}-N-phenyl-4-morpholinecarboxamide, 3-{[3-(4-fluorobenzyl)-1-pyrrolidinyl]methyl}-N-phenyl-1-piperidinecarboxamide, N-(3-cyanophenyl)-3-{[3-(4-fluorobenzyl)-1-pyrrolidinyl]methyl}-1-piperidinecarboxamide, N-(3-acetylphenyl)-3-{[3-(4-fluorobenzyl)-1-pyrrolidinyl]methyl}-1-piperidinecarboxamide, 3-{[(3S)-3-(4-fluorobenzyl)piperidinyl]methyl}-N-phenyl-1-piperidinecarboxamide, N-(3-cyanophenyl)-3-{[(3S)-3-(4-fluorobenzyl)piperidinyl]methyl}-1-piperidinecarboxamide, N-(3-acetylphenyl)-3-{[(3S)-3-(4-fluorobenzyl)piperidinyl]methyl}-1-piperidinecarboxamide, tert-butyl 4-[(3-cyanoanilino)carbonyl]-2-{[4-(4-fluorobenzyl)-1-piperidinyl]methyl}-1-piperazinecarboxylate, N-(3-cyanophenyl)-3-{[4-(4-fluorobenzyl)-1-piperidinyl]methyl}-1-piperazinecarboxamide dihydrochloride, 4-benzyl-N-(3-cyanophenyl)-3-{[4-(4-fluorobenzyl)-1-piperidinyl]methyl}-1-piperazinecarboxamide, 4-acetyl-N-(3-acetylphenyl)-3-{[4-(4-fluorobenzyl)-1-piperidinyl]methyl}-1-piperazinecarboxamide, tert-butyl 4-[(anilino)carbonyl]-2-{[4-(4-fluorobenzyl)-1-piperidinyl]methyl}-1-piperazinecarboxylate,
tert-butyl 4-[(3-methoxyanilino)carbonyl]-2-{[4-(4-fluorobenzyl)-1-piperidinyl]methyl}-1-piperazinecarboxylate,
tert-butyl 4-[(3-acetylanilino)carbonyl]-2-{[4-(4-fluorobenzyl)-1-piperidinyl]methyl}-1-piperazine carboxylate,
3-{[4-(4-fluorobenzyl)-1-piperidinyl]methyl}-N-phenyl-1-piperazinecarboxamide dihydrochloride,
3-{[4-(4-fluorobenzyl)-1-piperidinyl]methyl}-N-(3-methoxyphenyl)-1-piperazinecarboxamide dihydrochloride
N-(3-acetylphenyl)-3-{[4-(4-fluorobenzyl)-1-piperidinyl]methyl}-1-piperazinecarboxamide dihydrochloride; and
4-benzyl-N-(3-cyanophenyl)-3-{[4-(4-fluorobenzyl)-1-piperidinyl]methyl}-1-piperazinecarboxamide.

[56] In another embodiment, the present invention provides a pharmaceutical composition, comprising a pharmaceutically acceptable carrier and a therapeutically effective amount of a compound of the present invention.

[57] In another embodiment, the present invention provides a method for modulation of chemokine receptor activity comprising administering to a patient in need thereof a therapeutically effective amount of a compound of the present invention.

[58] In another embodiment, the present invention provides a method for treating or preventing inflammatory disorders, such as, but not limited to, allergic disorders, comprising administering to a patient in need thereof a therapeutically effective amount of a compound of the present invention.

[59] In another embodiment, the present invention provides a method for treating or preventing disorders selected from asthma, allergic rhinitis, atopic dermatitis, inflammatory bowel diseases, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, HIV infection, cystic fibrosis, Churg-Strauss syndrome, lymphoma, Hodgkin's disease, and colonic carcinoma.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

When any variable (e.g., $R^a$) occurs more than one time in any constituent or formula for a compound, its definition at each occurrence is independent of its definition at every other occurrence. Thus, for example, if a group is shown to be substituted with 0–2 $R^a$, then said group may optionally be substituted with up to two $R^a$ groups and $R^a$ at each occurrence is selected independently from the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-8}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl; "Alkenyl" is intended to include hydrocarbon chains of either a straight or branched configuration and one or more unsaturated carbon-carbon bonds which may occur in any stable point along the chain, such as ethenyl, propenyl, and the like. "Alkynyl" is intended to include hydrocarbon chains of either a straight or branched configuration and one or more unsaturated triple carbon-carbon bonds which may occur in any stable point along the chain, such as ethynyl, propynyl, and the like. "$C_{3-6}$ cycloalkyl" is intended to include saturated ring groups having the specified number of carbon atoms in the ring, including mono-, bi-, or poly-cyclic ring systems, such as cyclopropyl, cyclobutyl, cyclopentyl, cyclohexyl, and cycloheptl in the case of $C_7$ cycloalkyl.

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

The compounds of Formula I can also be quaternized by standard techniques such as alkylation of the piperidine or pyrrolidine with an alkyl halide to yield quaternary piperidinium salt products of Formula I. Such quaternary piperidinium salts would include a counterion. As used herein, "counterion" is used to represent a small, negatively charged species such as chloride, bromide, hydroxide, acetate, sulfate, and the like.

As used herein, "carbocycle" or "carbocyclic residue" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl,; [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5- to 7- membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyi, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. Preferred heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like. Preferred prodrugs are amine prodrugs the amine group is attached to a group selected from OH, $C_{1-4}$ alkoxy, $C_{6-10}$ aryloxy, $C_{1-4}$ alkoxycarbonyl, $C_{6-10}$ aryloxycarbonyl, $C_{6-10}$ arylmethylcarbonyl, $C_{1-4}$ alkylcarbonyloxy $C_{1-4}$ alkoxycarbonyl, and $C_{6-10}$ arylcarbonyloxy $C_{1-4}$ alkoxycarbonyl. More preferred prodrugs are OH, methoxy, ethoxy, benzyloxycarbonyl, methoxycarbonyl, and methylcarbonyloxymethoxycarbonyl.

"Stable compound" and "stable structure" are meant to indicate a compound that is sufficiently robust to survive isolation to a useful degree of purity from a reaction mixture, and formulation into an efficacious therapeutic agent.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are incorporated in their entirety by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the edict molecule must be compatible with the reagents and reactions proposed. Not all compounds of Formula I falling into a given class may be compatible with some of the reaction conditions required in some of the methods described. Such restrictions to the substituents which are compatible with the reaction conditions will be readily apparent to one skilled in the art and alternate methods must be used.

SCHEME 1

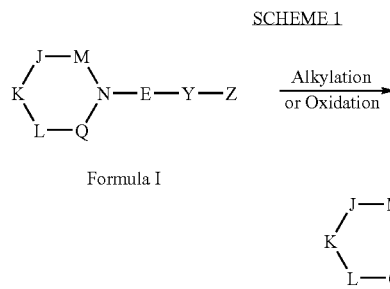

Compounds of Formula I, wherein R4 is present as defined by the scope, may be prepared by procedures depicted in Scheme 1 from compounds of Formula I in which R4 is absent. The quaternary salts of Formula I can be synthesized by alkylation with an alkylhalide such as methyl iodide, benzyl bromide, bromoacetate, etc. in a suitable solvent such as THF, DMF, DMSO, etc. at room temperature to reflux temperature of the solvent. The N-oxides of Formula I can be made by the general protocols of Deady, *Syn. Comm.* 1977, 7, 509 and references therein, with minor modification depending on the substitution of Formula I which should be readily recognized by one skilled in the art. The N-oxides are created by oxidation with mCPBA in an inert solvent such as methlene chloride.

SCHEME 2

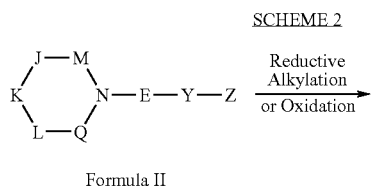

-continued

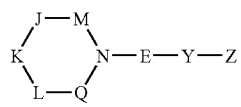

Formula I

Compounds of Formula I, wherein Z is CR'R'R3, may be prepared by procedures depicted in Scheme 2. Reductive alkylation of Formula II, whose preparations are described later, with an aldehyde or ketone is carried out under conditions known in the art, for example, catalytic hydrogenation with hydrogen in the presence of palladium or platinum or with reducing agents such as sodium triacetoxyborohydride. Alternatively, a similar transformation can be accomplished with an alkylating agent ZX where X is a halide (halide=Cl, Br, I), mesylate, tosylate, triflate, etc. in the presence of a base such as triethylamine, pyridine, etc. in acetonitrile, DMF, DMSO, etc. at room temperature to reflux temperature of the solvent.

SCHEME 3

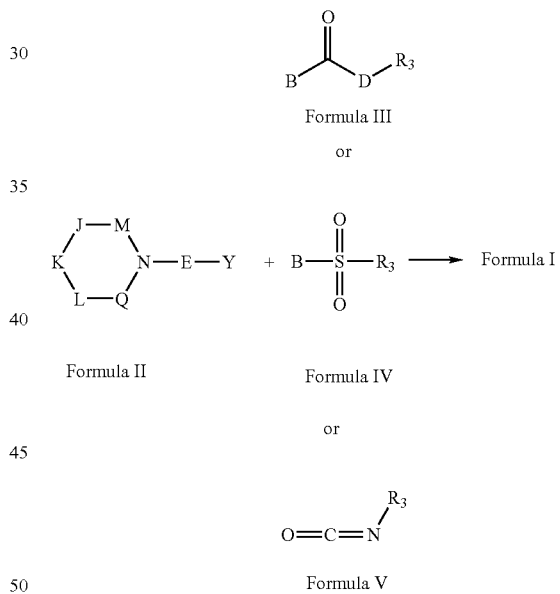

Compounds of Formula I, wherein Z is either COR3, $CO_2R3$, CONR2R3, or $SO_2R3$, may be prepared as shown in Scheme 2. Compounds in which D is a bond, O or NR2 may be synthesized by reacting Formula II with Formula III, wherein B is a good leaving such as but not limited to Cl, Br, or imidazole, in the presence of a base such as, but not limited to, triethylamine or pyridine. Alternatively, Formula II may be reacted with an isocyante of Formula V to provide compounds of Formula I where Z is CONHR3. Alternatively, Formula II may be reacted Formula IV, wherein B is a good leaving such as but not limited to Cl, Br, or imidazole, in the presence of a base such as, but not limited to, triethylamine or pyridine to provide compounds of Formula I where Y is $SO_2R3$.

SCHEME 4

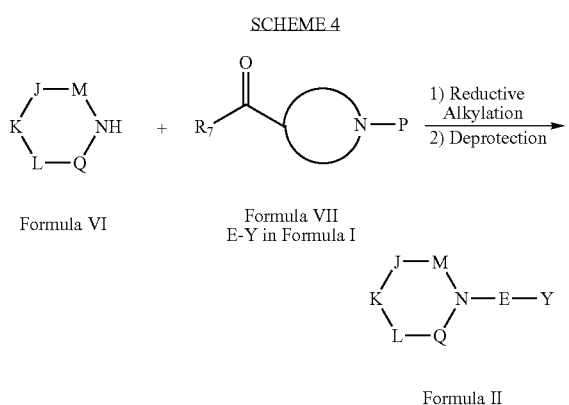

Formula VI

Formula VII
E-Y in Formula I

Formula II

Preparation of intermediates of Formula II are depicted in Scheme 4. Reductive alkylation of the intermediates of Formula VI, whose preparations are described later if not commercially available, are reacted with compounds of Formula VII, whose preparations are described later if not commercially available, wherein amine on Y is protected with an amine protecting group (P) well familiar to those skilled in the art, and typical examples may be found in Greene, T and Wuts, P. G. M., *Protecting Groups in Organic Synthesis*, John Wiley & Sons, Inc., New York, N.Y., 1991 and references therein, is carried out under conditions known in the art, for example catalytic hydrogenation with hydrogen in the presence of palladium or platinum or with reducing agents such as sodium triacetoxyborohydride. The protecting group P is removed using the appropriate reagents, well familiar to those skilled in the art, and typical examples may be found in Greene, T and Wuts, P. G. M., *Protecting Groups in Organic Synthesis*, John Wiley & Sons, Inc., New York, N.Y., 1991, which provides the intermediates of Formula II. Alternatively, compounds of Formula II can be made by alkylating Formula VI with compounds of Formula VIII, as seen in Scheme 5, where the alcohol has been convert to a leaving group such as mesylate, tosylate, triflate, etc. by conditions well familiar to one skilled in the art.

The synthesis of the substituted and unsubstituted pyrrolidines, piperidines, piperazines, and morpholines of Formula VI and VII may be achieved by methods known in the art and are illustrated in the following schemes.

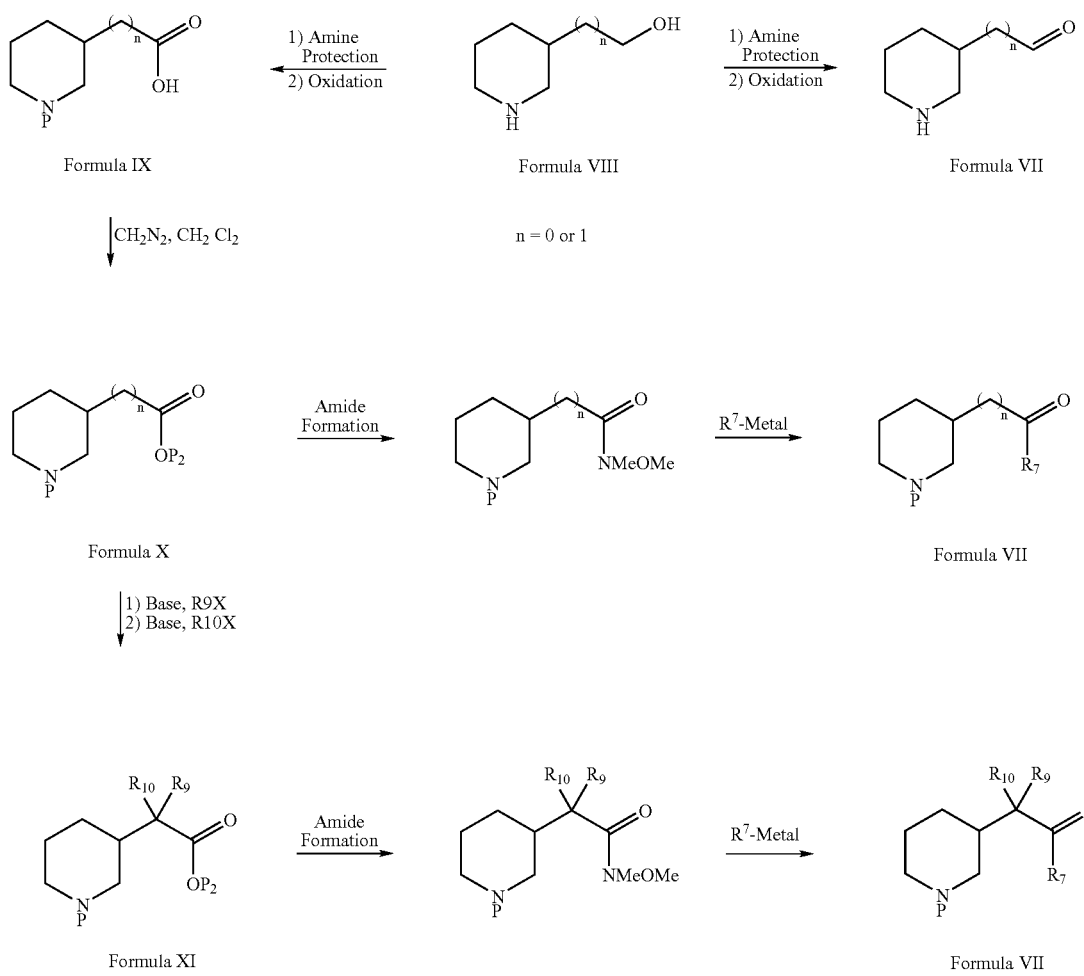

The monosubstituted pyrrolidines and piperidines of Formula VII may be synthesized by procedures depicted in Scheme 5. It is understood that the chemistry is shown for only one position on the piperidine ring and that similar transformations may be preformed on other ring positions for both piperidine and pyrrolidine. The amino group of Formula VIII can be reacted with the appropriate reagents to protect the amine functionality, typical examples may be found in Greene, T and Wuts, P. G. M. The alcohol can be oxidized to either an aldehyde of Formula VII or an acid of Formula IX for further elaboration as shown in Scheme 5. Examples of oxidizing agents and conditions for aldehyde or acid formation are well familiar to those skilled in the art and typical examples may be found in Richard C. Larock, Comprehensive Organic Transformations, VCH Publishers, New York, 1989 and references therein. The acid of Formula IX can be converted to the methyl ester of Formula X with diazomethane in a inert solvent such as ether, THF, etc. at room temperature. The methyl ester can be treated with methyoxymethylamine precomplexed with trimethylaluminum to yield the Weinreb amide, as described in Taschner and Cyr, *Tetrahedron Lett.* 1990, 31, 5297 and references therein which than can be treated R7-M where M is a metal such as lithium, magnesium, etc. in an inert solvent such as THF, ether, etc. at −78° C. to room temperature to yield compounds of Formula VII. Alternatively, when n=1 then the methyl ester can be treated with a base such as LDA, KHMDS, LHMDS, etc. in THF, ether, dioxane, etc., at −78° C. to room temperature and an alkylating agent R9X where X is a halide, mesylate, triflate, etc. to yield compounds of Formula XI. This process can be repeated to incorporate R10 if necessary. Compounds of Formula XI can be convert to compounds of Formula VII as by methods described above.

SCHEME 6

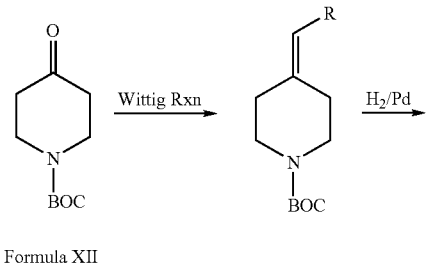

Formula XII

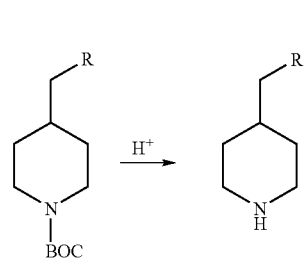

Formula VI

The monosubstituted pyrrolidines and piperidines of Formula VI may be synthesized by procedures depicted in Scheme 6. It is understood that the chemistry is shown for only one position on the piperidine ring and that similar transformations may be preformed on other ring positions for both piperidine and pyrrolidine. Formula XII can be treated under Wittig reaction conditions followed by reduction and deprotection under acidic conditions to yield compounds of Formula VI employing reactions well familiar to those skilled in the art. Alternatively, compounds of Formula VII can be used in place of Formula XII to create further embodiments of compounds of Formula VI.

SCHEME 7

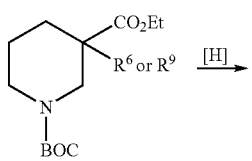

Formula XIII

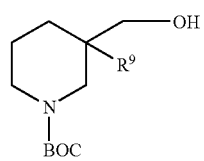

Formula VIII

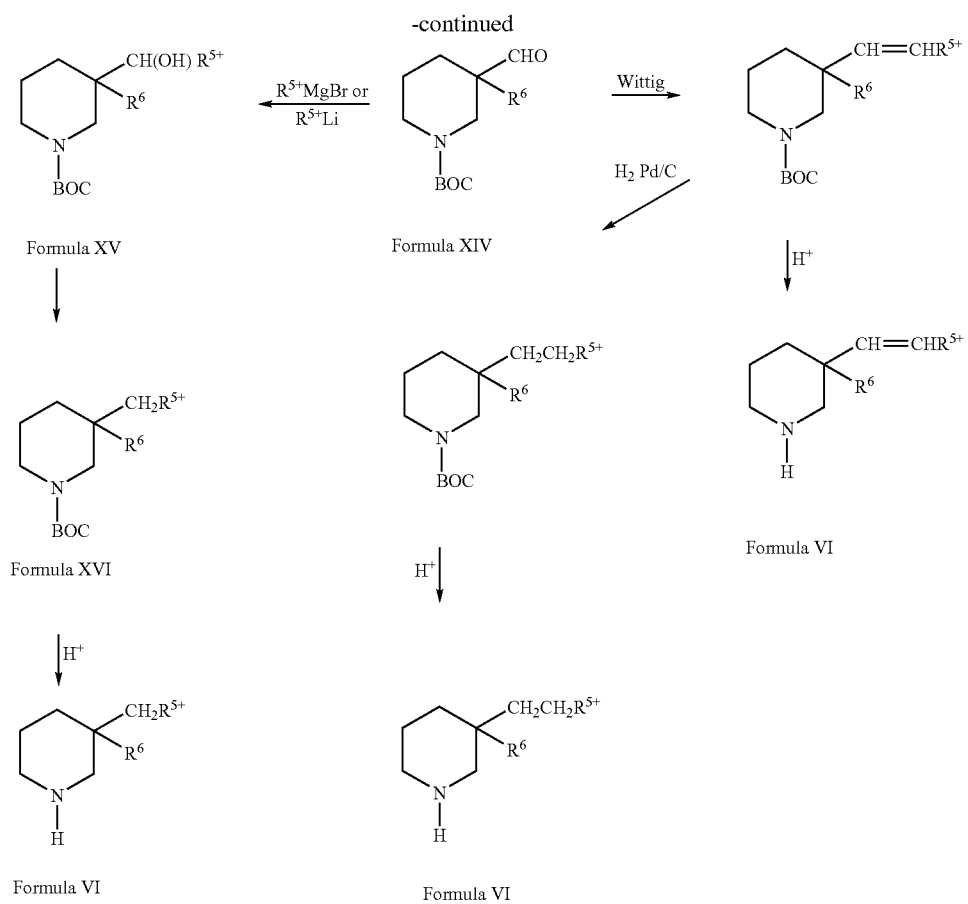

The gem-disubstituted pyrrolidines and piperidines of Formula VI and VIII may be synthesized by procedures depicted in Scheme 7. It is understood by one skilled in the art that some of the steps in this scheme can be rearranged. It is also understood that gem-disubstitution is only shown for only one position on the piperidine ring and that similar transformations may be performed on other carbon atoms as well, both for piperidine and pyrrolidine. Thus, BOC-3-carboethoxypiperidine may be alkylated employing a base such as LDA, KHMDS, LHDMS, etc., in THF, ether, dioxane, etc. at −78° C. to room temperature and an alkylating agent $R^6X$ or $R^9X$ where X is a halide (halide=Cl, Br, I), mesylate, tosylate, triflate, etc. to yield Formula XIII. Reduction using DIBAL, for example, leads to compounds of Formula VIII which can be further elaborated into compounds of Formula VII as described in Scheme 5. Alternatively, reduction using DIBAL, for example, followed by oxidation such as a Swern oxidation (S. L. Huang, K. Omura, D. Swern J. Org. Chem. 1976, 41, 3329–32) yields Formula XIV. Wittig olefination followed by acidic deprotection yields compounds of Formula VI. Alternatively, reduction of the Wittig adduct with $H_2$ which may be deprotected under acidic conditions to yield compounds of Formula VI. Alternatively, reaction of Formula XIV with an alkyllithium or Grignard reagent yields Formula XV which may be reduced catalytically or with $Et_3SiH/TFA$ (J. Org. Chem. 1969, 34, 4; J. Org. Chem. 1987, 52, 2226) if $R^{5*}$ ($R^{5*}=R^5$ or a precursor thereof) is aromatic to yield Formula XVI. If $R^{5*}$ is not aromatic, then the OH may be reduced by the method of Barton (Barton, D. H. R.; Jaszberenyi, J. C. Tet. Lett. 1989, 30, 2619 and other references therein). Once tosylated, the alcohol can also be displaced with dialkyllithium cuprates (not shown) (Hanessian, S.; Thavonekham, B.; DeHoff, B.; J Org. Chem. 1989, 54, 5831). Acidic deprotection yields compounds of Formula VI.

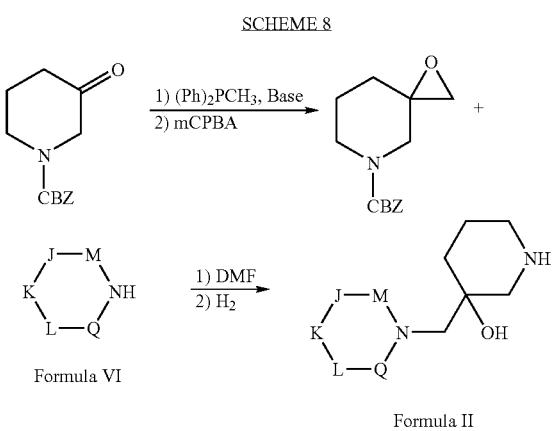

The gem-disubstituted pyrrolidines and piperidines in which R9 is a hydroxy group may also be synthesized by procedures depicted in Scheme 8. It is understood that gem-disubstitution is only shown for only one position on the piperidine ring and that similar transformations may be performed on other carbon atoms as well, both for piperidine and pyrrolidine. CBZ-3-piperidone can be treated under Wittig reaction conditions well familiar to those skilled in the art to yield alkene compounds which then can be treated with mCPBA in an inert solvent such as methylene chloride to yield Formula VII. The epoxide can then be opened with compounds of Formula VI in solvents such as acetonitrile, DMF, DMSO, etc. at room temperature to reflux temperature of the solvent with pyrrolidine in toluene, THF, ether, dioxane, etc. at room temperature to the reflux temperature. The protecting group can be removed under conditions known in the art, for example catalytic hydrogenation with hydrogen in the presence of palladium or platinum to yield compounds of Formula II.

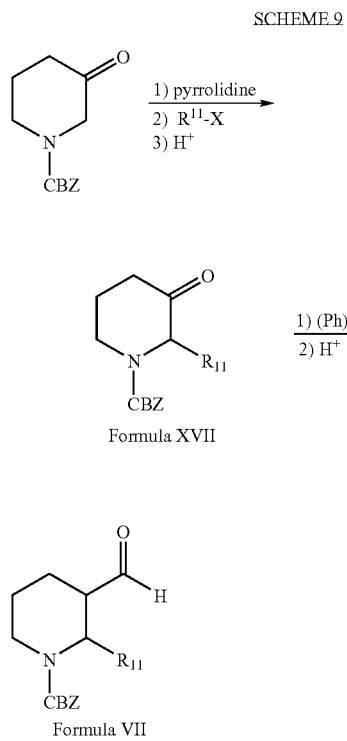

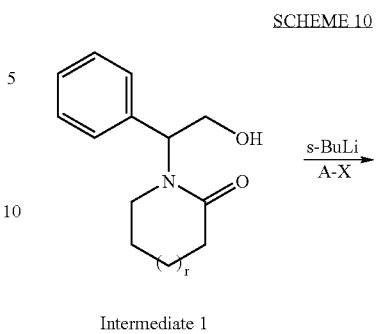

Intermediate 1

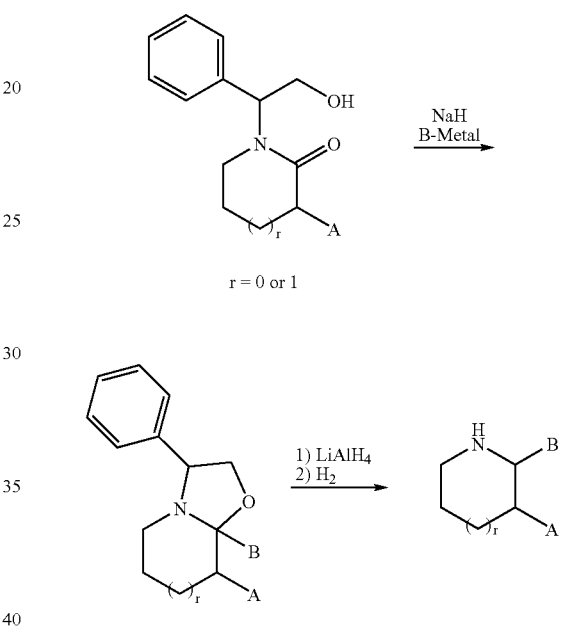

The 2,3-disubstituted pyrrolidines and piperidines of Formula VII may be synthesized as shown in Scheme 9. This procedure essentially follows the general protocols of Brubaker and Colley, *J. Med. Chem.* 1986, 29, 1528 and references therein, with minor modification depending R11 which should be readily recognized by one skilled in the art. CBZ-3-piperidone can be treated with pyrrolidine in toluene, THF, ether, dioxane, etc. at room temperature to the reflux temperature of the solvent followed by an alkylating agent R11-X where X is a halide, mesylate, triflate, etc. in THF, acetonitrile, dioxane, etc. at room temperature to the reflux temperature of the solvent and then treated to acidic hydrolysis conditions to yield compounds of Formula XVII. Formula XVII can then be treated under Wittig reaction conditions well familiar to those skilled in the art followed by acid treatment to yield compounds of Formula VII.

The 2,3-disubstituted pyrrolidines and piperidines of Formula VI and VIII may also be synthesized as shown in Scheme 10. This procedure essentially follows the general protocols of Micouin et. al., *Tetrahedron Lett.* 1996, 37, 849 and references therein, with minor modification depending on A and B which should be readily recognized by one skilled in the art. For compounds of the general Formula VI, Intermediate 1 can be treated with a base such as s-BuLi, etc. and an alkylating agent A-X where X is a halide (halide=Cl, Br, I), mesylate, tosylate, triflate, etc. to incorporate R5, as defined in the scope. The compound can be treated with sodium hydride followed by B-metal which can a grinard reagent to incorporate the B group, R13 as defined in the scope. The synthesis is finished by the reduction of the lactam to the amine with a reagent such as, but not limited to, LAH and then removal of the benzyl group from the amine by procedures well familiar to those skilled in the art such as, but not limited to, hydrogenation. Compounds of Formula VIII in which A is hydroxyethyl or hydroxymethyl and B is R11 as defined in the scope or in which B is hydroxyethyl or hydroxymethyl and A is R9 as defined in the scope are produced with the same protocol with minor modification which should be readily recognized by one skilled in the art.

SCHEME 11

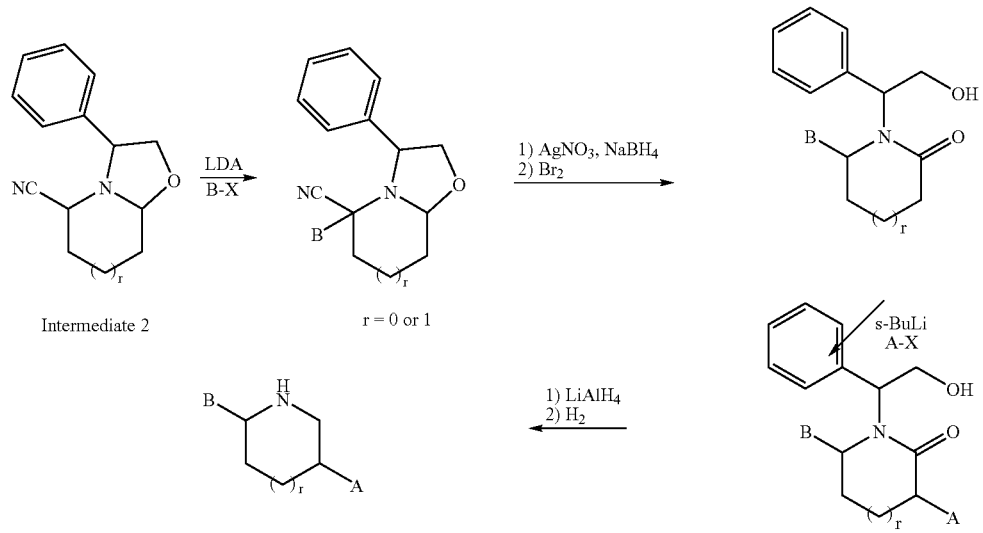

Intermediate 2    r = 0 or 1

The 2,4-disubstituted pyrrolidines and 2,5-disubstituted piperidines of Formula VI and VIII may be synthesized as shown in Scheme 11. This procedure essentially follows the general protocols of Varea et. al., *Tetrahedron Lett.* 1995, 36, 1038 and references therein, with minor modification depending on A and B which should be readily recognized by one skilled in the art. For compounds of the general Formula VI, Intermediate 2 can be treated with a base such LDA, etc. and an alkylating agent B-X where X is a halide (halide=Cl, Br, I), mesylate, tosylate, triflate, etc. to incorporate R13, as defined in the scope. The cyano group of the intermediates can be removed with reagents such as, but not limited to, silver nitrite and sodium borohydride and the intermediates can then be oxidized with reagents such as, but not limited to, bromine. The intermediate can be treated with a base such as s-BuLi, etc. and an alkylating agent A-X where X is a halide (halide=Cl, Br, I), mesylate, tosylate, triflate, etc. to incorporate R5, as defined in the scope. The synthesis is finished by the reduction of the lactam to the amine with a reagent such as, but not limited to, LAH and then removal of the benzyl group from the amine by procedures well familiar to those skilled in the art such as, but not limited to, hydrogenation. Compounds of Formula VIII in which A is hydroxyethyl or hydroxymethyl and B is R11 as defined in the scope or in which B is hydroxyethyl or hydroxymethyl and A is R9 as defined in the scope are produced with the same protocol with minor modification which should be readily recognized by one skilled in the art.

SCHEME 12

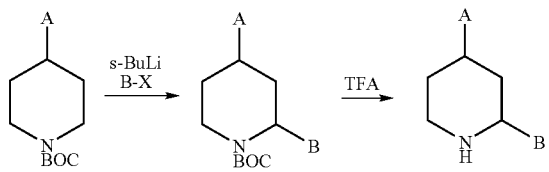

The 2,4-disubstituted piperidines of Formula VI and VIII may be synthesized as shown in Scheme 12. This procedure essentially follows the general protocols of Beak and Lee, *J. Org. Chem.* 1990, 55, 2578 and references therein, with minor modification depending on A and B which should be readily recognized by one skilled in the art. For compounds of the general Formula VI, 4-monosubstituted piperidines, synthesized as described above in Scheme 6 with A, which is R5 as defined in the scope, can be treated with a base such as s-BuLi, etc. and an alkylating agent B-X where X is a halide (halide=Cl, Br, I), mesylate, tosylate, triflate, etc. to incorporate R13, as defined in the scope. The BOC group was removed with reagents such as, but not limited to, TFA. Compounds of Formula VIII in which A is hydroxyethyl or hydroxymethyl and B is R11 as defined in the scope or in which B is hydroxyethyl or hydroxymethyl and A is R9 as defined in the scope are produced with the same protocol with minor modification which should be readily recognized by one skilled in the art.

SCHEME 13

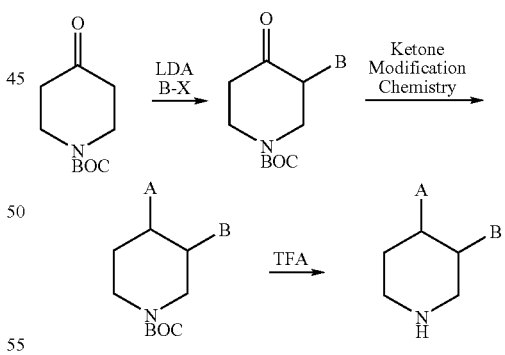

The 3,4-disubstituted piperidines of Formula VI and VII may be synthesized as shown in Scheme 8. For compounds of the general Formula VI, Intermediate 3 can be treated with a base such LDA, etc. and an alkylating agent B-X where X is a halide (halide=Cl, Br, I), mesylate, tosylate, triflate, etc. to incorporate R6, as defined in the scope. The ketone may be modified to incorporate A, which is R5 as defined in the scope, by standard chemistry as described above in Scheme 6. Compounds of Formula VIII in which A is hydroxyethyl or hydroxymethyl and B is R9 as defined in the scope or in which B is hydroxyethyl or hydroxymethyl and A is R9 as defined in the scope are produced with the same protocol with minor modification which should be readily recognized by one skilled in the art.

SCHEME 14

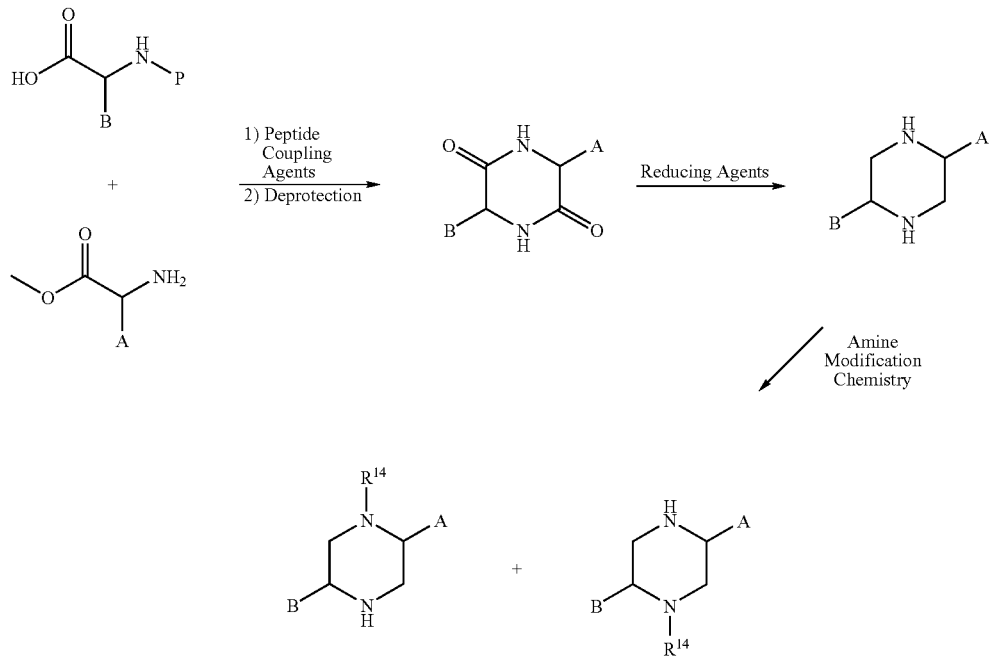

The 2-monosubstituted piperazines, wherein B is H, and 2,5-disubstituted piperazines of Formula VIII may be synthesized as shown in Scheme 14. This procedure essentially follows the general protocols of Yonezawa et. al., *Heterocycles* 1997, 45, 1151 and references therein, with minor modification depending on A and B which should be readily recognized by one skilled in the art. Two amino acid derivatives are coupled by standard peptide coupling chemistry, well familiar to those skilled in the art and typical examples may be found in Richard C. Larock, Comprehensive Organic Transformations. The intermediate is reduced with reducing agents such as, but not limited to, LAH. The intermediate can be treated to amine modification conditions, as described previously in Schemes 2 and 3, to incorporate R14. Compounds of Formula VIII in which A is hydroxyethyl or hydroxymethyl and B is R11 as defined in the scope or in which B is hydroxyethyl or hydroxymethyl and A is R11 as defined in the scope are produced with the same protocol with minor modification which should be readily recognized by one skilled in the art.

SCHEME 15

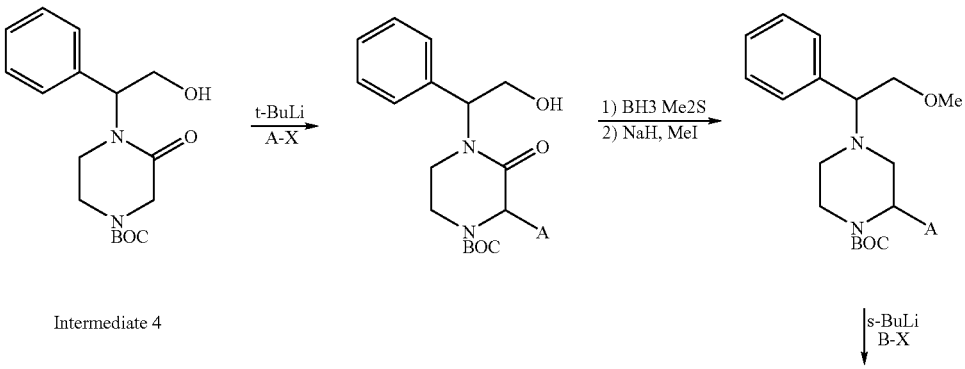

Intermediate 4

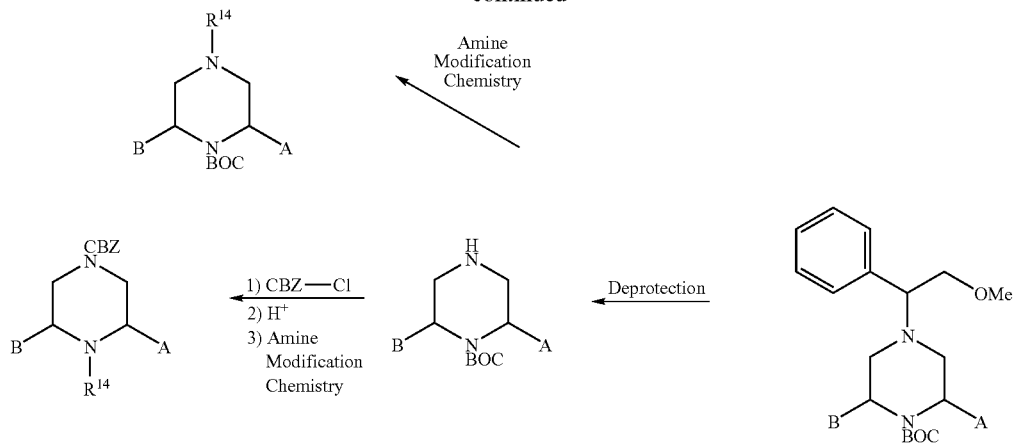

The 2,6-disubstituted piperazines of Formula VIII may be synthesized as shown in Scheme 15. This procedure essentially follows the general protocols of Schanen et. al., *Synthesis* 1996, 833 and references therein, with minor modification depending on A and B which should be readily recognized by one skilled in the art. Intermediate 4 can be treated with a base such as t-BuLi, etc. and an alkylating agent A-X where X is a halide (halide=Cl, Br, I), mesylate, tosylate, triflate, etc. to incorporate A. The amide is reduced with reagents such as, but not limited to, borane. The alcohol is alkylated with reagents such as, but not limited to, sodium hydride and methyl iodine. The intermediate can be treated with a base such as s-BuLi, etc. and an alkylating agent B-X where X is a halide (halide=Cl, Br, I), mesylate, tosylate, triflate, etc. to incorporate B. The benzyl group can be removed from the amine by procedures well familiar to those skilled in the art such as, but not limited to, hydrogenation. The unprotected amine can be treated to amine modification conditions, as described previously in Schemes 2 and 3, to incorporate R14. Alternatively, The unprotected amine can be treated with CBZ-Cl and then the BOC group can be removed and the other amine can be treated to amine modification conditions, as described previously in Schemes 2 and 3, to incorporate R14. Compounds of Formula VIII in which A is hydroxyethyl or hydroxymethyl and B is R11 as defined in the scope or in which B is hydroxyethyl or hydroxymethyl and A is R11 as defined in the scope are produced with the same protocol with minor modification which should be readily recognized by one skilled in the art.

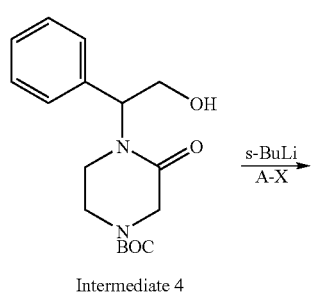

Intermediate 4

The 2,3-disubstituted piperazines of Formula VIII may be synthesized as shown in Scheme 5. This procedure essentially follows the general protocols of Micouin et. al., *Tetrahedron Lett.* 1996, 37, 849 and references therein, with minor modification depending on A and B which should be readily recognized by one skilled in the art. Intermediate 4 can be treated with a base such as s-BuLi, etc. and an alkylating agent A-X where X is a halide (halide=Cl, Br, I), mesylate, tosylate, triflate, etc. to incorporate A. The compound can be treated with sodium hydride followed by B-metal which can a grinard reagent to incorporate the B group. The lactam can be reduced to the amine with a reagent such as, but not limited to, LAH and then removal of the benzyl group from the amine by procedures well familiar to those skilled in the art such as, but not limited to, hydrogenation. The unprotected amine can be treated to amine modification conditions, as described previously in Schemes 2 and 3, to incorporate R14. Alternatively, The unprotected amine can be treated with CBZ-Cl and then the BOC group can be removed and the other amine can be treated to amine modification conditions, as described previously in Schemes 2 and 3, to incorporate R14. Compounds of Formula VIII in which A is hydroxyethyl or hydroxymethyl and B is R11 as defined in the scope or in which B is hydroxyethyl or hydroxymethyl and A is R11 as defined in the scope are produced with the same protocol with minor modification which should be readily recognized by one skilled in the art.

SCHEME 17

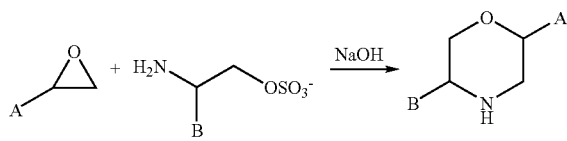

The 2-monosubstituted morpholines, wherein B is H, 3-monosubstituted morpholines, wherein A is H, and 2,5-disubstituted morpholines of Formula VIII may be synthesized as shown in Scheme 17. This procedure essentially follows the general protocols of Brown et. al., *J. Pharm Pharmacol* 1990, 42, 797 and references therein, with minor modification depending on A and B which should be readily recognized by one skilled in the art. Compounds of general Formula VIII are synthesized by treating epoxides with sulfated amino alcohols under basic conditions such as, but not limited to, sodium hydroxide in methanol. Compounds of Formula VIII in which A is hydroxyethyl or hydroxymethyl and B is R11 as defined in the scope or in which B is hydroxyethyl or hydroxymethyl and A is R11 as defined in the scope are produced with the same protocol with minor modification which should be readily recognized by one skilled in the art.

SCHEME 18

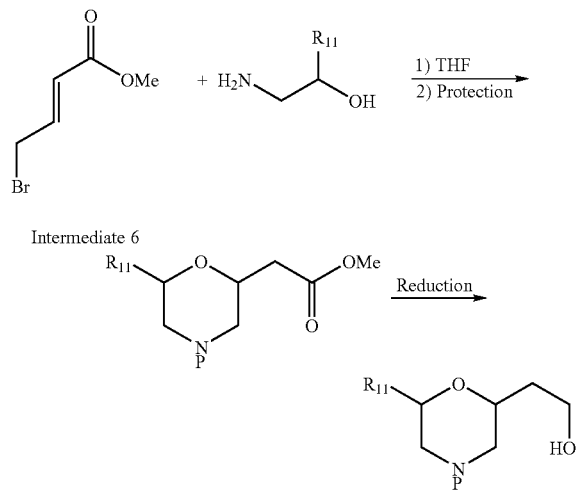

2,6-disubstituted morpholines of Formula VIII may be synthesized as shown in Scheme 18. This procedure essentially follows the general protocols of Colucci et. al., *J. Am. Chem. Soc.* 1987, 109, 7915 and references therein, with minor modification depending on R11 which should be readily recognized by one skilled in the art. Compounds of general Formula VIII are synthesized by treating intermediate 6 with amino alcohols, with R11 as defined in the scope. The amino group is protected with an appropriate protecting group well familiar to those skilled in the art, and typical examples may be found in Greene, T and Wuts, P. G. M., *Protecting Groups in Organic Synthesis*, John Wiley & Sons, Inc., New York, N.Y., 1991 and references therein. The ester functionality is reduced to the alcohol functionality by methods well familiar to those skilled in the art, and typical examples may be found in Richard C. Larock, Comprehensive Organic Transformations.

The compounds of this invention and their preparation can be understood further by the following working examples, which do not constitute a limitation of the invention.

EXAMPLES

Example 1

Preparation of (+/−)-N-phenyl-2-[[4-[(4-fluorophenyl)methyl]-1-piperidinyl]methyl]-1-piperidinecarboxamide Step A. Preparation of N-(t-butoxycarbonyl)-4-(4-fluorophenylmethalene)piperidine.

To a stirring solution of 4-fluorobenzyl-triphenylphosphonium chloride (61.3 g, 150.6 mmol, Fluka) in dry THF (500 mL) was added a 1M solution of potassium t-butoxide (138 mL). The reaction was stirred for 5 min and then a solution of N-(t-butoxycarbonyl)-4-piperidone (25 g, 125.5 mmol) in dry THF (100 mL) was added. After 10 min, the reaction was warmed to reflux for 16 h. After cooling to room temperature, the reaction was conc. in vacuo to an oil. The oil was dissolved in EtOAc and hexanes was added to form a white precipatate. The precipatate was filtered off and the filtrate conc. in vacuo to an oil. The oil was purified by flash chromatography (SiO2, 0–35% EtOAc in hexanes) to yield 27 grams (74%) of the product as a white solid. MS (ESI) 314 (M+Na).

Step B. Preparation of N-(t-butoxycarbonyl)-4-(4-fluorophenylmethyl)piperidine.

To a stirring solution of of N-(t-butoxycarbonyl)-4-(4-fluorophenylmethalene)piperidine (27 g, 92.7 mmol) and 10% palladium on carbon (5.4 g, Aldrich) in MeOH (400 mL) was added 50 psi of hydrogen. The reaction was stirred for 3 h. The reaction was filtered thru celite and the filtrate was conc. in vacuo to yield 23.9 g of a colorless oil. The oil can be used without further purification. MS (ESI) 316 (M+Na).

Step C. Preparation of 4-(4-fluorophenylmethyl)piperidine HCl salt.

N-(t-butoxycarbonyl)-4-(4-fluorophenylmethyl)piperidine (11.2 g, 38.2 mmol) was dissolved in 4M HCl in dioxane (50 mL). The reaction was stirred for 15 min and then conc. in vacuo to a white solid. The solid was dissolved in 3% MeOH/CH$_2$Cl$_2$ in EtOAc/MeOH while warming once all solids were dissolved hexanes was added. The crystallization was allowed to cool to room temperature and then placed at 4° C. for 16 h. The white solids were filtered off to yield 8.4 g of product. MS (ESI) 194 (M−HCl+H).

Step D. Preparation of (+/−)-N-(t-butoxycarbonyl)-3-hydroxymethylpiperidine.

To a stirring solution of 3-hydroxymethylpiperidine (2100 mg, 18.3 mmol, Aldrich) in dry THF (220 mL) was added di-t-butyl dicarbonate (3790 mg, 17.4 mmol, Aldrich). The reaction was allowed to stir for 5 h and then quenched by the addition of 1M aqueous HCl (100 mL) and EtOAc (200 mL). The organic layer was separated, washed with brine, dried over $Na_2SO_4$, and conc. in vacuo to a colorless oil used without further purification. MS (ESI) 216 (M+H).

Step E. Preparation of (+/−)-N-(t-butoxycarbonyl)-3-piperidinecarboxaldehyde.

To a stirring solution of N-(t-butoxycarbonyl)-3-hydroxymethylpiperidine (3741 mg, 17.4 mmol, Aldrich) in dry $CH_2Cl_2$ (250 mL) was added 4 angstrom molecular sieves (500 mg) and N-methyl-morpholine oxide (3054 mg, 26.1 mmol, Aldrich). After 10 min, tetrapropylammonium perruthenate oxide (305 mg, 0.87 mmol, Aldrich) and the reaction was stirred for 2 h. The reaction was filtered through a pad of silica gel and the silica gel was washed with EtOAc. The organic layers were and conc. in vacuo to a colorless oil which was used without further purification. MS (ESI) 214 (M+H).

Step F. Preparation of (+/−)-N-(t-butoxycarbonyl)-2-[[4-[(4-fluorophenyl)methyl]-1-piperidinyl]methyl]-piperidine.

A solution of (+/−)-N-(t-butoxycarbonyl)-3-piperidinecarboxaldehyde (521 mg, 2.45 mmol) and 4-(4-flourophenylmethyl)piperidine (315 mg, 1.63 mmol) in dry $CH_2Cl_2$ (20 mL) was stirred for 15 min when sodium triacetoxyborohydride (691 mg, 3.26 mmol, Aldrich) was added. The reaction was stirred for 4 h and then quenched with 10% NaOH (10 mL) and $CH_2Cl_2$ (100 mL). The organic layer was separated, dried over $MgSO_4$, and conc. in vacuo to a pale yellow oil. The oil was purified by radial chromatography (SiO2, $CH_2Cl_2$:MeOH, 98:2) to yield 580 mg the product as a colorless oil. MS (ESI) 391 (M+H).

Step G. Preparation of (+/−)-2-[[4-[(4-fluorophenyl)methyl]-1-piperidinyl]methyl]-piperidine.

(+/−)-N-(t-butoxycarbonyl)-2-[[4-[(4-fluorophenyl)methyl]-1-piperidinyl]methyl]-piperidine (340 mg, 0.87 mmol) was dissolved in 4M HCl in dioxane (10 mL). The reaction was stirred for 1 h and then conc. in vacuo to a white solid. The solid was partioned between 10% NaOH and EtOAc. The layers were separated and the aqueous layer was extracted with EtOAc. The organic layers were combined, dried over $MgSO_4$, and conc. in vacuo to a white solid yielding 250 mg of product. MS (ESI) 291 (M+H).

Step H. Preparation of (+/−)-N-phenyl-2-[[4-[(4-fluorophenyl)methyl]-1-piperidinyl]methyl]-1-piperidinecarboxamide.

To a stirring solution of of (+/−)-2-[[4-[(4-fluorophenyl)methyl]-1-piperidinyl]methyl]-piperidine (14.5 mg, 0.05 mmol) in dry THF (0.2 mL) was added phenyl isocyante (13.3 mg, 0.075 mmol, Aldrich). The reaction was stirred for 0.5 and then conc. in vacuo to a pale yellow oil. The oil was purified by flash chromatography (SiO2, 2:1 EtOAc:Hexanes and then 5% TEA in EtOAc) to yield the product as a colorless oil. MS (ESI) 410 (M+H).

Example 2

Preparation of (+/−)-N-(3-cyanophenyl)-2-[[4-[(4-fluorophenyl)methyl]-1-piperidinyl]methyl]-1-piperidinecarboxamide Prepared according to procedures described in Example 1 with modification at Step H. MS (ESI) 435 (M+H).

Example 3

Preparation of (+/−)-N-(3-methoxyphenyl)-2-[[4-[(4-fluorophenyl)methyl]-1-piperidinyl]methyl]-1-piperidinecarboxamide Prepared according to procedures described in Example 1 with modification at Step H. MS (ESI) 440 (M+H).

Example 4

Preparation of (+/−)-N-(4-fluorophenyl)-2-[[4-[(4-fluorophenyl)methyl]-1-piperidinyl]methyl]-1-piperidinecarboxamide Prepared according to procedures described in Example 1 with modification at Step H. MS (ESI) 428 (M+H).

Example 5

Preparation of (+/−)-N-(3-carboethoxyphenyl)-2-[[4-[(4-fluorophenyl)methyl]-1-piperidinyl]methyl]-1-piperidinecarboxamide Prepared according to procedures described in Example 1 with modification at Step H. MS (ESI) 482 (M+H).

Example 6

Preparation of (+/−)-N-(4-carboethoxyphenyl)-2-[[4-[(4-fluorophenyl)methyl]-1-piperidinyl]methyl]-1-piperidinecarboxamide Prepared according to procedures described in Example 1 with modification at Step H. MS (ESI) 482 (M+H).

Example 7

Preparation of (+/−)-N-(1-adamantylphenyl)-2-[[4-[(4-fluorophenyl)methyl]-1-piperidinyl]methyl]-1-piperidinecarboxamide Prepared according to procedures described in Example 1 with modification at Step H. MS (ESI) 468 (M+H).

Example 8

Preparation of (+/−)-N-phenyl-2-[[4-[(4-fluorophenyl)methyl]-1-piperidinyl]ethyl]-1-piperidinecarboxamide Prepared according to procedures described in Example 1 with modification at Step D. MS (ESI) 424 (M+H).

Example 9

Preparation of (+/−)-N-(3-cyanophenyl)-2-[[4-[(4-fluorophenyl)methyl]-1-piperidinyl]ethyl]-1-piperidinecarboxamide Prepared according to procedures described in Example 10 with modification at Step H. MS (ESI) 449 (M+H).

Example 10

Preparation of (+/−)-N-(3-methoxyphenyl)-2-[[4-[(4-fluorophenyl)methyl]-1-piperidinyl]ethyl]-1-piperidinecarboxamide Prepared according to procedures described in Example 10 with modification at Step H. MS (ESI) 454 (M+H).

Example 11

Preparation of (+/−)-N-(4-fluorophenyl)-2-[[4-[(4-fluorophenyl)methyl]-1-piperidinyl]ethyl]-1-piperidinecarboxamide Prepared according to procedures described in Example 10 with modification at Step H. MS (ESI) 442 (M+H).

Example 12

Preparation of (+/−)-N-(3-carboethoxyphenyl)-2-[[4-[(4-fluorophenyl)methyl]-1-piperidinyl]ethyl]-1-piperidinecarboxamide Prepared according to procedures described in Example 10 with modification at Step H. MS (ESI) 496 (M+H).

Example 13

Preparation of (+/−)-N-(4-carboethoxyphenyl)-2-[[4-[(4-fluorophenyl)methyl]-1-piperidinyl]ethyl]-1-piperidinecarboxamide Prepared according to procedures described in Example 10 with modification at Step H. MS (ESI) 496 (M+H).

Example 14

Preparation of (+/−)-N-(1-adamantylphenyl)-2-[[4-[(4-fluorophenyl)methyl]-1-piperidinyl]ethyl]-1-piperidinecarboxamide Prepared according to procedures described in Example 10 with modification at Step H. MS (ESI) 482 (M+H).

Example 15

Preparation of N-phenyl-4-[[4-(phenylmethyl)-1-piperidinyl]methyl]-1-piperidinecarboxamide Prepared according to procedures described in Example 1 with modification at Step D. MS (ESI) 392 (M+H).

Example 16

Preparation of N-(3-cyanophenyl)-4-[[4-(phenylmethyl)-1-piperidinyl]methyl]-1-piperidinecarboxamide Prepared according to procedures described in Example 17 with modification at Step H. MS (ESI) 417 (M+H).

Example 17

Preparation of N-(1-adamantyl)-4-[[4-(phenylmethyl)-1-piperidinyl]methyl]-1-piperidinecarboxamide Prepared according to procedures described in Example 17 with modification at Step H. MS (ESI) 450 (M+H).

Example 18

Preparation of N-(3-methoxyphenyl)-4-[[4-(phenylmethyl)-1-piperidinyl]methyl]-1-piperidinecarboxamide Prepared according to procedures described in Example 17 with modification at Step H. MS (ESI) 422 (M+H).

Example 19

Preparation of N-(3-carboethoxyphenyl)-4-[[4-(phenylmethyl)-1-piperidinyl]methyl]-1-piperidinecarboxamide Prepared according to procedures described in Example 17 with modification at Step H. MS (ESI) 464 (M+H).

Example 20

Preparation of 1-benzoyl-4-[[4-(phenylmethyl)-1-piperidinyl]methyl]piperidine

Step A. Preparation of 1-benzoyl-4-[[4-(phenylmethyl)-1-piperidinyl]methyl]piperidine.
To a stirring solution of of 4-[[4-(phenylmethyl)-1-piperidinyl]methyl]-piperidine (10.1 mg, 0.037 mmol), prepared according to procedures used in Example 1, Steps C–G, in dry THF (0.2 mL) was added benzoyl chloride (7.8 mg, 0.056 mmol, Aldrich) followed by the addition of triethylamine (0.008 mL, Aldrich). The reaction was stirred for 0.5 and then conc. in vacuo to a pale yellow oil. The oil was purified by flash chromatography (SiO2, 2:1 EtOAc:Hexanes and then 5% TEA in EtOAc) to yield the product as a colorless oil. MS (ESI) 377 (M+H).

Example 21

Preparation of 1-phenylacetyl-4-[[4-(phenylmethyl)-1-piperidinyl]methyl]piperidine Prepared according to procedures described in Example 22 with modification at Step A. MS (ESI) 391 (M+H).

Example 22

Preparation of 1-(3,4-dimethoxybenzoyl)-4-[[4-(phenylmethyl)-1-piperidinyl]methyl]piperidine Prepared according to procedures described in Example 22 with modification at Step A. MS (ESI) 473 (M+H).

Example 23

Preparation of 1-(3,5-dichlorobenzoyl)-4-[[4-(phenylmethyl)-1-piperidinyl]methyl]piperidine Prepared according to procedures described in Example 22 with modification at Step A. MS (ESI) 446 (M+H).

Example 24

Preparation of 1-(3,5-difluorobenzoyl)-4-[[4-(phenylmethyl)-1-piperidinyl]methyl]piperidine Prepared according to procedures described in Example 22 with modification at Step A. MS (ESI) 413 (M+H).

Example 25

Preparation of 1-(3,5-dimethoxybenzoyl)-4-[[4-(phenylmethyl)-1-piperidinyl]methyl]piperidine Prepared according to procedures described in Example 22 with modification at Step A. MS (ESI) 437 (M+H).

Example 26

Preparation of 1-(3,4-methylenedioxybenzoyl)-4-[[4-(phenylmethyl)-1-piperidinyl]methyl]piperidine Prepared according to procedures described in Example 22 with modification at Step A. MS (ESI) 421 (M+H).

Example 27

Preparation of 1-(2-thiophenesulfonyl)-4-[[(4-(phenylmethyl)-1-piperidinyl]methyl]-piperidinecarboxamide Prepared according to procedures described in Example 22 with modification at Step A. MS (ESI) 419 (M+H).

Example 28

Preparation of 1-(3-methoxyphenylacetyl)-4-[[4-(phenylmethyl)-1-piperidinyl]methyl]piperidine Prepared according to procedures described in Example 22 with modification at Step A. MS (ESI) 421 (M+H).

Example 29

Preparation of 1-(4-methoxyphenylacetyl)-4-[[4-(phenylmethyl)-1-piperidinyl]methyl]piperidine Prepared according to procedures described in Example 22 with modification at Step A. MS (ESI) 421 (M+H).

Example 30

Preparation of (+/−)-N-phenyl-3-[[4-[(4-fluorophenyl)methyl]-1-piperidinyl]methyl]-1-piperidinecarboxamide Part A. Preparation of (+/−)-N-(t-butoxycarbonyl)-3-piperidinemethanol p-methylbenzenesulfonate.

To a stirring solution of N-(t-butoxycarbonyl)-3-piperidinemethanol (16.33 g, 75.6 mmol), prepared according to procedure in Example 1, Part A, and dry pyridine (12.2 mL, Aldrich) in dry $CH_2Cl_2$ (200 mL) was added p-toluenesulfonyl chloride (15.9 g, 83.2 mmol, Aldrich). The reaction was stirred for 4 h. The reaction was quenched by the addition of saturated aqueous $NaHCO_3$ (100 mL). The organic layer was separated, washed with water, washed with brine, dried over $MgSO_4$, and conc. in vacuo to a yellow oil. The oil was purified by flash chromatography (SiO2, 5–40% EtOAc in hexanes) to yield 20.2 g of a white solid. MS (ESI) 370 (M+H).

Part B. Preparation of (+/−)-N-(t-butoxycarbonyl)-2-[[4-[(4-fluorophenyl)methyl]-1-piperidinyl]methyl]-piperidine.

To a stirring solution of (+/−)-N-(t-butoxycarbonyl)-3-piperidinemethanol p-methylbenzenesulfonate (500 mg, 1.4 mmol) and dry triethylamine (0.59 mL, Aldrich) in dry THF (10 mL) was added and 4-(4-flourophenylmethyl)piperidine (290, 1.5 mmol). The reaction was heat to reflux for 16 h. The reaction was cooled to room temperature and quenched by the addition of 1M NaOH (10 mL) and EtOAc (10 mL). The organic layer was separated, washed with water, washed with brine, dried over $MgSO_4$, and conc. in vacuo to a yellow oil. The oil was purified by flash chromatography (SiO2, 2.5% MeOH in $CH_2Cl_2$) to yield 476 mg of a colorless oil. MS (ESI) 391 (M+H).

Part C. Preparation of (+/−)-N-phenyl-3-[[4-[(4-fluorophenyl)methyl]-1-piperidinyl]methyl]-1-piperidinecarboxamide.

The titled compound was synthesized from the product of Part B following the procedures outlined in Example 1, Part G and H. MS (ESI) 410 (M+H).

Example 31

Preparation of (+/−)-N-(3-cyanophenyl)-3-[[4-[(4-fluorophenyl)methyl]-1-piperidinyl]methyl]-1-piperidinecarboxamide Prepared according to procedures described in Example 32 with modification at Step C. MS (ESI) 435 (M+H).

Example 32

Preparation of (+/−)-N-(l-adamantylphenyl)-3-[[4-[(4-fluorophenyl)methyl]-1-piperidinyl]methyl]-1-piperidinecarboxamide Prepared according to procedures described in Example 32 with modification at Step C. MS (ESI) 468 (M+H).

Example 33

Preparation of (+/−)-N-(3-carboethoxyphenyl)-3-[[4-[(4-fluorophenyl)methyl]-1-piperidinyl]methyl]-1-piperidinecarboxamide Prepared according to procedures described in Example 32 with modification at Step C. MS (ESI) 482 (M+H).

Example 34

Preparation of (+/−)-N-(4-fluorophenyl)-3-[[4-[(4-fluorophenyl)methyl]-1-piperidinyl]methyl]-1-piperidinecarboxamide Prepared according to procedures described in Example 32 with modification at Step C. MS (ESI) 428 (M+H).

Example 35

Preparation of (+/−)-N-(3-methoxyphenyl)-3-[[4-[(4-fluorophenyl)methyl]-1-piperidinyl]methyl]-1-piperidinecarboxamide Prepared according to procedures described in Example 32 with modification at Step C. MS (ESI) 440 (M+H).

Example 36

Preparation of (+/−)-N-phenyl-3-[[4-(phenylmethyl)-1-piperidinyl]methyl]-1-piperidinecarboxamide Prepared according to procedures described in Example 32 with modification at Step B. MS (ESI) 392 (M+H).

Example 37

Preparation of (+/−)-N-(3-methoxyphenyl)-3-[[4-(phenylmethyl)-1-piperidinyl]methyl]-1-piperidinecarboxamide Prepared according to procedures described in Example 38 with modification at Step C. MS (ESI) 422 (M+H).

Example 38

Preparation of (+/−)-N-(3-carboethoxyphenyl)-3-[[4-(phenylmethyl)-1-piperidinyl]methyl]-1-piperidinecarboxamide Prepared according to procedures described in Example 38 with modification at Step C. MS (ESI) 464 (M+H).

Example 39

Preparation of (+/−)-N-(3-cyanophenyl)-3-[[4-(phenylmethyl)-1-piperidinyl]methyl]-1-piperidinecarboxamide Prepared according to procedures described in Example 38 with modification at Step C. MS (ESJ) 417 (M+H).

Example 40

Preparation of (+/−)-N-(1-adamantyl)-3-[[4-(phenylmethyl)-1-piperidinyl]methyl]-1-piperidinecarboxamide Prepared according to procedures described in Example 38 with modification at Step C. MS (ESI) 450 (M+H).

Example 41

Preparation of (+/−)-N-phenyl-3-[[4-[(4-fluorophenyl)methyl]-1-piperidinyl]methyl]-1-pyrrolidinecarboxamide Part A. Preparation of N-(benzyloxycarbonyl)-3-pyrrolidinol.

To a stirring solution of 3-pyrrolidinol (1780 mg, 20.4 mmol, Aldrich) and dry triethylamine (4130 mg, 40.9 mmol, Aldrich) in dry $CH_2Cl_2$ (120 mL) at 0° C. was benylchloroformate (3.83 mg, 22.5 mmol, Aldrich). The reaction was allowed to warm to room temperature and stirred for 16 h. The reaction was quenched by the addition of 1M aqueous HCl (100 mL) and EtOAc (200 mL). The organic layer was separated, washed with brine, dried over $Na_2SO_4$, and conc. in vacuo to a colorless oil. The oil was purified by flash chromatography (SiO2, hex:EtOAc, 2:1) to yield of pure N-(benzyloxycarbonyl)-3-pyrrolidinol. MS (ESI) 222 (M+H).

Part B. Preparation of N-(benzyloxycarbonyl)-3-pyrrolidinone.

To a stirring solution of N-(benzyloxycarbonyl)-3-pyrrolidinol (1600 mg, 7.2 mmol) and 4-methylmorpholine oxide (1269 mg, 10.8 mmol, Aldrich) in dry $CH_2Cl_2$ (100 mL) with activated molecular sieves (1000 mg) was added tetrapropylammonium perruthenate (127 mg, 0.36 mmol, Aldrich). The reaction was stirred for 1 h and then filtered through a pad of silica gel. The silica gel was washed with EtOAc (500 mL). The organic filtrates were combined and conc. in vacuo to a colorless oil of pure N-(benzyloxycarbonyl)-3-pyrrolidinone. MS (ESI) 220 (M+H).

Step C. Preparation of N-(benzyloxycarbonyl)-3-(methoxymethalene)-pyrrolidine.

To a stirring solution of (methoxymethyl)triphenylphosphonium chloride (5389 mg, 15.7 mmol, Aldrich) in dry THF (30 mL) at 0° C. was added a 1M solution of lithium diisopropylamine (13.1 mL). The reaction was stirred for 20 min and then a solution of N-(benzyloxycarbonyl)-3-pyrrolidinone (1434 mg, 6.55 mmol) in THF (20 mL) was added. After 10 min, the reaction was warmed to room temperature for 1 h and heated to reflux for 3.5 h. After cooling to room temperature, the reaction was quenched by the addition of brine (100 mL). The reaction was extracted with EtOAc (3×100 mL). The organic layers were combined, dried over $MgSO_4$, and conc. in vacuo to a brown oil. The oil was purified by flash chromatography (SiO2, hex:EtOAc, 4:1) to yield the product as a colorless oil. MS (ESI) 248 (M+H).

Part D. Preparation of (+/−)-N-(benzyloxycarbonyl)-3-pyrrolidinecarboxaldehyde.

To a stirring solution N-(benzyloxycarbonyl)-3-(methoxymethalene)-pyrrolidine (1000 mg, 4.1 mmol) in THF (50 mL) was added 3M aqueous HCl (50 mL). The reaction was stirred for 4 h and then was extracted with $CH_2Cl_2$ (3×100 mL). The organic layers were combined, dried over $MgSO_4$, and conc. in vacuo to yield the product as a colorless oil. The oil can be used without further purification. MS (ESI) 234 (M+H).

Step E. Preparation of (+/−)-3-[4-(4-flourophenylmethyl)piperidinomethyl]-N-(benzyloxycarbonyl)-pyrrolidine.

A solution of (+/−)-N-(benzyloxycarbonyl)-3-pyrrolidinecarboxaldehyde (416 mg, 1.79 mmol) and 4-(4-flourophenylmethyl)piperidine (518 mg, 2.69 mmol) in dry $CH_2Cl_2$ (15 mL) were stirred for 15 min when sodium triacetoxyborohydride (759 mg, 3.58 mmol, Aldrich) was added. The reaction was stirred for 2 h and then quenched with 1M aqueous HCl (50 mL) and $CH_2Cl_2$ (200 mL). The reaction was brought to pH 11 with 1M aqueous NaOH. The organic layer was separated, washed with brine, dried over $MgSO_4$, and conc. in vacuo to a pale yellow oil. The oil was purified by radial chromatography (SiO2, $CH_2Cl_2$:MeOH, 97:3) to yield the product as a colorless oil. MS (ESI) 411 (M+H).

Part F. Preparation of (+/−)-3-[4-(4-flourophenylmethyl)piperidinomethyl]-pyrrolidine.

To a stirring solution of 3-[4-(4-flourophenylmethyl)piperidinomethyl]-N-(benzyloxycarbonyl)-pyrrolidine (600 mg, 1.47 mmol) and 5% palladium on carbon (60 mg, Aldrich) in MeOH (50 mL) was added 50 psi of hydrogen. The reaction was stirred for 14 h. The reaction was filtered and the filtrate was conc. in vacuo to a colorless oil. The oil can be used without further purification. MS (ESI) 277 (M+H).

Part G. Preparation of (+/−)-N-phenyl-3-[[4-[(4-fluorophenyl)methyl]-1-piperidinyl]methyl]-1-pyrrolidinecarboxamide.

Prepared according to procedures described in Example 1 with modification at Step H. MS (ESI) 396 (M+H).

Example 42

Preparation of (+/−)-N-(3-cyanophenyl)-3-[[4-[(4-fluorophenyl)methyl]-1-piperidinyl]methyl]-1-pyrrolidinecarboxamide Prepared according to procedures described in Example 43 with modification at Step G. MS (ESI) 421 (M+H).

Example 43

Preparation of (+/−)-N-(3-methoxyphenyl)-3-[[4-[(4-fluorophenyl)methyl]-1-piperidinyl]methyl]-1-pyrrolidinecarboxamide Prepared according to procedures described in Example 43 with modification at Step G. MS (ESI) 426 (M+H).

Example 44

Preparation of (+/−)-N-(4-fluorophenyl)-3-[[4-[(4-fluorophenyl)methyl]-1-piperidinyl]methyl]-1-piperidinecarboxamide Prepared according to procedures described in Example 43 with modification at Step G. MS (ESI) 414 (M+H).

Example 45

Preparation of (+/−)-N-(3-carboethoxyphenyl)-3-[[4-[(4-fluorophenyl)methyl]-1-piperidinyl]methyl]-1-pyrrolidinecarboxamide Prepared according to procedures described in Example 43 with modification at Step G. MS (ESI) 468 (M+H).

Example 46

Preparation of (+/−)-N-(4-carboethoxyphenyl)-3-[[4-[(4-fluorophenyl)methyl]-1-piperidinyl]methyl]-1-pyrrolidinecarboxamide Prepared according to procedures described in Example 43 with modification at Step G. MS (ESI) 468 (M+H).

Example 47

Preparation of (+/−)-N-(1-adamantylphenyl)-3-[[4-[(4-fluorophenyl)methyl]-1-piperidinyl]methyl]-1-pyrrolidinecarboxamide Prepared according to procedures described in Example 43 with modification at Step G. MS (ESI) 453 (M+H).

Example 48

Preparation of (+/−)-1-benzyloxycarbonyl-3-[[4-[(4-fluorophenyl)methyl]-1-piperidinyl]ethyl]-1-piperidine Prepared according to procedures described in Example 43, Parts A–E with modification at Step A. MS (ESI) 438 (M+H).

Example 49

Preparation of (+/−)-N-phenyl-3-[[4-[(4-fluorophenyl)methyl]-1-piperidinyl]ethyl]-1-piperidinecarboxamide Prepared according to procedures described in Example 50 followed by procedures described in Example 43, Parts F and G. MS (ESI) 423 (M+H).

Example 50

Preparation of (+/−)-N-(3-cyanophenyl)-3-[[4-[(4-fluorophenyl)methyl]-1-piperidinyl]ethyl]-1-piperidinecarboxamide Prepared according to procedures described in Example 51 with modification at Step G. MS (ESI) 449 (M+H).

Example 51

Preparation of (+/−)-N-(3-carboethoxyphenyl)-3-[[4-[(4-fluorophenyl)methyl]-1-piperidinyl]ethyl]-1-piperidinecarboxamide Prepared according to procedures described in Example 51 with modification at Step G. MS (ESI) 496 (M+H).

Example 52

Preparation of (+/−)-N-(4-carboethoxyphenyl)-3-[[4-[(4-fluorophenyl)methyl]-1-piperidinyl]ethyl]-1-piperidinecarboxamide Prepared according to procedures described in Example 51 with modification at Step G. MS (ESI) 496 (M+H).

Example 53

Preparation of (+/−)-N-(4-fluorophenyl)-3-[[4-[(4-fluorophenyl)methyl]-1-piperidinyl]ethyl]-1-piperidinecarboxamide Prepared according to procedures described in Example 51 with modification at Step G. MS (ESI) 442 (M+H).

Example 54

Preparation of (+/−)-N-(1-adamantylphenyl)-3-[[4-[(4-fluorophenyl)methyl]-1-piperidinyl]ethyl]-1-piperidinecarboxamide Prepared according to procedures described in Example 51 with modification at Step G. MS (ESI) 482 (M+H).

Example 55

Preparation of (+/−)-N-(3-methoxyphenyl)-3-[[4-[(4-fluorophenyl)methyl]-1-piperidinyl]ethyl]-1-piperidinecarboxamide Prepared according to procedures described in Example 51 with modification at Step G. MS (ESI) 453 (M+H).

Example 56

Preparation of (+/−)-1-phenylsulfonyl-3-[[4-[(4-fluorophenyl)methyl]-1-piperidinyl]ethyl]-piperidinecarboxamide Prepared according to procedures described in Example 51 with modification at Step G, according to Example 22, Part A. MS (ESI) 445 (M+H).

Example 57

Preparation of (+/−)-1-benzoyl-3-[[4-[(4-fluorophenyl)methyl]-1-piperidinyl]ethyl]-1-piperidinecarboxamide Prepared according to procedures described in Example 51 with modification at Step G, according to Example 22, Part A. MS (ESI) 409 (M+H).

Example 58

Preparation of (+/−)-N-phenyl-2-[[4-[(4-fluorophenyl)methyl]-1-piperidinyl]methyl]-4-morpholinecarboxamide Part A. Preparation of (+/−)-2-(phenylmethoxymethyl)oxirane.

To a stirring solution of (+/−)-2-(hydroxymethyl)oxirane (3.0 g, 40.5 mmol, Aldrich) in dry DMF (40 mL) was added sodium hydride (883 mg, 36.8 mmol, Aldrich). The reaction was stirred for 7 min when benzyl bromide (6.3 g, 36.8 mmol, Aldrich) was added. The reaction was stirred for 2 h and then quenched by the addition of water (50 mL). The reaction was extracted with EtOAc (4×50 mL). The organic layers were combined, washed with brine, dried over $Na_2SO_4$, and conc. in vacuo to a yellow oil. The oil was purified by flash chromatography (SiO2, 5–20% EtOAc in hexanes) to yield 4.15 g of a colorless oil. MS (ESI) 164 (M+H).

Part B. Preparation of (+/−)-2-(phenylmethoxymethyl)-morpholine.

A stirring solution of (+/−)-2-(phenylmethoxymethyl)oxirane (2.46 g, 15 mmol) in MeOH (30 mL) was warmed to 40° C. and then sodium hydroxide (4.8 g, Aldrich) as a 16M solution in water and 2-aminoethylsulfate (8.92 g, 63 mmol, Aldrich) were added. The reaction was heated for 2 h when sodium hydroxide (3.75 g, 93.8 mmol, Aldrich) and toluene (12 mL) were added. The reaction was warmed to 68° C. for 8 h and then quenched by the addition of water (20 mL) and toluene (10 mL). The reaction was extracted with 2M HCl. The aqueous layer was separated, basefied with NaOH, and extracted with toluene (4×100 mL). The organic layers were combined, washed with brine, dried over $Na_2SO_4$, and conc. in vacuo to a yellow oil. The oil was purified by flash chromatography (SiO2, 5–10% MeOH in $CH_2Cl_2$ then 10% TEA and 10% MeOH in $CH_2Cl_2$) to yield 450 mg of a colorless oil. MS (ESI) 208 (M+H).

Step C. Preparation of (+/−)-N-(t-butoxycarbonyl)-2-(phenylmethoxymethyl)-morpholine.

To a stirring solution of 2-(phenylmethoxymethyl)-morpholine (450 mg, 2.17 mmol) in dry THF (20 mL) was added di-t-butyl dicarbonate (473 mg, 2.17 mmol, Aldrich). The reaction was allowed to stir for 1 h and then conc. in vacuo to an oil. The oil was purified by flash chromatography (SiO2, Hexanes:EtOAc 4:1) to yield 595 mg of a colorless oil. MS (CI) 308 (M+H).

Part D. Preparation of (+/−)-N-(t-butoxycarbonyl)-2-hydroxymethyl-morpholine.

To a stirring solution of (+/−)-N-(t-butoxycarbonyl)-2-(phenylmethoxymethyl)-morpholine (595 mg, 1.94 mmol) and 20% palladium on carbon (120 mg, Aldrich) in MeOH (20 mL) was added 50 psi of hydrogen. The reaction was stirred for 4 h. The reaction was filtered and the filtrate was conc. in vacuo to a colorless oil. The oil can be used without further purification. MS (CI) 218 (M+H).

Part E. Preparation of (+/−)-N-phenyl-2-[[4-[(4-fluorophenyl)methyl]-1-piperidinyl]methyl]-4-morpholinecarboxamide.

The titled compound was synthesized from the product of Part D following the procedures outlined in Example 1, Parts E–H. MS (ESI) 412 (M+H).

Example 59

Preparation of (+/−)-N-(3-cyanophenyl)-2-[[4-[(4-fluorophenyl)methyl]-1-piperidinyl]methyl]-4-morpholinecarboxamide Prepared according to procedures described in Example 60 with modification at Step H. MS (ESI) 437 (M+H).

Example 60

Preparation of (+/−)-N-(3-carboethoxyphenyl)-2-[[4-[(4-fluorophenyl)methyl]-1-piperidinyl]methyl]-4-morpholinecarboxamide Prepared according to procedures described in Example 60 with modification at Step H. MS (ESI) 484 (M+H).

Example 61

Preparation of (+/−)-N-(4-carboethoxyphenyl)-2-[[4-[(4-fluorophenyl)methyl]-1-piperidinyl]methyl]-4-morpholinecarboxamide Prepared according to procedures described in Example 60 with modification at Step H. MS (ESI) 484 (M+H).

Example 62

Preparation of (+/−)-N-(4-fluorophenyl)-2-[[4-[(4-fluorophenyl)methyl]-1-piperidinyl]methyl]-4-morpholinecarboxamide Prepared according to procedures described in Example 60 with modification at Step H. MS (ESI) 430 (M+H).

Example 63

Preparation of (+/−)-N-(1-adamantylphenyl)-2-[[4-[(4-fluorophenyl)methyl]-1-piperidinyl]methyl]-4-morpholinecarboxamide Prepared according to procedures described in Example 60 with modification at Step H. MS (ESI) 470 (M+H).

Example 64

Preparation of (+/−)-N-(3-methoxyphenyl)-2-[[4-[(4-fluorophenyl)methyl]-1-piperidinyl]methyl]-4-morpholinecarboxamide Prepared according to procedures described in Example 60 with modification at Step H. MS (ESI) 442 (M+H).

Example 65

Preparation of (+/−)-N-phenyl-3-[[4-[(4-fluorophenyl)methyl]-1-piperidinyl]methyl]-3-hydroxy-1-piperidinecarboxamide Step A. Preparation of N-(t-butoxycarbonyl)-3-(methalene)piperidine.

To a stirring solution of methyltriphenylphosphonium chloride (3.59 g, 10 mmol, Aldirch) in dry THF (50 mL) at −78° C. was added a 2.5M solution of n-butyl lithium in hexanes (4 mL). The reaction was stirred for 5 min and then warmed to 0° C. when a solution of N-(t-butoxycarbonyl)-3-piperidone (1 g, 5.02 mmol) in dry THF (5 mL) was added. After 10 min, the reaction was warmed to room temperature for 15 h. The reaction was quenched by the addition of 0.25 M HCl (40 mL). The reaction was extracted with EtOAc (3×50 mL). The organic layers were combined, dried over $Na_2SO_4$, and conc. in vacuo to an oil. The oil was purified by flash chromatography (SiO2, 10% EtOAc in hexanes) to yield 819 mg (83%) of the product as a white solid. MS (ESI) 219 (M+Na).

Step B. Preparation of (+/−)-N-(t-butoxycarbonyl)-1-oxa-5-azaspiro[2.5]octane.

To a stirring solution of N-(t-butoxycarbonyl)-3-(methalene)piperidine (400 mg, 2.03 mmol) and sodium carbonate (682 mg, 4.0 mmol) in chloroform (20 mL) at 0° C. was added m-chloroperoxybenzoic acid (701 mg, 4.06 mmol). The reaction was stirred for 3 h at 0° C. and then quenched by the addition of sat. $Na_2CO_3$ (20 mL). The reaction was extracted with $EtO_2$ (3×20 mL). The organic layers were combined, washed with sodium sulfite, washed with sodium bicarbonate, washed with brine, dried over $Na_2SO_4$, and conc. in vacuo to an oil. The oil was purified by flash chromatography (SiO2, 20% EtOAc in hexanes) to yield 343 mg of the product as a colorless oil. MS (ESI) 213 (M+H).

Step C. Preparation of (+/−)-N-(t-butoxycarbonyl)-3-[[4-[(4-fluorophenyl)methyl]-1-piperidinyl]methyl]-3-hydroxy-1-piperidine.

To a stirring solution of N-(t-butoxycarbonyl)-1-oxa-5-azaspiro[2.5]octane (200 mg, 1.06 mmol) in DMF (5 mL) was added and 4-(4-flourophenylmethyl)piperidine (226 mg, 1.17 mmol). The reaction was warmed to 80° C. for 17 h and then warmed to 110° C. for 8 h. A second portion of and 4-(4-flourophenylmethyl)piperidine (100 mg) and heated at 95° C. for 16 h. The reaction was conc. in vacuo to an oil. The oil was purified by flash chromatography (SiO2, 15–50% EtOAc in hexanes) to yield 137 mg of the product as a colorless oil. MS (ESI) 407 (M+H).

Part D. Preparation of (+/−)-N-phenyl-3-[[4-[(4-fluorophenyl)methyl]-1-piperidinyl]methyl]-3-hydroxy-1-piperidinecarboxamide.

The titled compound was synthesized from the product of Part C following the procedures outlined in Example 1, Part G and H. MS (ESI) 426 (M+H).

Example 66

Preparation of (+/−)-N-(3-cyanophenyl)-3-[[4-[(4-fluorophenyl)methyl]-1-piperidinyl]methyl]-3-hydroxy-1-piperidinecarboxamide Prepared according to procedures described in Example 67 with modification at Step H. MS (ESI) 451 (M+H).

Example 67

Preparation of (+/−)-N-(3-carboethoxyphenyl)-3-[[4-[(4-fluorophenyl)methyl]-1-piperidinyl]methyl]-3-hydroxy-1-piperidinecarboxamide Prepared according to procedures described in Example 67 with modification at Step H. MS (ESI) 498 (M+H).

Example 68

Preparation of (+/−)-N-(4-carboethoxyphenyl)-3-[[4-[(4-fluorophenyl)methyl]-1-piperidinyl]methyl]-3-hydroxy-1-piperidinecarboxamide Prepared according to procedures described in Example 67 with modification at Step H. MS (ESI) 498 (M+H).

Example 69

Preparation of (+/−)-N-(4-fluorophenyl)-3-[[4-[(4-fluorophenyl)methyl]-1-piperidinyl]methyl]-3-hydroxy-1-piperidinecarboxamide Prepared according to procedures described in Example 67 with modification at Step H. MS (ESI) 444 (M+H).

Example 70

Preparation of (+/−)-N-(3-methoxyphenyl)-3-[[4-[(4-fluorophenyl)methyl]-1-piperidinyl]methyl]-3-hydroxy-1-piperidinecarboxamide Prepared according to procedures described in Example 67 with modification at Step H. MS (ESI) 456 (M+H).

Example 71

Preparation of (+/−)-N-phenyl-3-[[4-[(4-fluorophenyl)methyl]-1-piperidinyl]methyl]-3-phenylmethyl-1-piperidinecarboxamide Step A. Preparation of (+/−)-N-(t-butoxycarbonyl)-3-(carboethoxy)-3-(phenylmethyl)-piperidine.

To a stirring solution of N-(t-butoxycarbonyl)-3-(carboethoxy)-piperidine (800 mg, 3.11 mmol) in dry THF (10 mL) at −78° C. was added a 0.6M solution of sodium hexamethyldisilazide in toluene (5.7 mL). The reaction was stirred for 1 h when benzyl bromide (559 mg, 3.27 mmol) was added. After 1 h, the reaction was warmed to room temperature for 15 h. The reaction was quenched by the addition of 1M HCl (10 mL). The reaction was extracted with EtOAc (4×20 mL). The organic layers were combined, washed with brine, dried over Na$_2$SO$_4$, and conc. in vacuo to an oil. The oil was purified by flash chromatography (SiO2, 5–15% EtOAc in hexanes) to yield 606 mg of the product as a colorless oil. MS (ESI) 348 (M+H).

Step B. Preparation of (+/−)-N-(t-butoxycarbonyl)-3-(hydroxymethyl)-3-(phenylmethyl)-piperidine.

To a stirring solution (+/−)-N-(t-butoxycarbonyl)-3-(carboethoxy)-3-(phenylmethyl)-piperidine (200 mg, 0.58 mmol) in dry toluene (20 mL) at −78° C. was added a 1.5 M solution of diisobutylaluminium hydride in toluene (2.0 mL). After 6 h, the reaction was warmed to room temperature and quenched by the addition of 1M HCl (50 mL). The reaction was extracted with EtOAc (4×40 mL). The organic layers were combined, washed with brine, dried over Na$_2$SO$_4$, and conc. in vacuo to an oil. The oil was purified by flash chromatography (SiO2, 7–20% EtOAc in hexanes) to yield 86 mg of the product as a colorless oil. MS (ESI) 306 (M+H).

Part C. Preparation of (+/−)-N-phenyl-3-[[4-[(4-fluorophenyl)methyl]-1-piperidinyl]methyl]-3-phenylmethyl-1-piperidinecarboxamide.

The titled compound was synthesized from the product of Part B following the procedures outlined in Example 1, Parts E–H. MS (ESI) 500 (M+H).

Example 72

Preparation of (+/−)-N-(3-cyanophenyl)-3-[[4-[(4-fluorophenyl)methyl]-1-piperidinyl]methyl]-3-phenylmethyl-1-piperidinecarboxamide Prepared according to procedures described in Example 73 with modification at Step H. MS (ESI) 525 (M+H).

Example 73

Preparation of (+/−)-N-(4-fluorophenyl)-3-[[4-[(4-fluorophenyl)methyl]-1-piperidinyl]methyl]-3-phenylmethyl-1-piperidinecarboxamide Prepared according to procedures described in Example 73 with modification at Step H. MS (ESI) 518 (M+H).

Example 74

Preparation of (+/−)-N-(3-methoxyphenyl)-3-[[4-[(4-fluorophenyl)methyl]-1-piperidinyl]methyl]-3-phenylmethyl-1-piperidinecarboxamide Prepared according to procedures described in Example 73 with modification at Step H. MS (ESI) 530 (M+H).

Example 75

Preparation of (+/−)-(cis)-N-phenyl-3-[[4-[(4-fluorophenyl)methyl]-1-piperidinyl]methyl]-2-phenylmethyl-1-piperidinecarboxamide Part A. Preparation of N-(benzyloxycarbonyl)-2-phenylmethyl-3-piperidone.

A stirring solution of N-(benzyloxycarbonyl)-3-piperidone (1000 mg, 4.25 mmol) and pyrrolidine (454 mg, 6.38 mmol, Aldrich) in dry toluene (10 mL) in a round bottom flask fitted with a Dean-Stark trap was refluxed for 4 h. The reaction was conc. in vacuo to a orange oil. The oil was dissolved in dry acetonitrile (10 mL) and then benzyl bromide (800 mg, 4.68 mmol, Aldrich) was added. The reaction was heated to reflux for 16 h and then cooled to room temperature. The reaction was quenched by the addition of 1M HCl (50 mL) and then extracted with EtOAc (4×40 mL). The organic layers were combined, washed with brine, dried over Na$_2$SO$_4$, and conc. in vacuo to an oil. The oil was purified by flash chromatography (SiO2, 7–20% EtOAc in hexanes) to yield 86 mg of the product as a white solid. MS (ESI) 324 (M+H).

Step B. Preparation of N-(benzyloxycarbonyl)-2-phenylmethyl-3-(methoxymethalene)-piperidine.

To a stirring solution of (methoxymethyl)triphenylphosphonium chloride (909 mg, 2.65 mmol, Aldrich) in dry THF (24 mL) at −78° C. was added a 1M solution of lithium diisopropylamine (2.0 mL). The reaction was stirred for 40 min and then a solution of N-(benzyloxycarbonyl)-2-phenylmethyl-3-piperidone (405 mg, 1.25 mmol) in THF (6 mL) was added. After 10 min, the reaction was warmed to room temperature for 1.5 h and heated to reflux for 16 h. After cooling to room temperature, the reaction was quenched by the addition of brine (30 mL). The reaction was extracted with EtOAc (3×30 mL). The organic layers were combined, dried over MgSO$_4$, and conc. in vacuo to a brown oil. The oil was purified by flash chromatography (SiO2, 7–20% EtOAc in hexanes) to yield the product as a yellow oil. MS (ESI) 322 (M+H).

Part C. Preparation of (cis) and (trans)-(+/−)-N-(benzyloxycarbonyl)-2-phenylmethyl-3-piperidinecarboxaldehyde.

To a stirring solution N-(benzyloxycarbonyl)-2-phenylmethyl-3-(methoxymethalene)-piperidine (255 mg, 0.79 mmol) in THF (25 mL) was added 3M aqueous HCl (25 mL). The reaction was stirred for 24 h and then was extracted with CH$_2$Cl$_2$ (3×100 mL). The organic layers were combined, dried over MgSO$_4$, and conc. in vacuo to yield 250 mg of the product as a colorless oil. The oil can be used without further purification. MS (ESI) 308 (M+H).

Step D. Preparation of (+/−)-(cis)-N-(benzyloxycarbonyl)-3-[[4-[(4-fluorophenyl)methyl]-1-piperidinyl]methyl]-2-(phenylmethyl)-piperidine and (+/−)-(trans)-N-(benzyloxycarbonyl)-3-[[4-[(4-fluorophenyl)methyl]-1-piperidinyl]methyl]-2-(phenylmethyl)-piperidine.

A solution of (cis) and (trans)-(+/−)-N-(benzyloxycarbonyl)-2-phenylmethyl-3-piperidinecarboxaldehyde (237 mg, 0.769 mmol) and 4-(4-flourophenylmethyl)piperidine (223 mg, 1.15 mmol) in dry dichloroethane (15 mL) were stirred for 15 min when sodium triacetoxyborohydride (759 mg, 3.58 mmol, Aldrich) was added. The reaction was stirred for 72 h and then quenched with 1M aqueous HCl (50 mL) and CH$_2$Cl$_2$ (200 mL). The reaction was brought to pH 11 with 1M aqueous NaOH. The organic layer was separated, washed with brine, dried over MgSO$_4$, and conc. in vacuo to a pale yellow oil. The oil was purified by flash chromatography (SiO2, 25–40% EtOAc in hexanes) to yield 93 mg of the cis product and 128 mg of the trans product as colorless oils. MS (ESI) 487 (M+H).

Part E. Preparation of (+/−)-(cis)-N-(phenyl)-3-[[4-[(4-fluorophenyl)methyl]-1-piperidinyl]methyl]-2-phenylmethyl-1-piperidinecarboxamide.

The titled compound was synthesized from the cis product of Part D following the procedures outlined in Example 43, Parts F and G. MS (ESI) 500 (M+H).

Example 76

Preparation of (+/−)-(cis)-N-(3-cyanophenyl)-3-[[4-[(4-fluorophenyl)methyl]-1-piperidinyl]methyl]-2-phenylmethyl-1-piperidinecarboxamide Prepared according to procedures described in Example 77 with modification at Step G. MS (ESI) 525 (M+H).

Example 77

Preparation of (+/−)-(cis)-N-(3-carboethoxyphenyl)-3-[[4-[(4-fluorophenyl)methyl]-1-piperidinyl]methyl]-2-phenylmethyl-1-piperidinecarboxamide Prepared according to procedures described in Example 77 with modification at Step G. MS (ESI) 572 (M+H).

Example 78

Preparation of (+/−)-(cis)-N-(4-carboethoxyphenyl)-3-[[4-[(4-fluorophenyl)methyl]-1-piperidinyl]methyl]-2-phenylmethyl-1-piperidinecarboxamide Prepared according to procedures described in Example 77 with modification at Step G. MS (ESI) 572 (M+H).

Example 79

Preparation of (+/−)-(cis)-N-(4-fluorophenyl)-3-[[4-[(4-fluorophenyl)methyl]-1-piperidinyl]methyl]-2-phenylmethyl-1-piperidinecarboxamide Prepared according to procedures described in Example 77 with modification at Step G. MS (ESI) 518 (M+H).

Example 80

Preparation of (+/−)-(cis)-N-(3-methoxyphenyl)-3-[[4-[(4-fluorophenyl)methyl]-1-piperidinyl]methyl]-2-phenylmethyl-1-piperidinecarboxamide Prepared according to procedures described in Example 77 with modification at Step G. MS (ESI) 530 (M+H).

Example 81

Preparation of (+/−)-(trans)-N-phenyl-3-[[4-[(4-fluorophenyl)methyl]-1-piperidinyl]methyl]-2-phenylmethyl-1-piperidinecarboxamide The titled compound was synthesized from the trans product of Example 77, Part D following the procedures outlined in Example 43, Parts F and G. MS (ESI) 500 (M+H).

Example 82

Preparation of (+/−)-(trans)-N-(3-cyanophenyl)-3-[[4-[(4-fluorophenyl)methyl]-1-piperidinyl]methyl]-2-phenylmethyl-1-piperidinecarboxamide Prepared according to procedures described in Example 83 with modification at Step G. MS (ESI) 525 (M+H).

Example 83

Preparation of (+/−)-(trans)-N-(3-carboethoxyphenyl)-3-[[4-[(4-fluorophenyl)methyl]-1-piperidinyl]methyl]-2-phenylmethyl-1-piperidinecarboxamide Prepared according to procedures described in Example 83 with modification at Step G. MS (ESI) 572 (M+H).

Example 84

Preparation of (+/−)-(trans)-N-(4-carboethoxyphenyl)-3-[[4-[(4-fluorophenyl)methyl]-1-piperidinyl]methyl]-2-phenylmethyl-1-piperidinecarboxamide Prepared according to procedures described in Example 83 with modification at Step G. MS (ESI) 572 (M+H).

Example 85

Preparation of (+/−)-(trans)-N-(4-fluorophenyl)-3-[[4-[(4-fluorophenyl)methyl]-1-piperidinyl]methyl]-2-phenylmethyl-1-piperidinecarboxamide Prepared according to procedures described in Example 83 with modification at Step G. MS (ESI) 518 (M+H).

Example 86

Preparation of (+/−)-(trans)-N-(3-methoxyphenyl)-3-[[4-[(4-fluorophenyl)methyl]-1-piperidinyl]methyl]-2-phenylmethyl-1-piperidinecarboxamide Prepared according to procedures described in Example 83 with modification at Step G. MS (ESI) 530 (M+H).

Example 87

Preparation of (+/−)-(trans)-N-(3-acetylphenyl)-3-[[4-[(4-fluorophenyl)methyl]-1-piperidinyl]methyl]-2-phenylmethyl-1-piperidinecarboxamide Prepared according to procedures described in Example 83 with modification at Step G. MS (ESI) 542 (M+H).

Example 88

Preparation of (+)-N-(3-methoxyphenyl)-3-[[4-(phenylmethyl)-1-piperidinyl]methyl]-1-piperidinecarboxamide and

Example 89

Preparation of (−)-N-(3-methoxyphenyl)-3-[[4-(phenylmethyl)-1-piperidinyl]methyl]-1-piperidinecarboxamide Prepared according to procedures described in Example 37 with the added step of resolving the enantiomers by HPLC. The racemic mixture was separated by a Chiracel OD column (20 mM by 250 mM) at 7 mLs per min with 20% isopropyl alcohol in hexanes. MS (ESI) 422 (M+H).

Example 90

Preparation of (+/−)-N-(phenyl)-3-[[4-[(4-fluorophenyl)methyl]-1-piperidinyl]methyl]-3,4-dihydro-2(1H)isoquinolinecarboxamide Part A. Preparation of (+/−)-N-(t-butoxycarbonyl)-3-carboxy-3,4-dihydro-2(1H)-isoquinoline.

To a solution of (+/−)-3-carboxy-3,4-dihydro-2(1H)-isoquinoline (9.61 g) in 200 mL of THF was added triethyl amine (6.9 mL). After stirring for 5 minutes, the solution was cooled to 0° C. and the reaction charged with 10.32 g of di-t-butyl dicarbonate. The resulting mixture was stirred for 12 hours and then concentrated in vacuo. The resulting residue was washed with hexanes and the washes concentrated in vacuo. Purification of the residue using flash chromatography (silica, 0–50% EtOAc/hexanes) provided 2.7 g of (+/−)-N-(t-butoxycarbonyl)-3-carboxy-3,4-dihydro-2(1H)-isoquinoline.

Part B. Preparation of (+/−)-N-(t-butoxycarbonyl)-3-hydroxymethyl-3,4-dihydro-2(1H)-isoquinoline.

To a 0° C. solution of $LiAlH_4$ in THF (1M, 9.36 mL) was added (+/−)-N-(t-butoxycarbonyl)-3-carboxy-3,4-dihydro-2(1H)-isoquinoline (2.5 g) dropwise in 4 mL of ether. After 15 minutes, the reaction was quenched by the successive dropwise addition of water (0.35 mL), 15% NaOH (0.35 mL) and water (1 mL). The reaction mixture was then filtered and the filter cake rinsed thoroughly with ether. The combined organic layer was dried over magnesium sulfate, filtered and concentrated in vacuo. Purification of the residue using flash chromatography (silica, 0–25% EtOAc/hexanes) provided 0.841 g of (+/−)-N-(t-butoxycarbonyl)-3-hydroxymethyl-3,4-dihydro-2(1H)-isoquinoline.

Part C. Preparation of (+/−)-N-(t-butoxycarbonyl)-3-carboxyaldehyde-3,4-dihydro-2(1H)-isoquinoline.

A 500 mL flask was charged with 3.5 g of 4 Å molecular sieves and heated under vacuum at >100° C. for 10 minutes. After cooling to room temperature, the flask was charged with 50 mL of $CH_2Cl_2$; 0.515 g of NMO and 0.780 g of of (+/−)-N-(t-butoxycarbonyl)-3-hydroxymethyl-3,4-dihydro-2(1H)-isoquinoline. The resulting slurry was charged with TPAP (0.053 g) at 0° C. and allowed to warm to room temperature. After 90 minutes the reaction mixture was filtered through silica gel with EtOAc and concentrated in vacuo. The residue was purified using flash chromatography (silica gel, 0–25% EtOAc/hexanes) to provide 0.700 g of (+/−)-N-(t-butoxycarbonyl)-3-carboxyaldehyde-3,4-dihydro-2(1H)-isoquinoline. Mass spectrum [ESI], $[(M+H)^+]$=458.\

Part D. Preparation of (+/−)-N-(phenyl)-3-[[4-[(4-fluorophenyl)methyl]-1-piperidinyl]methyl]-3,4-dihydro-2(1H)isoquinolinecarboxamide.

The titled compound was synthesized from the product of Part D following the procedures outlined in Example 1, Parts E–H. Mass spectrum [ESI], $[(M+H)^+]$=458.

Example 91

Preparation of (+/−)-N-(3-cyanophenyl)-3-[[4-[(4-fluorophenyl)methyl]-1-piperidinyl]methyl]-3,4-dihydro-2(1H)isoquinolinecarboxamide Prepared according to procedures described in Example 90 with modification at Step H. Mass spectrum [ESI], $[(M+H)^+]$=483.

Example 92

Preparation of (+/−)-N-(3-methoxyphenyl)-3-[[4-[(4-fluorophenyl)methyl]-1-piperidinyl]methyl]-3,4-dihydro-2(1H)isoquinolinecarboxamide Prepared according to procedures described in Example 90 with modification at Step H. Mass spectrum [ESI], $[(M+H)^+]$=488.

Example 93

Preparation of (+/−)-N-(4-cyanophenyl)-3-[[4-[(4-fluorophenyl)methyl]-1-piperidinyl]methyl]-3,4-dihydro-2(1H)isoquinolinecarboxamide Prepared according to procedures described in Example 90 with modification at Step H. Mass spectrum [ESI], $[(M+H)^+]$=483.

Example 94

Preparation of (+/−)-N-(4-fluorophenyl)-3-[[4-[(4-fluorophenyl)methyl]-1-piperidinyl]methyl]-3,4-dihydro-2(1H)isoquinolinecarboxamide Prepared according to procedures described in Example 90 with modification at Step H. Mass spectrum [ESI], $[(M+H)^+]$=476.

Example 95

Preparation of (+/−)-3-[[4-[(4-fluorophenyl)methyl]-1-piperidinyl]methyl]-1,2,3,4-tetrahydro-2-(phenylacetyl)isoquinoline Prepared according to procedures described in Example 22 from starting materials made according to Example 90, Parts A–G. Mass spectrum [ESI], $[(M+H)^+]$=457.

Example 96

Preparation of (+/−)-3-[[4-[(4-fluorophenyl)methyl]-1-piperidinyl]methyl]-1,2,3,4-tetrahydro-2-(phenylmethylsulfonyl)isoquinoline Prepared according to procedures described in Example 22 from starting materials made according to Example 90, Parts A–G. Mass spectrum [ESI], $[(M+H)^+]$=493

Example 97

Preparation of (+/−)-Phenyl-3-[[4-[(4-fluorophenyl)methyl]-1-piperidinyl]methyl]-3,4-dihydro-2(1H)isoquinolinecarboxylate Prepared according to procedures described in Example 22 from starting materials made according to Example 90, Parts A–G. Mass spectrum [ESI], $[(M+H)^+]$=459.

Example 98

Preparation of (+/−)-N-(phenyl)-3-[2-[4-[(4-fluorophenyl)methyl]-1-piperidinyl]ethyl]-3,4-dihydro-2(1H)-isoquinolinecarboxamide Part A. Preparation of N-(t-butoxycarbonyl)-2-methyl-benzylamine.

To a 0° C. solution of 2-methyl-benzylamine (10 g) in 400 mL of THF was added di-t-butyl dicarbonate (18.9 g). The resulting solution was stirred at room temperature for 12 hours. Concentration in vacuo followed by crystallization with cold (−78° C.) hexanes provided 17.0 g of N-(t-butoxycarbonyl)-2-methyl-benzylamine. Mass spectrum [NH$_3$/CI], [(M+H)$^+$]=222.

Part B. Preparation of (+/−)-N-(t-butoxycarbonyl)-3-hydroxy-3,4-dihydro-2(1H)-isoquinoline.

To a −78° C. solution of N-(t-butoxycarbonyl)-2-methyl-benzylamine (2 g) in 100 mL of THF was added dropwise 15.3 mL (1.3M) of s-BuLi. The resulting mixture was stirred at −30° C. for 30 minutes. The intermediate anion was quenched by the addition of DMF (1.05 mL) and the reaction stirred at room temperature for 90 minutes. The reaction mixture was quenched with water, diluted with ether and the organic layer washed with brine. The resulting organic layer was dried over sodium sulfate, filtered, concentrated in vacuo and the residue purified using flash chromatogtraphy (silica, 0–25% EtOAc/hexanes) to provide 1.36 g of (+/−)-N-(t-butoxycarbonyl)-3-hydroxy-3,4-dihydro-2(1H)-isoquinoline. Mass spectrum [NH$_3$/CI], [(M+H)$^+$]=250.

Part C. Preparation of (+/−)-N-(t-butoxycarbonyl)-3-(2-propenyl)-3,4-dihydro-2(1H)-isoquinoline.

To a 0° C. solution of (+/−)-N-(t-butoxycarbonyl)-3-hydroxy-3,4-dihydro-2(1H)-isoquinoline (0.650 g) in 25 mL of CH$_2$Cl$_2$ was added successively allyltributyl tin (2.43 mL) and BF$_3$.Et$_2$O (10 drops). After 30 minutes at 0° C. the reaction was diluted with ether and washed with water. The organic layer was dried over sodium sulfate, filtered, concentrated in vacuo and the residue purified using flash chromatography (silica, 0–25% EtOAc/hexanes) to provide 0.580 g of (+/−)-N-(t-butoxycarbonyl)-3-(2-propenyl)-3,4-dihydro-2(1H)-isoquinoline.

Part D. Preparation of (+/−)-N-(t-butoxycarbonyl)-3-(2-ethylcarboxaldehyde)-3,4-dihydro-2(1H)-isoquinoline.

To a solution of (+/−)-N-(t-butoxycarbonyl)-3-(2-propenyl)-3,4-dihydro-2(1H)-isoquinoline (0.550 g) in 24 mL of acetone and 12 mL of t-butanol was added 12.6 mL (0.016 M in water) of OsO4. To this mixture was added 0.258 g of 4-methylmorpholine-N-oxide. The reaction was stirred for 90 minutes, diluted with water and EtOAc, and quenched by the addition of solid Na$_2$SO$_3$. The resulting organic layer was washed with water and brine, dried over sodium sulfate, filtered and concentrated in vacuo. The residue was dissolved in THF (6 mL) and water (2 mL) and treated with 0.471 g of sodium periodate. After stirring for 60 minutes, the resulting solution was poured into EtOAc and washed with water and brine. The organic layer was dried over sodium sulfate, filtered and concentrated in vacuo. The residue was purified via flash chromatography (silica, 0–25% EtOAc/hexanes) to provide 0.425 g of (+/−)-N-(t-butoxycarbonyl)-3-(2-ethylcarboxaldehyde)-3,4-dihydro-2(1H)-isoquinoline.

Part E. Preparation of (+/−)-N-(phenyl)-3-[2-[4-[(4-fluorophenyl)methyl]-1-piperidinyl]ethyl]-3,4-dihydro-2(1H)-isoquinolinecarboxamide.

The titled compound was synthesized from the product of Part D following the procedures outlined in Example 1, Parts E-H. Mass spectrum [ESI], [(M+H)$^+$]=472.

Example 99

Preparation of (+/−)-N-(3-methoxyphenyl)-3-[2-[4-[(4-fluorophenyl)methyl]-1-piperidinyl]ethyl]-3,4-dihydro-2(1H)-isoquinolinecarboxamide Prepared according to procedures described in Example 98 with modification at Step H. Mass spectrum [ESI], [(M+H)$^+$]=502.

Example 100

Preparation of (+/−)-N-(3-cyanophenyl)-3-[2-[4-[(4-fluorophenyl)methyl]-1-piperidinyl]ethyl]-3,4-dihydro-2(1H)-isoquinolinecarboxamide Prepared according to procedures described in Example 98 with modification at Step H. Mass spectrum [ESI], [(M+H)$^+$]=497.

Example 101

Preparation of (+/−)-N-(3-carboethoxyphenyl)-3-[2-[4-[(4-fluorophenyl)methyl]-1-piperidinyl]ethyl]-3,4-dihydro-2(1H)-isoquinolinecarboxamide Prepared according to procedures described in Example 98 with modification at Step H. Mass spectrum [ESI], [(M+H)$^+$]=544.

Example 102

Preparation of (+/−)-3-[[4-[(4-fluorophenyl)methyl]-1-piperidinyl]ethyl]-1,2,3,4-tetrahydro-2-(phenylmethylsulfonyl)isoquinoline Prepared according to procedures described in Example 22 from starting materials made according to Example 98, Parts A–G. Mass spectrum [ESI], [(M+H)$^+$]=507.

Example 103

Preparation of (+/−)-Phenyl-3-[2-[4-[(4-fluorophenyl)methyl]-1-piperidinyl]ethyl]-3,4-dihydro-2(1H)-isoquinolinecarboxylate Prepared according to procedures described in Example 22 from starting materials made according to Example 98, Parts A–G. Mass spectrum [ESI], [(M+H)$^+$]=473.

Example 104

Preparation of (+/−)-N-(3-cyanophenyl)-3-[2-[4-[(phenyl)methyl]-1-piperidinyl]ethyl]-3,4-dihydro-2(1H)-isoquinolinecarboxamide Prepared according to procedures described in Example 98 with modification at Step E. Mass spectrum [ESI], [(M+H)$^+$]=479.

Example 105

Preparation of (+/−)-N-(4-fluorophenyl)-3-[2-[4-[(phenyl)methyl]-1-piperidinyl]ethyl]-3,4-dihydro-2(1H)-isoquinolinecarboxamide Prepared according to procedures described in Example 104 with modification at Step H. Mass spectrum [ESI], [(M+H)$^+$]=472.

Example 106

Preparation of (+/−)-N-(phenyl)-3-[2-[4-[(phenyl)methyl]-1-piperidinyl]ethyl]-3,4-dihydro-2(1H)-isoquinolinecarboxamide Prepared according to procedures described in Example 104 with modification at Step H. Mass spectrum [ESI], [(M+H)$^+$]=454.

Example 107

Preparation of (+/−)-N-(3-methoxyphenyl)-3-[2-[4-[(phenyl)methyl]-1-piperidinyl]ethyl]-3,4-dihydro-2(1H)-isoquinolinecarboxamide Prepared according to procedures described in Example 104 with modification at Step H. Mass spectrum [ESI], [(M+H)$^+$]=484.

Example 108

Preparation of (+/−)-N-(3-carboethoxyphenyl)-3-[2-[4-[(phenyl)methyl]-1-piperidinyl]ethyl]-3,4-dihydro-2(1H)-isoquinolinecarboxamide Prepared according to procedures described in Example 104 with modification at Step H. Mass spectrum [ESI], [(M+H)$^+$]=526.

Example 109

Preparation of (+/−)-3-[[4-[(phenyl)methyl]-1-piperidinyl]ethyl]-1,2,3,4-tetrahydro-2-(phenylsulfonyl)isoquinoline Prepared according to procedures described in Example 104 with modification at Step H. Mass spectrum [ESI], [(M+H)$^+$]=475.

Example 110

Preparation of (+/−)-3-[[4-[(phenyl)methyl]-1-piperidinyl]ethyl]-1,2,3,4-tetrahydro-2-(2-thiophenesulfonyl)isoquinoline Prepared according to procedures described in Example 104 with modification at Step H. Mass spectrum [ESI], [(M+H)$^+$]=481.

Example 111

Preparation of (+/−)-3-[[4-[(phenyl)methyl]-1-piperidinyl]ethyl]-1,2,3,4-tetrahydro-2-(phenacetyl)isoquinoline Prepared according to procedures described in Example 104 with modification at Step H. Mass spectrum [ESI], [(M+H)$^+$]=439.

Example 112

Preparation of (+/−)-N-(phenyl)-4-[2-[4-(phenylmethyl)-1-piperidinyl]ethyl]-3,4-dihydro-2(1H)-isoquinolinecarboxamide Part A. Preparation of 4-(2-propenyl)-isoquinoline.

To a solution of 4-bromoisoquinoline (2.0 g) in 70 mL of toluene was added allyl tributyl stannane (3.28 mL) and Pd(PPh$_3$)$_4$ (1.10 g). The resulting solution was heated at reflux for 12 hours and then cooled to room temperature. The solution was concentrated in vacuo, dissolved in ether and washed successively with an aqueous solution of trithiocyanuric acid trisodium salt, water and brine. The organic layer was then dried over magnesium sulfate, filtered, concentrated in vacuo, and purified using flash chromatography (silica, 0–30% EtOAc/hexanes) to provide 0.965 g of 4-(2-propenyl)-isoquinoline. Mass spectrum [NH$_3$/CI], (M+H)$^+$=170.

Part B. Preparation of (+/−)-4-(2-propenyl)-3,4-dihydro-2(1H)-isoquinoline.

To a solution of 4-(2-propenyl)-isoquinoline (3.10 g) in 40 mL of THF was added L-Selectride' (40.3 mL of a 1M solution in THF) dropwise over 20 minutes. After stirring an additional 60 minutes, the reaction was quenched by the careful addition of methanol (10 mL). The resulting mixture was poured into a bilayer of ether and 1N HCl. The aqueous layer was neutralized by the careful addition of solid NaHCO$_3$ and extracted with three portions of CH$_2$Cl$_2$. The combined organic layer was washed with water and brine, dried over magnesium sulfate, filtered and concentrated in vacuo to provide crude of (+/−)-4-(2-propenyl)-3,4-dihydro-2(1H)-isoquinoline (2.40 g). Mass spectrum [NH$_3$/CI], (M+H)$^+$=174.

Part C. Preparation of (+/−)-N-(t-butoxycarbonyl)-4-(2-propenyl)-3,4-dihydro-2(1H)-isoquinoline.

To a 0° C. solution of crude of (+/−)-4-(2-propenyl)-3,4-dihydro-2(1H)-isoquinoline (2.35 g) in 30 mL of CH$_2$Cl$_2$ was added triethyl amine (3.97 mL) and DMAP (0.166 g). After stirring for 5 minutes, the reaction was charged with 4.16 g of di-t-butyl dicarbonate. The resulting mixture was stirred for 2 hours at room temperature. The reaction mixture was then washed with 1N HCl, saturated NaHCO$_3$, and brine. The organic layer was dried over magnesium sulfate, filtered and concentrated in vacuo. Purification of the residue using flash chromatography (silica, 0–10% EtOAc/hexanes) provided 3.48 g of (+/−)-N-(t-butoxycarbonyl)-4-(2-propenyl)-3,4-dihydro-2(1H)-isoquinoline. Mass spectrum [NH$_3$/CI], (M+H)$^+$=274.

Part D. Preparation of (+/−)-N-(phenyl)-4-[2-[4-(phenylmethyl)-1-piperidinyl]ethyl]-3,4-dihydro-2(1H)-isoquinolinecarboxamide.

The titled compound was synthesized from the product of Part C following the procedures outlined in Example 98, Parts E-H. Mass spectrum [NH$_3$/CI], [(M+H)$^+$]=454

Example 113

Preparation of (+/−)-N-(3-cyanophenyl)-4-[2-[4-(phenylmethyl)-1-piperidinyl]ethyl]-3,4-dihydro-2(1H)-isoquinolinecarboxamide Prepared according to procedures described in Example 112 with modification at Step H. Mass spectrum [ESI], [(M+H)$^+$]=479.

Example 114

Preparation of (+/−)-N-(4-fluorophenyl)-4-[2-[4-(phenylmethyl)-1-piperidinyl]ethyl]-3,4-dihydro-2(1H)-isoquinolinecarboxamide Prepared according to procedures described in Example 112 with modification at Step H. Mass spectrum [NH3/CI], [(M+H)$^+$]=472.

Example 115

Preparation of (+/−)-N-(3-methoxyphenyl)-4-[2-[4-(phenylmethyl)-1-piperidinyl]ethyl]-3,4-dihydro-2(1H)-isoquinolinecarboxamide Prepared according to procedures described in Example 112 with modification at Step H. Mass spectrum [NH3/CI], [(M+H)$^+$]=484.

Example 116

Preparation of (+/−)-4-[2-[4-(phenylmethyl)-1-piperidinyl]ethyl]-3,4-dihydro-2(1H)phenylsulfonyl isoquinoline Prepared according to procedures described in Example 112 with modification at Step H. Mass spectrum [NH$_3$/CI], [(M+H)$^+$]=475.

Example 117

Preparation of (+/−)-Phenyl-4-[2-[4-(phenylmethyl)-1-piperidinyl]ethyl]-3,4-dihydro-2(1H)-isoquinolinecarboxylate Prepared according to procedures described in Example 112 with modification at Step H. Mass spectrum [NH$_3$/CI], [(M+H)$^+$]=455.

Example 118

Preparation of (+/−)-4-[2-[4-(phenylmethyl)-1-piperidinyl]ethyl]-3,4-dihydro-2(1H)phenacetyl isoquinoline Prepared according to procedures described in Example 112 with modification at Step H. Mass spectrum [NH$_3$/CI], [(M+H)$^+$]=439

Example 119

Preparation of (+/−)-N-(3-cyanophenyl)-4-[2-[4-(4-fluorophenylmethyl)-1-piperidinyl]ethyl]-3,4-dihydro-2(1H)-isoquinolinecarboxamide Prepared according to procedures described in Example 112 with modification at Step E. Mass spectrum [ESI], [(M+H)$^+$]=497.

Example 120

Preparation of (+/−)-N-(4-carbethoxyphenyl)-4-[2-[4-(4-fluorophenylmethyl)-1-piperidinyl]ethyl]-3,4-dihydro-2(1H)-isoquinolinecarboxamide Prepared according to procedures described in Example 119 with modification at Step H. Mass spectrum [ESI], [(M+H)$^+$]=544.

Example 121

Preparation of (+/−)-N-(4-fluorophenyl)-4-[2-[4-(phenylmethyl)-1-piperidinyl]ethyl]-3,4-dihydro-2(1H)-isoquinolinecarboxamide Prepared according to procedures described in Example 119 with modification at Step H. Mass spectrum [ESI], [(M+H)$^+$]=490.

Example 122

Preparation of (+/−)-4-[2-[4-(4-fluorophenylmethyl)-1-piperidinyl]ethyl]-3,4-dihydro-2(1H)-[phenyl]sulfonyl isoquinoline Prepared according to procedures described in Example 119 with modification at Step H. Mass spectrum [ESI], [(M+H)$^+$]=493.

Example 123

Preparation of (+/−)-4-[2-[4-(4-fluorophenylmethyl)-1-piperidinyl]ethyl]-3,4-dihydro-2(1H)[phenacetyl]isoquinoline Prepared according to procedures described in Example 119 with modification at Step H. Mass spectrum [ESI], [(2M+H)$^+$]=913.

Example 124

Preparation of (+/−)-4-[2-[4-(4-fluorophenylmethyl)-1-piperidinyl]ethyl]-3,4-dihydro-2(1H)-[phenylmethyl]sulfonyl isoquinoline Prepared according to procedures described in Example 119 with modification at Step H. Mass spectrum [NH$_3$/CI], [(M+H)$^+$]=507.

Example 125

Preparation of (2R)-2-{[4-(4-fluorobenzyl)-1-piperidinyl]methyl}-4-[(2R)-3,3,3-trifluoro-2-methoxy-2-phenylpropanoyl]morpholine Prepared according to procedures described in Example 58. MS (ESI) 509 (M+H).

Example 126

Preparation of (2R)-N-(3-acetylphenyl)-2-{[4-(4-fluorobenzyl)-1-piperidinyl]methyl}-4-morpholinecarboxamide Prepared according to procedures described in Example 58. MS (ESI) 454 (M+H).

Example 127

Preparation of (2R)-2-{[4-(4-fluorobenzyl)-1-piperidinyl]methyl}-N-(3-methoxyphenyl)-4-morpholinecarboxamide Prepared according to procedures described in Example 58. MS (ESI) 442 (M+H).

Example 128

Preparation of (2R)-N-(3-cyanophenyl)-2-{[4-(4-fluorobenzyl)-1-piperidinyl]methyl}-4-morpholinecarboxamide Prepared according to procedures described in Example 58. MS (ESI) 437 (M+H).

Example 129

Preparation of (2R)-2-{[4-(4-fluorobenzyl)-1-piperidinyl]methyl}-N-(4-fluorophenyl)-4-morpholinecarboxamide Prepared according to procedures described in Example 58. MS (ESI) 430 (M+H).

Example 130

Preparation of (2R)-2-{[4-(4-fluorobenzyl)-1-piperidinyl]methyl}-N-phenyl-4-morpholinecarboxamide Prepared according to procedures described in Example 58. MS (ESI) 412 (M+H).

Example 131

Preparation of (2R)-N-(3-cyanophenyl)-2-{[(3S)-3-(4-fluorobenzyl)piperidinyl]methyl}-4-morpholinecarboxamide Prepared according to procedures described in Example 58. MS (ESI) 437 (M+H).

Example 132

Preparation of (2R)-N-(3-acetylphenyl)-2-{[(3S)-3-(4-fluorobenzyl)piperidinyl]methyl}-4-morpholinecarboxamide Prepared according to procedures described in Example 58. MS (ESI) 453 (M+H).

Example 133

Preparation of (2R)-N-(3-acetylphenyl)-2-{[(3S)-3-(4-fluorobenzyl)piperidinyl]methyl}-N-phenyl-4-morpholinecarboxamide Prepared according to procedures described in Example 58. MS (ESI) 412 (M+H).

Example 134

Preparation of 3-{[3-(4-fluorobenzyl)-1-pyrrolidinyl]methyl}-N-phenyl-1-piperidinecarboxamide Prepared according to procedures described in Example 1. MS (ESI) 396 (M+H).

Example 135

Preparation of N-(3-cyanophenyl)-3-{[3-(4-fluorobenzyl)-1-pyrrolidinyl]methyl}-1-piperidinecarboxamide Prepared according to procedures described in Example 1. MS (ESI) 421 (M+H).

Example 136

Preparation of N-(3-acetylphenyl)-3-{[3-(4-fluorobenzyl)-1-pyrrolidinyl]methyl}-1-piperidinecarboxamide Prepared according to procedures described in Example 1. MS (ESI) 438 (M+H).

Example 137

Preparation of 3-{[(3S)-3-(4-fluorobenzyl)piperidinyl]methyl}-N-phenyl-1-piperidinecarboxamide Prepared according to procedures described in Example 1. MS (ESI) 410 (M+H).

Example 138

Preparation of N-(3-cyanophenyl)-3-{[(3S)-3-(4-fluorobenzyl)piperidinyl]methyl}-1-piperidinecarboxamide Prepared according to procedures described in Example 1. MS (ESI) 435 (M+H).

Example 139

Preparation of N-(3-acetylphenyl)-3-{[(3S)-3-(4-fluorobenzyl)piperidinyl]methyl}-1-piperidinecarboxamide Prepared according to procedures described in Example 1. MS (ESI) 452 (M+H).

Example 140

Preparation of tert-butyl 4-[(3-cyanoanilino)carbonyl]-2-{[4-(4-fluorobenzyl)-1-piperidinyl]methyl}-1-piperazinecarboxylate Step A. Preparation of 1-tert-butyl-4-(9H-fluoren-9-ylmethyl)-2-hydroxymethyl-1,4-piperazine dicarboxylate.

To a stirring solution of 1-(tert-butoxycarbonyl)-4-[(9H-fluoren-9-ylmethoxy)carbonyl]-2-piperazinecarboxylic acid (5000 mg, 11.1 mmol, prepared according to procedures in Wu, M. T., et. al. *Bioorg. Med. Chem. Lett.* 1993, 3, 2023) in dry THF (80 mL) was added a 1M solution of borane (22 mL) in THF. The reaction was stirred for 5 h and then heated to reflux for 21 h. After cooling to room temperature, the reaction was quenched by the addition of 1M solution of HCl (80 mL). The reaction was extracted with EtOAc (3×100 mL). The organic layers were combined, dried over Na$_2$SO$_4$, and conc. in vacuo to an oil. The oil was purified by flash chromatography (SiO$_2$, 2:1, hexanes:EtOAc) to yield 2762 mg of 1-tert-butyl-4-(9H-fluoren-9-ylmethyl)-2-hydroxymethyl-1,4-piperazine dicarboxylate as a white solid. MS (ESI) 461 (M+Na).

Step B. Preparation of 1-tert-butyl-4-(9H-fluoren-9-ylmethyl)-2-formyl-1,4-piperazine dicarboxylate.

To a stirring solution 1-tert-butyl-4-(9H-fluoren-9-ylmethyl)-2-hydroxymethyl-1,4-piperazine dicarboxylate (2500 mg, 5.71 mmol) in dry CH$_2$Cl$_2$ (250 mL) was added 4 angstrom molecular sieves (100 mg) and N-methyl-morpholine oxide (1002 mg, 8.57 mmol, Aldrich). After 10 min, tetrapropylammonium perruthenate oxide (100 mg, 0.29 mmol, Aldrich) and the reaction was stirred for 1 h. The reaction was filtered thruough a pad of silica gel and the silica gel was washed with EtOAc. The organic layers were combined and conc. in vacuo to a colorless oil of 2415 mg that was used without further purification. MS (ESI) 437 (M+H).

Step C. Preparation of 1-tert-butyl-4-(9H-fluoren-9-ylmethyl)-2-{[4-(4-fluorobenzyl)-1-piperidinyl]methyl}-1,4-piperazine dicarboxylate.

A solution of 1-tert-butyl-4-(9H-fluoren-9-ylmethyl)-2-formyl-1,4-piperazine dicarboxylate (2400 mg, 5.5 mmol) and 4-(4-flourophenylmethyl)piperidine hydrochloride (1259 mg, 5.5 mmol) in dry CH$_2$Cl$_2$ (250 mL) was stirred for 15 min when sodium triacetoxyborohydride (1696 mg, 8.0 mmol, Aldrich) was added. The reaction was stirred for 2 h and then quenched with water (200 mL). The organic layer was separated, dried over MgSO$_4$, and conc. in vacuo to a white solid. The solid was purified by flash chromatography (SiO2, hexanes:EtOAc, 2:1) to yield 2271 mg of 1-tert-butyl-4-(9H-fluoren-9-ylmethyl)-2-{[4-(4-fluorobenzyl)-1-piperidinyl]methyl}-1,4-piperazine dicarboxylate as a white solid. MS (ESI) 614 (M+H).

Step D. Preparation of 1-tert-butyl-2-{[4-(4-fluorobenzyl)-1-piperidinyl]methyl}-1-piperazine carboxylate.

To a stirring solution of 1-tert-butyl-4-(9H-fluoren-9-ylmethyl)-2-{[4-(4-fluorobenzyl)-1-piperidinyl]methyl}-1,4-piperazine dicarboxylate (2115 mg, 3.45 mmol) in dry CH$_2$Cl$_2$ (30 mL) was added piperidine (5 mL, Aldrich). The reaction was allowed to stir for 3 h and conc. in vacuo to a pale yellow solid. The solid was purified by flash chromatography (SiO2, EtOAc then CH$_2$Cl$_2$:MeOH:TEA, 90:5:5) to yield 1340 mg of 1-tert-butyl-2-{[4-(4-fluorobenzyl)-1-piperidinyl]methyl}-1-piperazine carboxylate as a white solid. MS (ESI) 392 (M+H).

Step E. Preparation of tert-butyl 4-[(3-cyanoanilino)carbonyl]-2-{[4-(4-fluorobenzyl)-1-piperidinyl]methyl}-1-piperazinecarboxylate.

To a stirring solution 1-tert-butyl-2-{[4-(4-fluorobenzyl)-1-piperidinyl]methyl}-1-piperazine carboxylate (20 mg, 0.05 mmol) in dry THF (0.3 mL) was added 3-cyanophenyl isocyante (9.2 mg, 0.06 mmol, Aldrich). The reaction was stirred for 30 min and the quenched by the addition of methanol (0.3 mL). The reaction conc. in vacuo to a white solid. The solid was purified by radial chromatography (SiO2, hexanes:EtOAc, 2:1) to yield 22.1 mg of tert-butyl 4-[(3-cyanoanilino)carbonyl]-2-{[4-(4-fluorobenzyl)-1-piperidinyl]methyl}-1-piperazinecarboxylate as a white solid. MS (ESI) 536 (M+H).

Example 141

Preparation of N-(3-cyanophenyl)-3-{[4-(4-fluorobenzyl)-1-piperidinyl]methyl}-1-piperazinecarboxamide dihydrochloride Tert-butyl 4-[(3-cyanoanilino)carbonyl]-2-{[4-(4-fluorobenzyl)-1-piperidinyl]methyl}-1-piperazinecarboxylate (13.4 mg, 0.025 mmol) was dissolved in 4M HCl in dioxane (1 mL). The reaction was stirred for 1 h and conc. in vacuo to a yield 12.7 mg of N-(3-cyanophenyl)-3-{[4-(4-fluorobenzyl)-1-piperidinyl]methyl}-1-piperazinecarboxamide dihydrochloride as a white solid. MS (ESI) 436 (M–HCl—Cl).

Example 142

Preparation of 4-benzyl-N-(3-cyanophenyl)-3-{[4-(4-fluorobenzyl)-1-piperidinyl]methyl}-1-piperazinecarboxamide A solution of N-(3-cyanophenyl)-3-{[4-(4-fluorobenzyl)-1-piperidinyl]methyl}-1-piperazinecarboxamide dihydrochloride (20.0 mg, 0.05 mmol) and benzaldhyde (8.5 mg, 0.08 mmol, Aldrich) in dry dichloroethane (5 mL) was stirred for 20 min when sodium triacetoxyborohydride (32 mg, 0.15 mmol, Aldrich) was added. The reaction was stirred for 16 h and then quenched with water (5 mL). The organic layer was separated, dried over MgSO$_4$, and conc. in vacuo to a white solid. The solid was purified by flash chromatography (SiO2, EtOAc and then EtOAc:TEA, 9:1) to yield 5.0 mg of 4-benzyl-N-(3-cyanophenyl)-3-{[4-(4-fluorobenzyl)-1-piperidinyl]methyl}-1-piperazinecarboxamide as a white solid. MS (ESI) 526 (M+H).

Example 143

Preparation of 4-acetyl-N-(3-acetylphenyl)-3-{[4-(4-fluorobenzyl)-1-piperidinyl]methyl}-1-piperazinecarboxamide Prepared according to procedures described in Example 143. MS (ESI) 495 (M+H).

Example 144

Preparation of tert-butyl 4-[(anilino)carbonyl]-2-{[4-(4-fluorobenzyl)-1-piperidinyl]methyl}-1-piperazinecarboxylate Prepared according to procedures described in Example 140. MS (ESI) 511 (M+H).

Example 145

Preparation of tert-butyl 4-[(3-methoxyanilino)carbonyl]-2-{[4-(4-fluorobenzyl)-1-piperidinyl]methyl}-1-piperazinecarboxylate Prepared according to procedures described in Example 140. MS (ESI) 541 (M+H).

Example 146

Preparation of tert-butyl 4-[(3-acetylanilino)carbonyl]-2-{[4-(4-fluorobenzyl)-1-piperidinyl]methyl}-1-piperazinecarboxylate Prepared according to procedures described in Example 140. MS (ESI) 553 (M+H).

Example 147

Preparation of 3-{[4-(4-fluorobenzyl)-1-piperidinyl]methyl}-N-phenyl-1-piperazinecarboxamide dihydrochloride Prepared according to procedures described in Example 141. MS (ESI) 411 (M−HCl—Cl).

Example 148

Preparation of 3-{[4-(4-fluorobenzyl)-1-piperidinyl]methyl}-N-(3-methoxyphenyl)-1-piperazinecarboxamide dihydrochloride Prepared according to procedures described in Example 141. MS (ESI) 441 (M−HCl—Cl).

Example 149

Preparation of N-(3-acetylphenyl)-3-{[4-(4-fluorobenzyl)-1-piperidinyl]methyl}-1-piperazinecarboxamide dihydrochloride Prepared according to procedures described in Example 1 141. MS (ESI) 453 (M−HCl—Cl).

Example 150

Preparation of 4-benzyl-N-(3-cyanophenyl)-3-{[4-(4-fluorobenzyl)-1-piperidinyl]methyl}-1-piperazinecarboxamide Prepared according to procedures described in Example 141. MS (ESI) 526 (M+H).

The following tables contain representative examples of the present invention, and may be prepared by procedures described above, or methods familiar to one skilled in the art. Each entry in each table is intended to be paired with each formulae at the start of the table. For example, Entry 1 in Table 1 is intended to be paired with each of formulae 1–12.

TABLE 1*

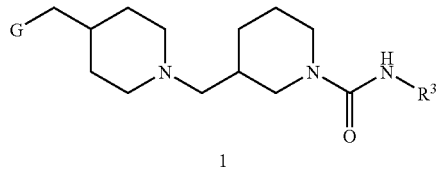

1

TABLE 1*-continued

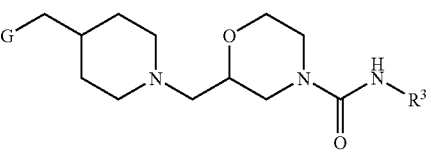

2

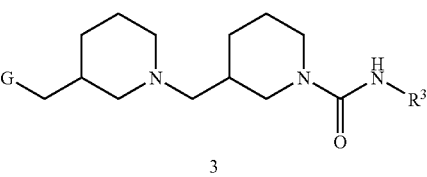

3

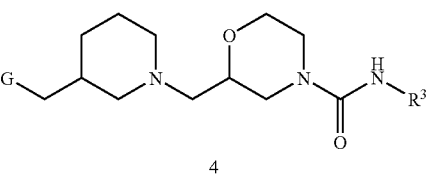

4

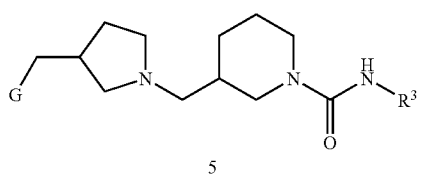

5

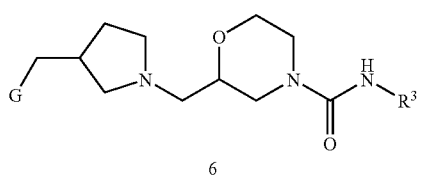

6

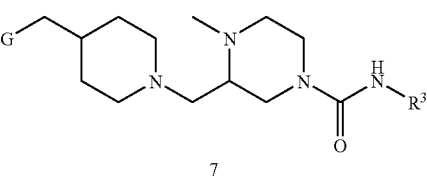

7

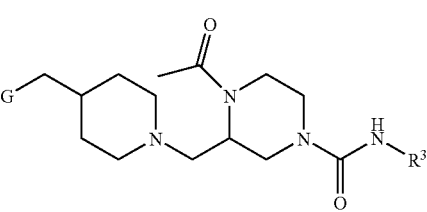

8

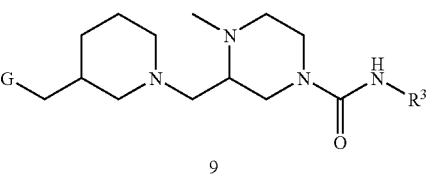

9

TABLE 1*-continued

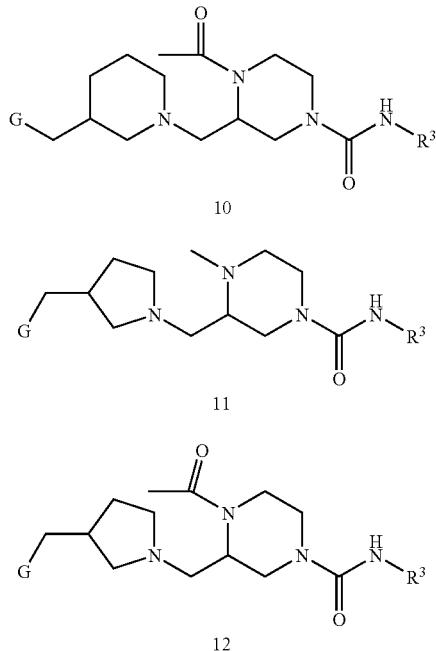

| Entry | G | R³ |
|---|---|---|
| 1 | 4-F—Ph | Ph |
| 2 | 4-F—Ph | 3-CN—Ph |
| 3 | 4-F—Ph | 3-COCH3—Ph |
| 4 | 4-F—Ph | 3-CO2Me—Ph |
| 5 | 4-F—Ph | 3-CO2Et—Ph |
| 6 | 4-F—Ph | 3-CO2H—Ph |
| 7 | 4-F—Ph | 3-CONH2—Ph |
| 8 | 4-F—Ph | 3-CONHMe—Ph |
| 9 | 4-F—Ph | 3-F—Ph |
| 10 | 4-F—Ph | 3-Cl—Ph |
| 11 | 4-F—Ph | 3-Br—Ph |
| 12 | 4-F—Ph | 3-NO2—Ph |
| 13 | 4-F—Ph | 3-NH2—Ph |
| 14 | 4-F—Ph | 3-NHMe—Ph |
| 15 | 4-F—Ph | 3-NMe2—Ph |
| 16 | 4-F—Ph | 3-NHCOCH3—Ph |
| 17 | 4-F—Ph | 3-SO2NH2—Ph |
| 18 | 4-F—Ph | 3-SO2NHMe—Ph |
| 19 | 4-F—Ph | 3-CF3—Ph |
| 20 | 4-F—Ph | 3-OCH3—Ph |
| 21 | 4-F—Ph | 3-OPh—Ph |
| 22 | 4-F—Ph | 3-OCF3—Ph |
| 23 | 4-F—Ph | 3-SCH3—Ph |
| 24 | 4-F—Ph | 3-SOCH3—Ph |
| 25 | 4-F—Ph | 3-SO2CH3—Ph |
| 26 | 4-F—Ph | 3-OH—Ph |
| 27 | 4-F—Ph | 3-CH2OH—Ph |
| 28 | 4-F—Ph | 3-CHOHCH3—Ph |
| 29 | 4-F—Ph | 3-COH(CH3)2—Ph |
| 30 | 4-F—Ph | 3-CHOHPh—Ph |
| 31 | 4-F—Ph | 3-CH3—Ph |
| 32 | 4-F—Ph | 3-C2H5—Ph |
| 33 | 4-F—Ph | 3-iPr-Ph |
| 34 | 4-F—Ph | 3-tBu-Ph |
| 35 | 4-F—Ph | 3-Ph—Ph |
| 36 | 4-F—Ph | 3-CH2Ph—Ph |
| 37 | 4-F—Ph | 3-CH2CO2Me—Ph |
| 38 | 4-F—Ph | 3-(1-piperidinyl)-Ph |
| 39 | 4-F—Ph | 3-(1-pyrrolidinyl)-Ph |
| 40 | 4-F—Ph | 3-(2-imidazolyl)-Ph |
| 41 | 4-F—Ph | 3-(1-imidazolyl)-Ph |
| 42 | 4-F—Ph | 3-(2-thiazolyl)-Ph |
| 43 | 4-F—Ph | 3-(3-pyrazolyl)-Ph |
| 44 | 4-F—Ph | 3-(1-pyrazolyl)-Ph |
| 45 | 4-F—Ph | 3-(1-tetrazolyl)-Ph |
| 46 | 4-F—Ph | 3-(5-tetrazolyl)-Ph |
| 47 | 4-F—Ph | 3-(2-pyridyl)-Ph |
| 48 | 4-F—Ph | 3-(2-thienyl)-Ph |
| 49 | 4-F—Ph | 3-(2-furanyl)-Ph |
| 50 | 4-F—Ph | 4-CN—Ph |
| 51 | 4-F—Ph | 4-COCH3—Ph |
| 52 | 4-F—Ph | 4-CO2Me—Ph |
| 53 | 4-F—Ph | 4-CO2Et—Ph |
| 54 | 4-F—Ph | 4-CO2H—Ph |
| 55 | 4-F—Ph | 4-CONH2—Ph |
| 56 | 4-F—Ph | 4-CONHMe—Ph |
| 57 | 4-F—Ph | 4-CONHPh—Ph |
| 58 | 4-F—Ph | 4-NHCONH2—Ph |
| 59 | 4-F—Ph | 4-F—Ph |
| 60 | 4-F—Ph | 4-Cl—Ph |
| 61 | 4-F—Ph | 4-Br—Ph |
| 62 | 4-F—Ph | 4-NO2—Ph |
| 63 | 4-F—Ph | 4-NH2—Ph |
| 64 | 4-F—Ph | 4-NHMe—Ph |
| 65 | 4-F—Ph | 4-NMe2—Ph |
| 66 | 4-F—Ph | 4-NHCOCH3—Ph |
| 67 | 4-F—Ph | 4-SO2NH2—Ph |
| 68 | 4-F—Ph | 4-SO2NHMe—Ph |
| 69 | 4-F—Ph | 4-CF3—Ph |
| 70 | 4-F—Ph | 4-OCH3—Ph |
| 71 | 4-F—Ph | 4-OPh—Ph |
| 72 | 4-F—Ph | 4-OCF3—Ph |
| 73 | 4-F—Ph | 4-SCH3—Ph |
| 74 | 4-F—Ph | 4-SOCH3—Ph |
| 75 | 4-F—Ph | 4-SO2CH3—Ph |
| 76 | 4-F—Ph | 4-OH—Ph |
| 77 | 4-F—Ph | 4-CH2OH—Ph |
| 78 | 4-F—Ph | 4-CHOHCH3—Ph |
| 79 | 4-F—Ph | 4-COH(CH3)2—Ph |
| 80 | 4-F—Ph | 4-CH3—Ph |
| 81 | 4-F—Ph | 4-C2H5—Ph |
| 82 | 4-F—Ph | 4-iPr-Ph |
| 83 | 4-F—Ph | 4-tBu-Ph |
| 84 | 4-F—Ph | 4-Ph—Ph |
| 85 | 4-F—Ph | 4-CH2Ph—Ph |
| 86 | 4-F—Ph | 4-CH2CO2Me—Ph |
| 87 | 4-F—Ph | 4-(1-piperidinyl)-Ph |
| 88 | 4-F—Ph | 4-(1-pyrrolidinyl)-Ph |
| 89 | 4-F—Ph | 4-(2-imidazolyl)-Ph |
| 90 | 4-F—Ph | 4-(1-imidazolyl)-Ph |
| 91 | 4-F—Ph | 4-(2-thiazolyl)-Ph |
| 92 | 4-F—Ph | 4-(3-pyrazolyl)-Ph |
| 93 | 4-F—Ph | 4-(1-pyrazolyl)-Ph |
| 94 | 4-F—Ph | 4-(1-tetrazolyl)-Ph |
| 95 | 4-F—Ph | 4-(5-tetrazolyl)-Ph |
| 96 | 4-F—Ph | 4-(2-pyridyl)-Ph |
| 97 | 4-F—Ph | 4-(2-thienyl)-Ph |
| 98 | 4-F—Ph | 4-(2-furanyl)-Ph |
| 99 | 4-F—Ph | 2-CN—Ph |
| 100 | 4-F—Ph | 2-COCH3—Ph |
| 101 | 4-F—Ph | 2-CO2Me—Ph |
| 102 | 4-F—Ph | 2-CO2Et—Ph |
| 103 | 4-F—Ph | 2-CO2H—Ph |
| 104 | 4-F—Ph | 2-CONH2—Ph |
| 105 | 4-F—Ph | 2-CONHMe—Ph |
| 106 | 4-F—Ph | 2-F—Ph |
| 107 | 4-F—Ph | 2-Cl—Ph |
| 108 | 4-F—Ph | 2-Br—Ph |
| 109 | 4-F—Ph | 2-NO2—Ph |
| 110 | 4-F—Ph | 2-NH2—Ph |
| 111 | 4-F—Ph | 2-NHMe—Ph |
| 112 | 4-F—Ph | 2-NMe2—Ph |
| 113 | 4-F—Ph | 2-NHCOCH3—Ph |
| 114 | 4-F—Ph | 2-SO2NH2—Ph |
| 115 | 4-F—Ph | 2-SO2NHMe—Ph |
| 116 | 4-F—Ph | 2-CF3—Ph |
| 117 | 4-F—Ph | 2-OCH3—Ph |
| 118 | 4-F—Ph | 2-OPh—Ph |
| 119 | 4-F—Ph | 2-OCF3—Ph |
| 120 | 4-F—Ph | 2-SCH3—Ph |
| 121 | 4-F—Ph | 2-SOCH3—Ph |
| 122 | 4-F—Ph | 2-SO2CH3—Ph |
| 123 | 4-F—Ph | 2-OH—Ph |
| 124 | 4-F—Ph | 2-CH2OH—Ph |

TABLE 1*-continued

| | | |
|---|---|---|
| 125 | 4-F—Ph | 2-CHOHCH3—Ph |
| 126 | 4-F—Ph | 2-COH(CH3)2—Ph |
| 127 | 4-F—Ph | 2-CHOHPh—Ph |
| 128 | 4-F—Ph | 2-CH3—Ph |
| 129 | 4-F—Ph | 2-C2H5—Ph |
| 130 | 4-F—Ph | 2-iPr-Ph |
| 131 | 4-F—Ph | 2-tBu-Ph |
| 132 | 4-F—Ph | 2-Ph—Ph |
| 133 | 4-F—Ph | 2-CH2Ph—Ph |
| 134 | 4-F—Ph | 2-CH2CO2Me—Ph |
| 135 | 4-F—Ph | 2-(1-piperidinyl)-Ph |
| 136 | 4-F—Ph | 2-(1-pyrrolidinyl)-Ph |
| 137 | 4-F—Ph | 2-(2-imidazolyl)-Ph |
| 138 | 4-F—Ph | 2-(1-imidazolyl)-Ph |
| 139 | 4-F—Ph | 2-(2-thiazolyl)-Ph |
| 140 | 4-F—Ph | 2-(3-pyrazolyl)-Ph |
| 141 | 4-F—Ph | 2-(1-pyrazolyl)-Ph |
| 142 | 4-F—Ph | 2-(1-tetrazolyl)-Ph |
| 143 | 4-F—Ph | 2-(5-tetrazolyl)-Ph |
| 144 | 4-F—Ph | 2-(2-pyridyl)-Ph |
| 145 | 4-F—Ph | 2-(2-thienyl)-Ph |
| 146 | 4-F—Ph | 2-(2-furanyl)-Ph |
| 147 | 4-F—Ph | 2,4-diF—Ph |
| 148 | 4-F—Ph | 2,5-diF—Ph |
| 149 | 4-F—Ph | 2,6-diF—Ph |
| 150 | 4-F—Ph | 3,4-diF—Ph |
| 151 | 4-F—Ph | 3,5-diF—Ph |
| 152 | 4-F—Ph | 2,4-diCl—Ph |
| 153 | 4-F—Ph | 2,5-diCl—Ph |
| 154 | 4-F—Ph | 2,6-diCl—Ph |
| 155 | 4-F—Ph | 3,4-diCl—Ph |
| 156 | 4-F—Ph | 3,5-diCl—Ph |
| 157 | 4-F—Ph | 3,4-diCF3—Ph |
| 158 | 4-F—Ph | 3,5-diCF3—Ph |
| 159 | 4-F—Ph | 5-Cl-2-MeO—Ph |
| 160 | 4-F—Ph | 5-Cl-2-Me—Ph |
| 161 | 4-F—Ph | 2-F-5-Me—Ph |
| 162 | 4-F—Ph | 2-F-5-NO2—Ph |
| 163 | 4-F—Ph | 3,4-OCH2O—Ph |
| 164 | 4-F—Ph | 3,4-OCH2CH2O—Ph |
| 165 | 4-F—Ph | 2-MeO-4-Me—Ph |
| 166 | 4-F—Ph | 2-MeO-5-Me—Ph |
| 167 | 4-F—Ph | 1-naphthyl |
| 168 | 4-F—Ph | 2-naphthyl |
| 169 | 4-F—Ph | 2-thienyl |
| 170 | 4-F—Ph | 3-thienyl |
| 171 | 4-F—Ph | 2-furanyl |
| 172 | 4-F—Ph | 3-furanyl |
| 173 | 4-F—Ph | 2-pyridyl |
| 174 | 4-F—Ph | 3-pyridyl |
| 175 | 4-F—Ph | 4-pyridyl |
| 176 | 4-F—Ph | 2-indolyl |
| 177 | 4-F—Ph | 3-indolyl |
| 178 | 4-F—Ph | 5-indolyl |
| 179 | 4-F—Ph | 6-indolyl |
| 180 | 4-F—Ph | 3-indazolyl |
| 181 | 4-F—Ph | 5-indazolyl |
| 182 | 4-F—Ph | 6-indazolyl |
| 183 | 4-F—Ph | 2-imidazolyl |
| 184 | 4-F—Ph | 3-pyrazolyl |
| 185 | 4-F—Ph | 2-thiazolyl |
| 186 | 4-F—Ph | 5-tetrazolyl |
| 187 | 4-F—Ph | 2-benzimidazolyl |
| 188 | 4-F—Ph | 5-benzimidazolyl |
| 189 | 4-F—Ph | 2-benzothiazolyl |
| 190 | 4-F—Ph | 5-benzothiazolyl |
| 191 | 4-F—Ph | 2-benzoxazolyl |
| 192 | 4-F—Ph | 5-benzoxazolyl |
| 193 | 4-F—Ph | 1-adamantyl |
| 194 | 4-F—Ph | 2-adamantyl |
| 195 | 4-F—Ph | t-Bu |
| 196 | 2-F—Ph | 3-CN—Ph |
| 197 | 2-F—Ph | 3-COCH3—Ph |
| 198 | 2-F—Ph | 3-CO2Me—Ph |
| 199 | 2-F—Ph | 3-CO2Et—Ph |
| 200 | 2-F—Ph | 3-CO2H—Ph |
| 201 | 2-F—Ph | 3-CONH2—Ph |
| 202 | 2-F—Ph | 3-F—Ph |
| 203 | 2-F—Ph | 3-Cl—Ph |
| 204 | 2-F—Ph | 3-NH2—Ph |
| 205 | 2-F—Ph | 3-SO2NH2—Ph |
| 206 | 2-F—Ph | 3-CF3—Ph |
| 207 | 2-F—Ph | 3-OCH3—Ph |
| 208 | 2-F—Ph | 3-OEt—Ph |
| 209 | 2-F—Ph | 3-OCF3—Ph |
| 210 | 2-F—Ph | 3-SO2CH3—Ph |
| 211 | 2-F—Ph | 3-OH—Ph |
| 212 | 2-F—Ph | 3-CH3—Ph |
| 213 | 2-F—Ph | 3-C2H5—Ph |
| 214 | 2-F—Ph | 4-CN—Ph |
| 215 | 2-F—Ph | 4-COCH3—Ph |
| 216 | 2-F—Ph | 4-CO2Me—Ph |
| 217 | 2-F—Ph | 4-CO2Et—Ph |
| 218 | 2-F—Ph | 4-CO2H—Ph |
| 219 | 2-F—Ph | 4-CONH2—Ph |
| 220 | 2-F—Ph | 4-F—Ph |
| 221 | 2-F—Ph | 4-Cl—Ph |
| 222 | 2-F—Ph | 4-NH2—Ph |
| 223 | 2-F—Ph | 4-SO2NH2—Ph |
| 224 | 2-F—Ph | 4-CF3—Ph |
| 225 | 2-F—Ph | 4-OCH3—Ph |
| 226 | 2-F—Ph | 4-OEt—Ph |
| 227 | 2-F—Ph | 4-OCF3—Ph |
| 228 | 2-F—Ph | 4-SO2CH3—Ph |
| 229 | 2-F—Ph | 4-OH—Ph |
| 230 | 2-F—Ph | 4-CH3—Ph |
| 231 | 2-F—Ph | 4-C2H5—Ph |
| 232 | 2-F—Ph | 2,4-diF—Ph |
| 233 | 2-F—Ph | 2,5-diF—Ph |
| 234 | 2-F—Ph | 3,4-diF—Ph |
| 235 | 2-F—Ph | 3,5-diF—Ph |
| 236 | 2-F—Ph | 2,4-diCl—Ph |
| 237 | 2-F—Ph | 2,5-diCl—Ph |
| 238 | 2-F—Ph | 3,4-diCl—Ph |
| 239 | 2-F—Ph | 3,5-diCl—Ph |
| 240 | 2-F—Ph | 3,4-OCH2O—Ph |
| 241 | 2-F—Ph | 3,4-OCH2CH2O—Ph |
| 242 | 2-F—Ph | 2-thienyl |
| 243 | 2-F—Ph | 2-furanyl |
| 244 | 2-F—Ph | 2-pyridyl |
| 245 | 2-F—Ph | 4-pyridyl |
| 246 | 2-F—Ph | 2-imidazolyl |
| 247 | 2-F—Ph | 3-pyrazolyl |
| 248 | 2-F—Ph | 2-thiazolyl |
| 249 | 2-F—Ph | 5-tetrazolyl |
| 250 | 2-F—Ph | 1-adamantyl |
| 251 | 2,4-diF—Ph | 3-CN—Ph |
| 252 | 2,4-diF—Ph | 3-COCH3—Ph |
| 253 | 2,4-diF—Ph | 3-CO2Me—Ph |
| 254 | 2,4-diF—Ph | 3-CO2Et—Ph |
| 255 | 2,4-diF—Ph | 3-CO2H—Ph |
| 256 | 2,4-diF—Ph | 3-CONH2—Ph |
| 257 | 2,4-diF—Ph | 3-F—Ph |
| 258 | 2,4-diF—Ph | 3-Cl—Ph |
| 259 | 2,4-diF—Ph | 3-NH2—Ph |
| 260 | 2,4-diF—Ph | 3-SO2NH2—Ph |
| 261 | 2,4-diF—Ph | 3-CF3—Ph |
| 262 | 2,4-diF—Ph | 3-OCH3—Ph |
| 263 | 2,4-diF—Ph | 3-OEt—Ph |
| 264 | 2,4-diF—Ph | 3-OCF3—Ph |
| 265 | 2,4-diF—Ph | 3-SO2CH3—Ph |
| 266 | 2,4-diF—Ph | 3-OH—Ph |
| 267 | 2,4-diF—Ph | 3-CH3—Ph |
| 268 | 2,4-diF—Ph | 3-C2H5—Ph |
| 269 | 2,4-diF—Ph | 4-CN—Ph |
| 270 | 2,4-diF—Ph | 4-COCH3—Ph |
| 271 | 2,4-diF—Ph | 4-CO2Me—Ph |
| 272 | 2,4-diF—Ph | 4-CO2Et—Ph |
| 273 | 2,4-diF—Ph | 4-CO2H—Ph |
| 274 | 2,4-diF—Ph | 4-CONH2—Ph |
| 275 | 2,4-diF—Ph | 4-F—Ph |
| 276 | 2,4-diF—Ph | 4-Cl—Ph |
| 277 | 2,4-diF—Ph | 4-NH2—Ph |
| 278 | 2,4-diF—Ph | 4-SO2NH2—Ph |
| 279 | 2,4-diF—Ph | 4-CF3—Ph |
| 280 | 2,4-diF—Ph | 4-OCH3—Ph |
| 281 | 2,4-diF—Ph | 4-OEt—Ph |
| 282 | 2,4-diF—Ph | 4-OCF3—Ph |

TABLE 1*-continued

| | | |
|---|---|---|
| 283 | 2,4-diF—Ph | 4-SO2CH3—Ph |
| 284 | 2,4-diF—Ph | 4-OH—Ph |
| 285 | 2,4-diF—Ph | 4-CH3—Ph |
| 286 | 2,4-diF—Ph | 4-C2H5—Ph |
| 287 | 2,4-diF—Ph | 2,4-diF—Ph |
| 288 | 2,4-diF—Ph | 2,5-diF—Ph |
| 289 | 2,4-diF—Ph | 3,4-diF—Ph |
| 290 | 2,4-diF—Ph | 3,5-diF—Ph |
| 291 | 2,4-diF—Ph | 2,4-diCl—Ph |
| 292 | 2,4-diF—Ph | 2,5-diCl—Ph |
| 293 | 2,4-diF—Ph | 3,4-diCl—Ph |
| 294 | 2,4-diF—Ph | 3,5-diCl—Ph |
| 295 | 2,4-diF—Ph | 3,4-OCH2O—Ph |
| 296 | 2,4-diF—Ph | 3,4-OCH2CH2O—Ph |
| 297 | 2,4-diF—Ph | 2-thienyl |
| 298 | 2,4-diF—Ph | 2-furanyl |
| 299 | 2,4-diF—Ph | 2-pyridyl |
| 300 | 2,4-diF—Ph | 4-pyridyl |
| 301 | 2,4-diF—Ph | 2-imidazolyl |
| 302 | 2,4-diF—Ph | 3-pyrazolyl |
| 303 | 2,4-diF—Ph | 2-thiazolyl |
| 304 | 2,4-diF—Ph | 5-tetrazolyl |
| 305 | 2,4-diF—Ph | 1-adamantyl |
| 306 | 4-Cl—Ph | Ph |
| 307 | 4-Cl—Ph | 3-CN—Ph |
| 308 | 4-Cl—Ph | 3-COCH3—Ph |
| 309 | 4-Cl—Ph | 3-CO2Me—Ph |
| 310 | 4-Cl—Ph | 3-CO2Et—Ph |
| 311 | 4-Cl—Ph | 3-CO2H—Ph |
| 312 | 4-Cl—Ph | 3-CONH2—Ph |
| 313 | 4-Cl—Ph | 3-CONHMe—Ph |
| 314 | 4-Cl—Ph | 3-F—Ph |
| 315 | 4-Cl—Ph | 3-Cl—Ph |
| 316 | 4-Cl—Ph | 3-Br—Ph |
| 317 | 4-Cl—Ph | 3-NO2—Ph |
| 318 | 4-Cl—Ph | 3-NH2—Ph |
| 319 | 4-Cl—Ph | 3-NHMe—Ph |
| 320 | 4-Cl—Ph | 3-NMe2—Ph |
| 321 | 4-Cl—Ph | 3-NHCOCH3—Ph |
| 322 | 4-Cl—Ph | 3-SO2NH2—Ph |
| 323 | 4-Cl—Ph | 3-SO2NHMe—Ph |
| 324 | 4-Cl—Ph | 3-CF3—Ph |
| 325 | 4-Cl—Ph | 3-OCH3—Ph |
| 326 | 4-Cl—Ph | 3-OPh—Ph |
| 327 | 4-Cl—Ph | 3-OCF3—Ph |
| 328 | 4-Cl—Ph | 3-SCH3—Ph |
| 329 | 4-Cl—Ph | 3-SOCH3—Ph |
| 330 | 4-Cl—Ph | 3-SO2CH3—Ph |
| 331 | 4-Cl—Ph | 3-OH—Ph |
| 332 | 4-Cl—Ph | 3-CH2OH—Ph |
| 333 | 4-Cl—Ph | 3-CHOHCH3—Ph |
| 334 | 4-Cl—Ph | 3-COH(CH3)2—Ph |
| 335 | 4-Cl—Ph | 3-CHOHPh—Ph |
| 336 | 4-Cl—Ph | 3-CH3—Ph |
| 337 | 4-Cl—Ph | 3-C2H5—Ph |
| 338 | 4-Cl—Ph | 3-iPr-Ph |
| 339 | 4-Cl—Ph | 3-tBu-Ph |
| 340 | 4-Cl—Ph | 3-Ph—Ph |
| 341 | 4-Cl—Ph | 3-CH2Ph—Ph |
| 342 | 4-Cl—Ph | 3-CH2CO2Me—Ph |
| 343 | 4-Cl—Ph | 3-(1-piperidinyl)-Ph |
| 344 | 4-Cl—Ph | 3-(1-pyrrolidinyl)-Ph |
| 345 | 4-Cl—Ph | 3-(2-imidazolyl)-Ph |
| 346 | 4-Cl—Ph | 3-(1-imidazolyl)-Ph |
| 347 | 4-Cl—Ph | 3-(2-thiazolyl)-Ph |
| 348 | 4-Cl—Ph | 3-(3-pyrazolyl)-Ph |
| 349 | 4-Cl—Ph | 3-(1-pyrazolyl)-Ph |
| 350 | 4-Cl—Ph | 3-(1-tetrazolyl)-Ph |
| 351 | 4-Cl—Ph | 3-(5-tetrazolyl)-Ph |
| 352 | 4-Cl—Ph | 3-(2-pyridyl)-Ph |
| 353 | 4-Cl—Ph | 3-(2-thienyl)-Ph |
| 354 | 4-Cl—Ph | 3-(2-furanyl)-Ph |
| 355 | 4-Cl—Ph | 4-CN—Ph |
| 356 | 4-Cl—Ph | 4-COCH3—Ph |
| 357 | 4-Cl—Ph | 4-CO2Me—Ph |
| 358 | 4-Cl—Ph | 4-CO2Et—Ph |
| 359 | 4-Cl—Ph | 4-CO2H—Ph |
| 360 | 4-Cl—Ph | 4-CONH2—Ph |
| 361 | 4-Cl—Ph | 4-CONHMe—Ph |
| 362 | 4-Cl—Ph | 4-CONHPh—Ph |
| 363 | 4-Cl—Ph | 4-NHCONH2—Ph |
| 364 | 4-Cl—Ph | 4-F—Ph |
| 365 | 4-Cl—Ph | 4-Cl—Ph |
| 366 | 4-Cl—Ph | 4-Br—Ph |
| 367 | 4-Cl—Ph | 4-NO2—Ph |
| 368 | 4-Cl—Ph | 4-NH2—Ph |
| 369 | 4-Cl—Ph | 4-NHMe—Ph |
| 370 | 4-Cl—Ph | 4-NMe2—Ph |
| 371 | 4-Cl—Ph | 4-NHCOCH3—Ph |
| 372 | 4-Cl—Ph | 4-SO2NH2—Ph |
| 373 | 4-Cl—Ph | 4-SO2NHMe—Ph |
| 374 | 4-Cl—Ph | 4-CF3—Ph |
| 375 | 4-Cl—Ph | 4-OCH3—Ph |
| 376 | 4-Cl—Ph | 4-OPh—Ph |
| 377 | 4-Cl—Ph | 4-OCF3—Ph |
| 378 | 4-Cl—Ph | 4-SCH3—Ph |
| 379 | 4-Cl—Ph | 4-SOCH3—Ph |
| 380 | 4-Cl—Ph | 4-SO2CH3—Ph |
| 381 | 4-Cl—Ph | 4-OH—Ph |
| 382 | 4-Cl—Ph | 4-CH2OH—Ph |
| 383 | 4-Cl—Ph | 4-CHOHCH3—Ph |
| 384 | 4-Cl—Ph | 4-COH(CH3)2—Ph |
| 385 | 4-Cl—Ph | 4-CH3—Ph |
| 386 | 4-Cl—Ph | 4-C2H5—Ph |
| 387 | 4-Cl—Ph | 4-iPr-Ph |
| 388 | 4-Cl—Ph | 4-tBu-Ph |
| 389 | 4-Cl—Ph | 4-Ph—Ph |
| 390 | 4-Cl—Ph | 4-CH2Ph—Ph |
| 391 | 4-Cl—Ph | 4-CH2CO2Me—Ph |
| 392 | 4-Cl—Ph | 4-(1-piperidinyl)-Ph |
| 393 | 4-Cl—Ph | 4-(1-pyrrolidinyl)-Ph |
| 394 | 4-Cl—Ph | 4-(2-imidazolyl)-Ph |
| 395 | 4-Cl—Ph | 4-(1-imidazolyl)-Ph |
| 396 | 4-Cl—Ph | 4-(2-thiazolyl)-Ph |
| 397 | 4-Cl—Ph | 4-(3-pyrazolyl)-Ph |
| 398 | 4-Cl—Ph | 4-(1-pyrazolyl)-Ph |
| 399 | 4-Cl—Ph | 4-(1-tetrazolyl)-Ph |
| 400 | 4-Cl—Ph | 4-(5-tetrazolyl)-Ph |
| 401 | 4-Cl—Ph | 4-(2-pyridyl)-Ph |
| 402 | 4-Cl—Ph | 4-(2-thienyl)-Ph |
| 403 | 4-Cl—Ph | 4-(2-furanyl)-Ph |
| 404 | 4-Cl—Ph | 2-CN—Ph |
| 405 | 4-Cl—Ph | 2-COCH3—Ph |
| 406 | 4-Cl—Ph | 2-CO2Me—Ph |
| 407 | 4-Cl—Ph | 2-CO2Et—Ph |
| 408 | 4-Cl—Ph | 2-CO2H—Ph |
| 409 | 4-Cl—Ph | 2-CONH2—Ph |
| 410 | 4-Cl—Ph | 2-CONHMe—Ph |
| 411 | 4-Cl—Ph | 2-F—Ph |
| 412 | 4-Cl—Ph | 2-Cl—Ph |
| 413 | 4-Cl—Ph | 2-Br—Ph |
| 414 | 4-Cl—Ph | 2-NO2—Ph |
| 415 | 4-Cl—Ph | 2-NH2—Ph |
| 416 | 4-Cl—Ph | 2-NHMe—Ph |
| 417 | 4-Cl—Ph | 2-NMe2—Ph |
| 418 | 4-Cl—Ph | 2-NHCOCH3—Ph |
| 419 | 4-Cl—Ph | 2-SO2NH2—Ph |
| 420 | 4-Cl—Ph | 2-SO2NHMe—Ph |
| 421 | 4-Cl—Ph | 2-CF3—Ph |
| 422 | 4-Cl—Ph | 2-OCH3—Ph |
| 423 | 4-Cl—Ph | 2-OPh—Ph |
| 424 | 4-Cl—Ph | 2-OCF3—Ph |
| 425 | 4-Cl—Ph | 2-SCH3—Ph |
| 426 | 4-Cl—Ph | 2-SOCH3—Ph |
| 427 | 4-Cl—Ph | 2-SO2CH3—Ph |
| 428 | 4-Cl—Ph | 2-OH—Ph |
| 429 | 4-Cl—Ph | 2-CH2OH—Ph |
| 430 | 4-Cl—Ph | 2-CHOHCH3—Ph |
| 431 | 4-Cl—Ph | 2-COH(CH3)2—Ph |
| 432 | 4-Cl—Ph | 2-CHOHPh—Ph |
| 433 | 4-Cl—Ph | 2-CH3—Ph |
| 434 | 4-Cl—Ph | 2-C2H5-Ph |
| 435 | 4-Cl—Ph | 2-iPr-Ph |
| 436 | 4-Cl—Ph | 2-tBu-Ph |
| 437 | 4-Cl—Ph | 2-Ph—Ph |
| 438 | 4-Cl—Ph | 2-CH2Ph—Ph |
| 439 | 4-Cl—Ph | 2-CH2CO2Me—Ph |
| 440 | 4-Cl—Ph | 2-(1-piperidinyl)-Ph |

TABLE 1*-continued

| | | |
|---|---|---|
| 441 | 4-Cl—Ph | 2-(1-pyrrolidinyl)-Ph |
| 442 | 4-Cl—Ph | 2-(2-imidazolyl)-Ph |
| 443 | 4-Cl—Ph | 2-(1-imidazolyl)-Ph |
| 444 | 4-Cl—Ph | 2-(2-thiazolyl)-Ph |
| 445 | 4-Cl—Ph | 2-(3-pyrazolyl)-Ph |
| 446 | 4-Cl—Ph | 2-(1-pyrazolyl)-Ph |
| 447 | 4-Cl—Ph | 2-(1-tetrazolyl)-Ph |
| 448 | 4-Cl—Ph | 2-(5-tetrazolyl)-Ph |
| 449 | 4-Cl—Ph | 2-(2-pyridyl)-Ph |
| 450 | 4-Cl—Ph | 2-(2-thienyl)-Ph |
| 451 | 4-Cl—Ph | 2-(2-furanyl)-Ph |
| 452 | 4-Cl—Ph | 2,4-diF—Ph |
| 453 | 4-Cl—Ph | 2,5-diF—Ph |
| 454 | 4-Cl—Ph | 2,6-diF—Ph |
| 455 | 4-Cl—Ph | 3,4-diF—Ph |
| 456 | 4-Cl—Ph | 3,5-diF—Ph |
| 457 | 4-Cl—Ph | 2,4-diCl—Ph |
| 458 | 4-Cl—Ph | 2,5-diCl—Ph |
| 459 | 4-Cl—Ph | 2,6-diCl—Ph |
| 460 | 4-Cl—Ph | 3,4-diCl—Ph |
| 461 | 4-Cl—Ph | 3,5-diCl—Ph |
| 462 | 4-Cl—Ph | 3,4-diCF3—Ph |
| 463 | 4-Cl—Ph | 3,5-diCF3—Ph |
| 464 | 4-Cl—Ph | 5-Cl-2-MeO—Ph |
| 465 | 4-Cl—Ph | 5-Cl-2-Me—Ph |
| 466 | 4-Cl—Ph | 2-F-5-Me—Ph |
| 467 | 4-Cl—Ph | 2-F-5-NO2—Ph |
| 468 | 4-Cl—Ph | 3,4-OCH2O—Ph |
| 469 | 4-Cl—Ph | 3,4-OCH2CH2O—Ph |
| 470 | 4-Cl—Ph | 2-MeO-4-Me—Ph |
| 471 | 4-Cl—Ph | 2-MeO-5-Me—Ph |
| 472 | 4-Cl—Ph | 1-naphthyl |
| 473 | 4-Cl—Ph | 2-naphthyl |
| 474 | 4-Cl—Ph | 2-thienyl |
| 475 | 4-Cl—Ph | 3-thienyl |
| 476 | 4-Cl—Ph | 2-furanyl |
| 477 | 4-Cl—Ph | 3-furanyl |
| 478 | 4-Cl—Ph | 2-pyridyl |
| 479 | 4-Cl—Ph | 3-pyridyl |
| 480 | 4-Cl—Ph | 4-pyridyl |
| 481 | 4-Cl—Ph | 2-indolyl |
| 482 | 4-Cl—Ph | 3-indolyl |
| 483 | 4-Cl—Ph | 5-indolyl |
| 484 | 4-Cl—Ph | 6-indolyl |
| 485 | 4-Cl—Ph | 3-indazolyl |
| 486 | 4-Cl—Ph | 5-indazolyl |
| 487 | 4-Cl—Ph | 6-indazolyl |
| 488 | 4-Cl—Ph | 2-imidazolyl |
| 489 | 4-Cl—Ph | 3-pyrazolyl |
| 490 | 4-Cl—Ph | 2-thiazolyl |
| 491 | 4-Cl—Ph | 5-tetrazolyl |
| 492 | 4-Cl—Ph | 2-benzimidazolyl |
| 493 | 4-Cl—Ph | 5-benzimidazolyl |
| 494 | 4-Cl—Ph | 2-benzothiazolyl |
| 495 | 4-Cl—Ph | 5-benzothiazolyl |
| 496 | 4-Cl—Ph | 2-benzoxazolyl |
| 497 | 4-Cl—Ph | 5-benzoxazolyl |
| 498 | 4-Cl—Ph | 1-adamantyl |
| 499 | 4-Cl—Ph | 2-adamantyl |
| 500 | 4-Cl—Ph | t-Bu |
| 501 | 2-Cl—Ph | 3-CN—Ph |
| 502 | 2-Cl—Ph | 3-COCH3—Ph |
| 503 | 2-Cl—Ph | 3-CO2Me—Ph |
| 504 | 2-Cl—Ph | 3-CO2Et—Ph |
| 505 | 2-Cl—Ph | 3-CO2H—Ph |
| 506 | 2-Cl—Ph | 3-CONH2—Ph |
| 507 | 2-Cl—Ph | 3-F—Ph |
| 508 | 2-Cl—Ph | 3-Cl—Ph |
| 509 | 2-Cl—Ph | 3-NH2—Ph |
| 510 | 2-Cl—Ph | 3-SO2NH2—Ph |
| 511 | 2-Cl—Ph | 3-CF3—Ph |
| 512 | 2-Cl—Ph | 3-OCH3—Ph |
| 513 | 2-Cl—Ph | 3-OEt—Ph |
| 514 | 2-Cl—Ph | 3-OCF3—Ph |
| 515 | 2-Cl—Ph | 3-SO2CH3—Ph |
| 516 | 2-Cl—Ph | 3-OH—Ph |
| 517 | 2-Cl—Ph | 3-CH3—Ph |
| 518 | 2-Cl—Ph | 3-C2H5—Ph |
| 519 | 2-Cl—Ph | 4-CN—Ph |
| 520 | 2-Cl—Ph | 4-COCH3—Ph |
| 521 | 2-Cl—Ph | 4-CO2Me—Ph |
| 522 | 2-Cl—Ph | 4-CO2Et—Ph |
| 523 | 2-Cl—Ph | 4-CO2H—Ph |
| 524 | 2-Cl—Ph | 4-CONH2—Ph |
| 525 | 2-Cl—Ph | 4-F—Ph |
| 526 | 2-Cl—Ph | 4-Cl—Ph |
| 527 | 2-Cl—Ph | 4-NH2—Ph |
| 528 | 2-Cl—Ph | 4-SO2NH2—Ph |
| 529 | 2-Cl—Ph | 4-CF3—Ph |
| 530 | 2-Cl—Ph | 4-OCH3—Ph |
| 531 | 2-Cl—Ph | 4-OEt—Ph |
| 532 | 2-Cl—Ph | 4-OCF3—Ph |
| 533 | 2-Cl—Ph | 4-SO2CH3—Ph |
| 534 | 2-Cl—Ph | 4-OH—Ph |
| 535 | 2-Cl—Ph | 4-CH3—Ph |
| 536 | 2-Cl—Ph | 4-C2H5—Ph |
| 537 | 2-Cl—Ph | 2,4-diF—Ph |
| 538 | 2-Cl—Ph | 2,5-diF—Ph |
| 539 | 2-Cl—Ph | 3,4-diF—Ph |
| 540 | 2-Cl—Ph | 3,5-diF—Ph |
| 541 | 2-Cl—Ph | 2,4-diCl—Ph |
| 542 | 2-Cl—Ph | 2,5-diCl—Ph |
| 543 | 2-Cl—Ph | 3,4-diCl—Ph |
| 544 | 2-Cl—Ph | 3,5-diCl—Ph |
| 545 | 2-Cl—Ph | 3,4-OCH2O—Ph |
| 546 | 2-Cl—Ph | 3,4-OCH2CH2O—Ph |
| 547 | 2-Cl—Ph | 2-thienyl |
| 548 | 2-Cl—Ph | 2-furanyl |
| 549 | 2-Cl—Ph | 2-pyridyl |
| 550 | 2-Cl—Ph | 4-pyridyl |
| 551 | 2-Cl—Ph | 2-imidazolyl |
| 552 | 2-Cl—Ph | 3-pyrazolyl |
| 553 | 2-Cl—Ph | 2-thiazolyl |
| 554 | 2-Cl—Ph | 5-tetrazolyl |
| 555 | 2-Cl—Ph | 1-adamantyl |
| 556 | 2,4-diCl—Ph | 3-CN—Ph |
| 557 | 2,4-diCl—Ph | 3-COCH3—Ph |
| 558 | 2,4-diCl—Ph | 3-CO2Me—Ph |
| 559 | 2,4-diCl—Ph | 3-CO2Et—Ph |
| 560 | 2,4-diCl—Ph | 3-CO2H—Ph |
| 561 | 2,4-diCl—Ph | 3-CONH2—Ph |
| 562 | 2,4-diCl—Ph | 3-F—Ph |
| 563 | 2,4-diCl—Ph | 3-Cl—Ph |
| 564 | 2,4-diCl—Ph | 3-NH2—Ph |
| 565 | 2,4-diCl—Ph | 3-SO2NH2—Ph |
| 566 | 2,4-diCl—Ph | 3-CF3—Ph |
| 567 | 2,4-diCl—Ph | 3-OCH3—Ph |
| 568 | 2,4-diCl—Ph | 3-OEt—Ph |
| 569 | 2,4-diCl—Ph | 3-OCF3—Ph |
| 570 | 2,4-diCl—Ph | 3-SO2CH3—Ph |
| 571 | 2,4-diCl—Ph | 3-OH—Ph |
| 572 | 2,4-diCl—Ph | 3-CH3—Ph |
| 573 | 2,4-diCl—Ph | 3-C2H5—Ph |
| 574 | 2,4-diCl—Ph | 4-CN—Ph |
| 575 | 2,4-diCl—Ph | 4-COCH3—Ph |
| 576 | 2,4-diCl—Ph | 4-CO2Me—Ph |
| 577 | 2,4-diCl—Ph | 4-CO2Et—Ph |
| 578 | 2,4-diCl—Ph | 4-CO2H—Ph |
| 579 | 2,4-diCl—Ph | 4-CONH2—Ph |
| 580 | 2,4-diCl—Ph | 4-F—Ph |
| 581 | 2,4-diCl—Ph | 4-Cl—Ph |
| 582 | 2,4-diCl—Ph | 4-NH2—Ph |
| 583 | 2,4-diCl—Ph | 4-SO2NH2—Ph |
| 584 | 2,4-diCl—Ph | 4-CF3—Ph |
| 585 | 2,4-diCl—Ph | 4-OCH3—Ph |
| 586 | 2,4-diCl—Ph | 4-OEt—Ph |
| 587 | 2,4-diCl—Ph | 4-OCF3—Ph |
| 588 | 2,4-diCl—Ph | 4-SO2CH3—Ph |
| 589 | 2,4-diCl—Ph | 4-OH—Ph |
| 590 | 2,4-diCl—Ph | 4-CH3—Ph |
| 591 | 2,4-diCl—Ph | 4-C2H5—Ph |
| 592 | 2,4-diCl—Ph | 2,4-diF—Ph |
| 593 | 2,4-diCl—Ph | 2,5-diF—Ph |
| 594 | 2,4-diCl—Ph | 3,4-diF—Ph |
| 595 | 2,4-diCl—Ph | 3,5-diF—Ph |
| 596 | 2,4-diCl—Ph | 2,4-diCl—Ph |
| 597 | 2,4-diCl—Ph | 2,5-diCl—Ph |
| 598 | 2,4-diCl—Ph | 3,4-diCl—Ph |

TABLE 1*-continued

| | | |
|---|---|---|
| 599 | 2,4-diCl—Ph | 3,5-diCl—Ph |
| 600 | 2,4-diCl—Ph | 3,4-OCH2O—Ph |
| 601 | 2,4-diCl—Ph | 3,4-OCH2CH2O—Ph |
| 602 | 2,4-diCl—Ph | 2-thienyl |
| 603 | 2,4-diCl—Ph | 2-furanyl |
| 604 | 2,4-diCl—Ph | 2-pyridyl |
| 605 | 2,4-diCl—Ph | 4-pyridyl |
| 606 | 2,4-diCl—Ph | 2-imidazolyl |
| 607 | 2,4-diCl—Ph | 3-pyrazolyl |
| 608 | 2,4-diCl—Ph | 2-thiazolyl |
| 609 | 2,4-diCl—Ph | 5-tetrazolyl |
| 610 | 2,4-diCl—Ph | 1-adamantyl |
| 611 | 3-OCH3—Ph | 3-CN—Ph |
| 612 | 3-OCH3—Ph | 3-COCH3—Ph |
| 613 | 3-OCH3—Ph | 3-CO2Me—Ph |
| 614 | 3-OCH3—Ph | 3-CO2Et—Ph |
| 615 | 3-OCH3—Ph | 3-CO2H—Ph |
| 616 | 3-OCH3—Ph | 3-CONH2—Ph |
| 617 | 3-OCH3—Ph | 3-F—Ph |
| 618 | 3-OCH3—Ph | 3-Cl—Ph |
| 619 | 3-OCH3—Ph | 3-NH2—Ph |
| 620 | 3-OCH3—Ph | 3-SO2NH2—Ph |
| 621 | 3-OCH3—Ph | 3-CF3—Ph |
| 622 | 3-OCH3—Ph | 3-OCH3—Ph |
| 623 | 3-OCH3—Ph | 3-OEt—Ph |
| 624 | 3-OCH3—Ph | 3-OCF3—Ph |
| 625 | 3-OCH3—Ph | 3-SO2CH3—Ph |
| 626 | 3-OCH3—Ph | 3-OH—Ph |
| 627 | 3-OCH3—Ph | 3-CH3—Ph |
| 628 | 3-OCH3—Ph | 3-C2H5—Ph |
| 629 | 3-OCH3—Ph | 4-CN—Ph |
| 630 | 3-OCH3—Ph | 4-COCH3—Ph |
| 631 | 3-OCH3—Ph | 4-CO2Me—Ph |
| 632 | 3-OCH3—Ph | 4-CO2Et—Ph |
| 633 | 3-OCH3—Ph | 4-CO2H—Ph |
| 634 | 3-OCH3—Ph | 4-CONH2—Ph |
| 635 | 3-OCH3—Ph | 4-F—Ph |
| 636 | 3-OCH3—Ph | 4-Cl—Ph |
| 637 | 3-OCH3—Ph | 4-NH2—Ph |
| 638 | 3-OCH3—Ph | 4-SO2NH2—Ph |
| 639 | 3-OCH3—Ph | 4-CF3—Ph |
| 640 | 3-OCH3—Ph | 4-OCH3—Ph |
| 641 | 3-OCH3—Ph | 4-OEt—Ph |
| 642 | 3-OCH3—Ph | 4-OCF3—Ph |
| 643 | 3-OCH3—Ph | 4-SO2CH3—Ph |
| 644 | 3-OCH3—Ph | 4-OH—Ph |
| 645 | 3-OCH3—Ph | 4-CH3—Ph |
| 646 | 3-OCH3—Ph | 4-C2H5—Ph |
| 647 | 3-OCH3—Ph | 2,4-diF—Ph |
| 648 | 3-OCH3—Ph | 2,5-diF—Ph |
| 649 | 3-OCH3—Ph | 3,4-diF—Ph |
| 650 | 3-OCH3—Ph | 3,5-diF—Ph |
| 651 | 3-OCH3—Ph | 2,4-diCl—Ph |
| 652 | 3-OCH3—Ph | 2,5-diCl—Ph |
| 653 | 3-OCH3—Ph | 3,4-diCl—Ph |
| 654 | 3-OCH3—Ph | 3,5-diCl—Ph |
| 655 | 3-OCH3—Ph | 3,4-OCH2O—Ph |
| 656 | 3-OCH3—Ph | 3,4-OCH2CH2O—Ph |
| 657 | 3-OCH3—Ph | 2-thienyl |
| 658 | 3-OCH3—Ph | 2-furanyl |
| 659 | 3-OCH3—Ph | 2-pyridyl |
| 660 | 3-OCH3—Ph | 4-pyridyl |
| 661 | 3-OCH3—Ph | 2-imidazolyl |
| 662 | 3-OCH3—Ph | 3-pyrazolyl |
| 663 | 3-OCH3—Ph | 2-thiazolyl |
| 664 | 3-OCH3—Ph | 5-tetrazolyl |
| 665 | 3-OCH3—Ph | 1-adamantyl |
| 666 | 2-thienyl | 3-CN—Ph |
| 667 | 2-thienyl | 3-COCH3—Ph |
| 668 | 2-thienyl | 3-F—Ph |
| 669 | 2-thienyl | 3-Cl—Ph |
| 670 | 2-thienyl | 3-NH2—Ph |
| 671 | 2-thienyl | 3-OCH3—Ph |
| 672 | 2-thienyl | 3-OH—Ph |
| 673 | 2-thienyl | 4-CN—Ph |
| 674 | 2-thienyl | 4-COCH3—Ph |
| 675 | 2-thienyl | 4-F—Ph |
| 676 | 2-thienyl | 4-Cl—Ph |
| 677 | 2-thienyl | 4-NH2—Ph |
| 678 | 2-thienyl | 4-OCH3—Ph |
| 679 | 2-thienyl | 4-OH—Ph |
| 680 | 2-thienyl | 3,4-diF—Ph |
| 681 | 2-thienyl | 3,5-diF—Ph |
| 682 | 2-thienyl | 3,4-diCl—Ph |
| 683 | 2-thienyl | 3,5-diCl—Ph |
| 684 | 2-thienyl | 3,4-OCH2O—Ph |
| 685 | 2-thienyl | 3,4-OCH2CH2O—Ph |
| 686 | 3-thienyl | 3-CN—Ph |
| 687 | 3-thienyl | 3-COCH3—Ph |
| 688 | 3-thienyl | 3-F—Ph |
| 689 | 3-thienyl | 3-Cl—Ph |
| 690 | 3-thienyl | 3-NH2—Ph |
| 691 | 3-thienyl | 3-OCH3—Ph |
| 692 | 3-thienyl | 3-OH—Ph |
| 693 | 3-thienyl | 4-CN—Ph |
| 694 | 3-thienyl | 4-COCH3—Ph |
| 695 | 3-thienyl | 4-F—Ph |
| 696 | 3-thienyl | 4-Cl—Ph |
| 697 | 3-thienyl | 4-NH2—Ph |
| 698 | 3-thienyl | 4-OCH3—Ph |
| 699 | 3-thienyl | 4-OH—Ph |
| 700 | 3-thienyl | 3,4-diF—Ph |
| 701 | 3-thienyl | 3,5-diF—Ph |
| 702 | 3-thienyl | 3,4-diCl—Ph |
| 703 | 3-thienyl | 3,5-diCl—Ph |
| 704 | 3-thienyl | 3,4-OCH2O—Ph |
| 705 | 3-thienyl | 3,4-OCH2CH2O—Ph |
| 706 | 2-furanyl | 3-CN—Ph |
| 707 | 2-furanyl | 3-COCH3—Ph |
| 708 | 2-furanyl | 3-F—Ph |
| 709 | 2-furanyl | 3-Cl—Ph |
| 710 | 2-furanyl | 3-NH2—Ph |
| 711 | 2-furanyl | 3-OCH3—Ph |
| 712 | 2-furanyl | 3-OH—Ph |
| 713 | 2-furanyl | 4-CN—Ph |
| 714 | 2-furanyl | 4-COCH3—Ph |
| 715 | 2-furanyl | 4-F—Ph |
| 716 | 2-furanyl | 4-Cl—Ph |
| 717 | 2-furanyl | 4-NH2—Ph |
| 718 | 2-furanyl | 4-OCH3—Ph |
| 719 | 2-furanyl | 4-OH—Ph |
| 720 | 2-furanyl | 3,4-diF—Ph |
| 721 | 2-furanyl | 3,5-diF—Ph |
| 722 | 2-furanyl | 3,4-diCl—Ph |
| 723 | 2-furanyl | 3,5-diCl—Ph |
| 724 | 2-furanyl | 3,4-OCH2O—Ph |
| 725 | 2-furanyl | 3,4-OCH2CH2O—Ph |
| 726 | 3-furanyl | 3-CN—Ph |
| 727 | 3-furanyl | 3-COCH3—Ph |
| 728 | 3-furanyl | 3-F—Ph |
| 729 | 3-furanyl | 3-Cl—Ph |
| 730 | 3-furanyl | 3-NH2—Ph |
| 731 | 3-furanyl | 3-OCH3—Ph |
| 732 | 3-furanyl | 3-OH—Ph |
| 733 | 3-furanyl | 4-CN—Ph |
| 734 | 3-furanyl | 4-COCH3—Ph |
| 735 | 3-furanyl | 4-F—Ph |
| 736 | 3-furanyl | 4-Cl—Ph |
| 737 | 3-furanyl | 4-NH2—Ph |
| 738 | 3-furanyl | 4-OCH3—Ph |
| 739 | 3-furanyl | 4-OH—Ph |
| 740 | 3-furanyl | 3,4-diF—Ph |
| 741 | 3-furanyl | 3,5-diF—Ph |
| 742 | 3-furanyl | 3,4-diCl—Ph |
| 743 | 3-furanyl | 3,5-diCl—Ph |
| 744 | 3-furanyl | 3,4-OCH2O—Ph |
| 745 | 3-furanyl | 3,4-OCH2CH2O—Ph |
| 746 | 2-pyridyl | 3-CN—Ph |
| 747 | 2-pyridyl | 3-COCH3—Ph |
| 748 | 2-pyridyl | 3-F—Ph |
| 749 | 2-pyridyl | 3-Cl—Ph |
| 750 | 2-pyridyl | 3-NH2—Ph |
| 751 | 2-pyridyl | 3-OCH3—Ph |
| 752 | 2-pyridyl | 3-OH—Ph |
| 753 | 2-pyridyl | 4-CN—Ph |
| 754 | 2-pyridyl | 4-COCH3—Ph |
| 755 | 2-pyridyl | 4-F—Ph |
| 756 | 2-pyridyl | 4-Cl—Ph |

TABLE 1*-continued

| | | |
|---|---|---|
| 757 | 2-pyridyl | 4-NH2—Ph |
| 758 | 2-pyridyl | 4-OCH3—Ph |
| 759 | 2-pyridyl | 4-OH—Ph |
| 760 | 2-pyridyl | 3,4-diF—Ph |
| 761 | 2-pyridyl | 3,5-diF—Ph |
| 762 | 2-pyridyl | 3,4-diCl—Ph |
| 763 | 2-pyridyl | 3,5-diCl—Ph |
| 764 | 2-pyridyl | 3,4-OCH2O—Ph |
| 765 | 2-pyridyl | 3,4-OCH2CH2O—Ph |
| 766 | 3-pyridyl | 3-CN—Ph |
| 767 | 3-pyridyl | 3-COCH3—Ph |
| 768 | 3-pyridyl | 3-F—Ph |
| 769 | 3-pyridyl | 3-Cl—Ph |
| 770 | 3-pyridyl | 3-NH2—Ph |
| 771 | 3-pyridyl | 3-OCH3—Ph |
| 772 | 3-pyridyl | 3-OH—Ph |
| 773 | 3-pyridyl | 4-CN—Ph |
| 774 | 3-pyridyl | 4-COCH3—Ph |
| 775 | 3-pyridyl | 4-F—Ph |
| 776 | 3-pyridyl | 4-Cl—Ph |
| 777 | 3-pyridyl | 4-NH2—Ph |
| 778 | 3-pyridyl | 4-OCH3—Ph |
| 779 | 3-pyridyl | 4-OH—Ph |
| 780 | 3-pyridyl | 3,4-diF—Ph |
| 781 | 3-pyridyl | 3,5-diF—Ph |
| 782 | 3-pyridyl | 3,4-diCl—Ph |
| 783 | 3-pyridyl | 3,5-diCl—Ph |
| 784 | 3-pyridyl | 3,4-OCH2O—Ph |
| 785 | 3-pyridyl | 3,4-OCH2CH2O—Ph |
| 786 | 4-pyridyl | 3-CN—Ph |
| 787 | 4-pyridyl | 3-COCH3—Ph |
| 788 | 4-pyridyl | 3-F—Ph |
| 789 | 4-pyridyl | 3-Cl—Ph |
| 790 | 4-pyridyl | 3-NH2—Ph |
| 791 | 4-pyridyl | 3-OCH3—Ph |
| 792 | 4-pyridyl | 3-OH—Ph |
| 793 | 4-pyridyl | 4-CN—Ph |
| 794 | 4-pyridyl | 4-COCH3—Ph |
| 795 | 4-pyridyl | 4-F—Ph |
| 796 | 4-pyridyl | 4-Cl—Ph |
| 797 | 4-pyridyl | 4-NH2—Ph |
| 798 | 4-pyridyl | 4-OCH3—Ph |
| 799 | 4-pyridyl | 4-OH—Ph |
| 800 | 4-pyridyl | 3,4-diF—Ph |
| 801 | 4-pyridyl | 3,5-diF—Ph |
| 802 | 4-pyridyl | 3,4-diCl—Ph |
| 803 | 4-pyridyl | 3,5-diCl—Ph |
| 804 | 4-pyridyl | 3,4-OCH2O—Ph |
| 805 | 4-pyridyl | 3,4-OCH2CH2O—Ph |
| 806 | 3-indolyl | 3-CN—Ph |
| 807 | 3-indolyl | 3-COCH3—Ph |
| 808 | 3-indolyl | 3-F—Ph |
| 809 | 3-indolyl | 3-Cl—Ph |
| 810 | 3-indolyl | 3-NH2—Ph |
| 811 | 3-indolyl | 3-OCH3—Ph |
| 812 | 3-indolyl | 3-OH—Ph |
| 813 | 3-indolyl | 4-CN—Ph |
| 814 | 3-indolyl | 4-COCH3—Ph |
| 815 | 3-indolyl | 4-F—Ph |
| 816 | 3-indolyl | 4-Cl—Ph |
| 817 | 3-indolyl | 4-NH2—Ph |
| 818 | 3-indolyl | 4-OCH3—Ph |
| 819 | 3-indolyl | 4-OH—Ph |
| 820 | 3-indolyl | 3,4-diF—Ph |
| 821 | 3-indolyl | 3,5-diF—Ph |
| 822 | 3-indolyl | 3,4-diCl—Ph |
| 823 | 3-indolyl | 3,5-diCl—Ph |
| 824 | 3-indolyl | 3,4-OCH2O—Ph |
| 825 | 3-indolyl | 3,4-OCH2CH2O—Ph |
| 826 | 5-indolyl | 3-CN—Ph |
| 827 | 5-indolyl | 3-COCH3—Ph |
| 828 | 5-indolyl | 3-F—Ph |
| 829 | 5-indolyl | 3-Cl—Ph |
| 830 | 5-indolyl | 3-NH2—Ph |
| 831 | 5-indolyl | 3-OCH3—Ph |
| 832 | 5-indolyl | 3-OH—Ph |
| 833 | 5-indolyl | 4-CN—Ph |
| 834 | 5-indolyl | 4-COCH3—Ph |
| 835 | 5-indolyl | 4-F—Ph |
| 836 | 5-indolyl | 4-Cl—Ph |
| 837 | 5-indolyl | 4-NH2—Ph |
| 838 | 5-indolyl | 4-OCH3—Ph |
| 839 | 5-indolyl | 4-OH—Ph |
| 840 | 5-indolyl | 3,4-diF—Ph |
| 841 | 5-indolyl | 3,5-diF—Ph |
| 842 | 5-indolyl | 3,4-diCl—Ph |
| 843 | 5-indolyl | 3,5-diCl—Ph |
| 844 | 5-indolyl | 3,4-OCH2O—Ph |
| 845 | 5-indolyl | 3,4-OCH2CH2O—Ph |
| 846 | 5-indazolyl | 3-CN—Ph |
| 847 | 5-indazolyl | 3-COCH3—Ph |
| 848 | 5-indazolyl | 3-F—Ph |
| 849 | 5-indazolyl | 3-Cl—Ph |
| 850 | 5-indazolyl | 3-NH2—Ph |
| 851 | 5-indazolyl | 3-OCH3—Ph |
| 852 | 5-indazolyl | 3-OH—Ph |
| 853 | 5-indazolyl | 4-CN—Ph |
| 854 | 5-indazolyl | 4-COCH3—Ph |
| 855 | 5-indazolyl | 4-F—Ph |
| 856 | 5-indazolyl | 4-Cl—Ph |
| 857 | 5-indazolyl | 4-NH2—Ph |
| 858 | 5-indazolyl | 4-OCH3—Ph |
| 859 | 5-indazolyl | 4-OH—Ph |
| 860 | 5-indazolyl | 3,4-diF—Ph |
| 861 | 5-indazolyl | 3,5-diF—Ph |
| 862 | 5-indazolyl | 3,4-diCl—Ph |
| 863 | 5-indazolyl | 3,5-diCl—Ph |
| 864 | 5-indazolyl | 3,4-OCH2O—Ph |
| 865 | 5-indazolyl | 3,4-OCH2CH2O—Ph |
| 866 | 5-benzimidazolyl | 3-CN—Ph |
| 867 | 5-benzimidazolyl | 3-COCH3—Ph |
| 868 | 5-benzimidazolyl | 3-F—Ph |
| 869 | 5-benzimidazolyl | 3-Cl—Ph |
| 870 | 5-benzimidazolyl | 3-NH2—Ph |
| 871 | 5-benzimidazolyl | 3-OCH3—Ph |
| 872 | 5-benzimidazolyl | 3-OH—Ph |
| 873 | 5-benzimidazolyl | 4-CN—Ph |
| 874 | 5-benzimidazolyl | 4-COCH3—Ph |
| 875 | 5-benzimidazolyl | 4-F—Ph |
| 876 | 5-benzimidazolyl | 4-Cl—Ph |
| 877 | 5-benzimidazolyl | 4-NH2—Ph |
| 878 | 5-benzimidazolyl | 4-OCH3—Ph |
| 879 | 5-benzimidazolyl | 4-OH—Ph |
| 880 | 5-benzimidazolyl | 3,4-diF—Ph |
| 881 | 5-benzimidazolyl | 3,5-diF—Ph |
| 882 | 5-benzimidazolyl | 3,4-diCl—Ph |
| 883 | 5-benzimidazolyl | 3,5-diCl—Ph |
| 884 | 5-benzimidazolyl | 3,4-OCH2O—Ph |
| 885 | 5-benzimidazolyl | 3,4-OCH2CH2O—Ph |
| 886 | 5-benzothiazolyl | 3-CN—Ph |
| 887 | 5-benzothiazolyl | 3-COCH3—Ph |
| 888 | 5-benzothiazolyl | 3-F—Ph |
| 889 | 5-benzothiazolyl | 3-Cl—Ph |
| 890 | 5-benzothiazolyl | 3-NH2—Ph |
| 891 | 5-benzothiazolyl | 3-OCH3—Ph |
| 892 | 5-benzothiazolyl | 3-OH—Ph |
| 893 | 5-benzothiazolyl | 4-CN—Ph |
| 894 | 5-benzothiazolyl | 4-COCH3—Ph |
| 895 | 5-benzothiazolyl | 4-F—Ph |
| 896 | 5-benzothiazolyl | 4-Cl—Ph |
| 897 | 5-benzothiazolyl | 4-NH2—Ph |
| 898 | 5-benzothiazolyl | 4-OCH3—Ph |
| 899 | 5-benzothiazolyl | 4-OH—Ph |
| 900 | 5-benzothiazolyl | 3,4-diF—Ph |
| 901 | 5-benzothiazolyl | 3,5-diF—Ph |
| 902 | 5-benzothiazolyl | 3,4-diCl—Ph |
| 903 | 5-benzothiazolyl | 3,5-diCl—Ph |
| 904 | 5-benzothiazolyl | 3,4-OCH2O—Ph |
| 905 | 5-benzothiazolyl | 3,4-OCH2CH2O—Ph |
| 906 | 5-benzoxazolyl | 3-CN—Ph |
| 907 | 5-benzoxazolyl | 3-COCH3—Ph |
| 908 | 5-benzoxazolyl | 3-F—Ph |
| 909 | 5-benzoxazolyl | 3-Cl—Ph |
| 910 | 5-benzoxazolyl | 3-NH2—Ph |
| 911 | 5-benzoxazolyl | 3-OCH3—Ph |
| 912 | 5-benzoxazolyl | 3-OH—Ph |
| 913 | 5-benzoxazolyl | 4-CN—Ph |
| 914 | 5-benzoxazolyl | 4-COCH3—Ph |

TABLE 1*-continued

| 915 | 5-benzoxazolyl | 4-F—Ph |
| 916 | 5-benzoxazolyl | 4-Cl—Ph |
| 917 | 5-benzoxazolyl | 4-NH2—Ph |
| 918 | 5-benzoxazolyl | 4-OCH3—Ph |
| 919 | 5-benzoxazolyl | 4-OH—Ph |
| 920 | 5-benzoxazolyl | 3,4-diF—Ph |
| 921 | 5-benzoxazolyl | 3,5-diF—Ph |
| 922 | 5-benzoxazolyl | 3,4-diCl—Ph |
| 923 | 5-benzoxazolyl | 3,5-diCl—Ph |
| 924 | 5-benzoxazolyl | 3,4-OCH2O—Ph |
| 925 | 5-benzoxazolyl | 3,4-OCH2CH2O—Ph |

*All stereocenters are (+/−) unless otherwise indicated.

Utility

The utility of the compounds in accordance with the present invention as modulators of chemokine receptor activity may be demonstrated by methodology known in the art, such as the assays for CCR-2 and CCR-3 ligand binding, as disclosed by Ponath et al., J. Exp. Med., 183, 2437–2448 (1996) and Uguccioni et al., J. Clin. Invest., 100, 1137–1143 (1997). Cell lines for expressing the receptor of interest include those naturally expressing the chemokine receptor, such as EOL-3 or THP-1, those induced to express the chemokine receptor by the addition of chemical or protein agents, such as HL-60 or AML14.3D10 cells treated with, for example, butyric acid with interleukin-5 present, or a cell engineered to express a recombinant chemokine receptor, such as CHO or HEK-293. Finally, blood or tissue cells, for example human peripheral blood eosinophils, isolated using methods as described by Hansel et al., J. Immunol. Methods, 145, 105–110 (1991), can be utilized in such assays. In particular, the compound of the present invention have activity in binding to the CCR-3 receptor in the aforementioned assays. As used herein, "activity" is intended to mean a compound demonstrating an IC50 of 10 μM or lower in concentration when measured in the aforementioned assays. Such a result is indicative of the intrinsic activity of the compounds as modulators of chemokine receptor activity. A general binding protocol is described below.

CCR3-Receptor Binding Protocol

Millipore filter plates (#MABVN1250) are treated with 5 μg/ml protamine in phosphate buffered saline, pH 7.2, for ten minutes at room temperature. Plates are washed three times with phosphate buffered saline and incubated with phosphate buffered saline for thirty minutes at room temperature. For binding, 50 μl of binding buffer (0.5% bovine serum albumen, 20 mM HEPES buffer and 5 mM magnesium chloride in RPMI 1640 media) with or without a test concentration of a compound present at a known concentration is combined with 50 μl of 125-I labeled human eotaxin (to give a final concentration of 150 pM radioligand) and 50 μl of cell suspension in binding buffer containing $5 \times 10^5$ total cells. Cells used for such binding assays can include cell lines transfected with a gene expressing CCR3 such as that described by Daugherty et al. (1996), isolated human eosinophils such as described by Hansel et al. (1991) or the AML14.3D10 cell line after differentiation with butyric acid as described by Tiffany et al. (1998). The mixture of compound, cells and radioligand are incubated at room temperature for thirty minutes. Plates are placed onto a vacuum manifold, vacuum applied, and plates washed three times with binding buffer with 0.5M NaCl added. The plastic skirt is removed from the plate, the plate allowed to air dry, the wells punch out and CPM counted. The percent inhibition of binding is calculated using the total count obtained in the absence of any competing compound or chemokine ligand and the background binding determined by addition of 100 nM eotaxin in place of the test compound.

The utility of the compounds in accordance with the present invention as inhibitors of the migration of eosinophils or cell lines expressing the chemokine receptors may be demonstrated by methodology known in the art, such as the chemotaxis assay disclosed by Bacon et al., Brit. J. Pharmacol., 95, 966–974 (1988). In particular, the compound of the present invention have activity in inhibition of the migration of eosinophils in the aforementioned assays. As used herein, "activity" is intended to mean a compound demonstrating an IC50 of 10 μM or lower in concentration when measured in the aforementioned assays. Such a result is indicative of the intrinsic activity of the compounds as modulators of chemokine receptor activity. A human eosinophil chemotaxis assay protocol is described below.

Human Eosinophil Chemotaxis Assay

Neuroprobe MBA96 96-well chemotaxis chambers with Neuroprobe polyvinylpyrrolidone-free polycarbonate PFD5 5-micron filters in place are warmed in a 37° C. incubator prior to assay. Freshly isolated human eosinophils, isolated according to a method such as that described by Hansel et al. (1991), are suspended in RPMI 1640 with 0.1% bovine serum albumin at $1 \times 10^6$ cells/ml and warmed in a 37° C. incubator prior to assay. A 20 nM solution of human eotaxin in RPMI 1640 with 0.1% bovine serum albumin is warmed in a 37° C. incubator prior to assay. The eosinophil suspension and the 20 nM eotaxin solution are each mixed 1:1 with prewarmed RPMI 1640 with 0.1% bovine serum albumin with or without a dilution of a test compound that is at two fold the desired final concentration. These mixtures are warmed in a 37° C. incubator prior to assay. The filter is separated from the prewarmed Neuroprobe chemotaxis chamber and the eotaxin/compound mixture is placed into a Polyfiltronics MPC 96 well plate that has been placed in the bottom part of the Neuro Probe chemotaxis chamber. The approximate volume is 370 microliters and there should be a positive meniscus after dispensing. The filter is replaced above the 96 well plate, the rubber gasket is attached to the bottom of the upper chamber, and the chamber assembled. A 200 μl volume of the cell suspension/compound mixture is added to the appropriate wells of the upper chamber. The upper chamber is covered with a plate sealer, and the assembled unit placed in a 37° C. incubator for 45 minutes. After incubation, the plate sealer is removed and all remaining cell suspension is aspirated off. The chamber is disassembled and, while holding the filter by the sides at a 90-degree angle, unmigrated cells are washed away using a gentle stream of phosphate buffered saline dispensed from a squirt bottle and then the filter wiped with a rubber tipped squeegee. The filter is allowed to completely dry and immersed completely in Wright Giemsa stain for 30–45 seconds. The filter is rinsed with distilled water for 7 minutes, rinsed once with water briefly, and allowed to dry. Migrated cells are enumerated by microscopy.

Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited. For example, eosinophilic infiltration to inflammatory sites (e.g., in asthma or allergic rhinitis) can be inhibited according to the present method. In particular, the compound of the following examples has activity in blocking the migration of cells expressing the CCR-3 receptor using the appropriate chemokines in the aforementioned assays. As used herein, "activity" is intended to mean a compound demonstrating an IC50 of 10 µM or lower in concentration when measured in the aforementioned assays. Such a result is also indicative of the intrinsic activity of the compounds as modulators of chemokine receptor activity.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migraines (e.g., Toxocara), eosinophilic gastroenteritis (e.g., *Anisaki* sp., *Phocanema* sp.), cutaneous larva migraines (*Ancylostoma braziliense, Ancylostoma caninum*). The compounds of the present invention are accordingly useful in the prevention and treatment of a wide variety of inflammatory, infectious and immunoregulatory disorders and diseases.

In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

Preferably, the compounds of the present invention are used to treat or prevent disorders selected from asthma, allergic rhinitis, atopic dermatitis, inflammatory bowel diseases, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, HIV infection, cystic fibrosis, Churg-Strauss syndrome, lymphoma, Hodgkin's disease, and colonic carcinoma.

More preferably, the compounds are used to treat or prevent inflammatory disorders selected from asthma, allergic rhinitis, atopic dermatitis, and inflammatory bowel disease.

Even more preferably, the compounds are used to asthma.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102,203), leukotriene biosynthesis inhibitors (zileuton, BAY-1005); (f) non-steroidal antiinflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (I) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone ad pioglitazone); (l) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (o) other compound such as 5-aminosalicylic acid an prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective doses of each ingredient.

Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient,and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise that as specifically described herein.

What is claimed is:

1. A compound of formula I:

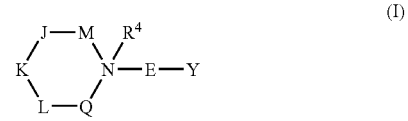

or stereoisomers or pharmaceutically acceptable salts thereof, wherein:

M is absent or selected from $CH_2$, $CHR^5$, $CHR^{13}$, $CR^{13}R^{13}$, and $CR^5R^{13}$;

Q is selected from $CH_2$, $CHR^5$, $CHR^{13}$, $CR^{13}R^{13}$, and $CR^5R^{13}$;

J, K, and L are independently selected from $CH_2$, $CHR^5$, $CHR^6$, $CR^6R^6$ and $CR^5R^6$;

with the provisos:

1) at least one of M, J, K, L, or Q contains an $R^5$; and 2) when M is absent, J is selected from $CH_2$, $CHR^5$, $CHR^{13}$, and $CR^5R^{13}$;

E is $—(CR^7R^8)—(CR^9R^{10})_v—$;

Y is selected from:

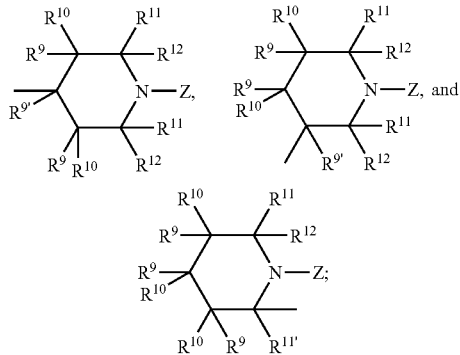

Z is selected from C(O)R$^3$, S(O)$_2$R$^3$, C(O)OR$^3$, C(O)NR$^2$R$^3$, C(=NR$^1$)NR$^2$R$^3$, C(=CHCN)NR$^2$R$^3$, C(=CHNO$_2$)NR$^2$R$^3$, C(=C(CN)$_2$)NR$^2$R$^3$, and (CR'R')$_t$-phenyl substituted with 0–5 R$^{15}$;

R', at each occurrence, is selected from H, C$_{1-6}$ alkyl, C$_{2-8}$ alkenyl, C$_{2-8}$ alkynyl, (CH$_2$)$_r$C$_{3-6}$ cycloalkyl, and (CH$_2$)$_r$phenyl substituted with R$^{15e}$;

R$^1$ is selected from H, C$_{1-6}$ alkyl, C$_{3-6}$ cycloalkyl, OH, CN, and (CH$_2$)$_w$phenyl;

R$^2$ is selected from H, C$_{1-8}$ alkyl, C$_{2-8}$ alkenyl, C$_{2-8}$ alkynyl, (CH$_2$)$_r$C$_{3-6}$ cycloalkyl, and a (CH$_2$)$_r$—C$_{3-10}$ carbocyclic residue substituted with 0–5 R$^{2a}$;

R$^{2a}$, at each occurrence, is selected from C$_{1-4}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{2b}$R$^{2b}$, (CH$_2$)$_r$OH, (CH$_2$)$_r$OR$^{2c}$, (CH$_2$)$_r$SH, (CH$_2$)$_r$SR$^{2c}$, (CH$_2$)$_r$C(O)R$^{2b}$, (CH$_2$)$_r$C(O)NR$^{2b}$R$^{2b}$, (CH$_2$)$_r$NR$^{2b}$C(O)R$^{2b}$, (CH$_2$)$_r$C(O)OR$^{2b}$, (CH$_2$)$_r$OC(O)R$^{2c}$, (CH$_2$)$_r$CH(=NR$^{2b}$)NR$^{2b}$R$^{2b}$, (CH$_2$)$_r$NHC(=NR$^{2b}$)NR$^{2b}$R$^{2b}$, (CH$_2$)$_r$S(O)$_p$R$^{2c}$, (CH$_2$)$_r$S(O)$_2$NR$^{2b}$R$^{2b}$, (CH$_2$)$_r$NR$^{2b}$S(O)$_2$R$^{2c}$, and (CH$_2$)$_r$phenyl;

R$^{2b}$, at each occurrence, is selected from H, C$_{1-6}$ alkyl, C$_{3-6}$ cycloalkyl, and phenyl;

R$^{2c}$, at each occurrence, is selected from C$_{1-5}$ alkyl, C$_{3-6}$ cycloalkyl, and phenyl;

R$^3$ is selected from a CR$^{3'}$R$^{3''}$R$^{3'''}$, (CR$^{3'}$R$^{3''}$)$_r$—C$_{3-10}$ carbocyclic residue substituted with 0–5 R$^{15}$ and a (CR$^{3'}$R$^{3''}$)$_r$-5–10 membered heterocyclic system containing 1–4 heteroatoms selected from N, O, and S, substituted with 0–3 R$^{15}$;

R$^{3'}$ and R$^{3''}$, at each occurrence, are selected from H, C$_{1-6}$ alkyl, (CH$_2$)$_r$C$_{3-6}$ cycloalkyl, and phenyl;

R$^4$ is absent;

R$^5$ is selected from a (CR$^{5'}$R$^{5''}$)$_t$—C$_{3-10}$ carbocyclic residue substituted with 0–5 R$^{16}$ and a (CR$^{5'}$R$^{5''}$)$_r$-5–10 membered heterocyclic system containing 1–4 heteroatoms selected from N, O, and S, substituted with 0–3 R$^{16}$;

R$^{5'}$ and R$^{5''}$, at each occurrence, are selected from H, C$_{1-6}$ alkyl, (CH$_2$)$_r$C$_{3-6}$ cycloalkyl, and phenyl;

R$^6$, at each occurrence, is selected from C$_{1-4}$ alkyl, C$_{2-8}$ alkenyl, C$_{2-8}$ alkynyl, (CH$_2$)$_r$C$_{3-6}$ cycloalkyl, (CF$_2$)$_r$CF$_3$, CN, (CH$_2$)$_r$NR$^{6a}$R$^{6a'}$, (CH$_2$)$_r$OH, (CH$_2$)$_r$OR$^{6b}$, (CH$_2$)$_r$SH, (CH$_2$)$_r$SR$^{6b}$, (CH$_2$)$_r$C(O)OH, (CH$_2$)$_r$C(O)R$^{6b}$, (CH$_2$)$_r$C(O)NR$^{6a}$R$^{6a'}$, (CH$_2$)$_r$NR$^{6d}$C(O)R$^{6a}$, (CH$_2$)$_r$C(O)OR$^{6b}$, (CH$_2$)$_r$OC(O)R$^{6b}$, (CH$_2$)$_r$S(O)$_p$R$^{6b}$, (CH$_2$)$_r$S(O)$_2$NR$^{6a}$R$^{6a'}$, (CH$_2$)$_r$NR$^{6d}$S(O)$_2$R$^{6b}$, and (CH$_2$)$_r$phenyl substituted with 0–3 R$^{6c}$;

R$^{6a}$ and R$^{6a'}$, at each occurrence, are selected from H, C$_{1-6}$ alkyl, C$_{3-6}$ cycloalkyl, and phenyl substituted with 0–3 R$^{6c}$;

R$^{6b}$, at each occurrence, is selected from C$_{1-6}$ alkyl, C$_{3-6}$ cycloalkyl, and phenyl substituted with 0–3 R$^{6c}$;

R$^{6c}$, at each occurrence, is selected from C$_{1-6}$ alkyl, C$_{3-6}$ cycloalkyl, Cl, F, Br, I, CN, NO$_2$, (CF$_2$)$_r$CF$_3$, (CH$_2$)$_r$OC$_{1-4}$ alkyl, (CH$_2$)$_r$OH, (CH$_2$)$_r$SC$_{1-5}$ alkyl, and (CH$_2$)$_r$NR$^{6d}$R$^{6d}$;

R$^{6d}$, at each occurrence, is selected from H, C$_{1-6}$ alkyl, and C$_{3-6}$ cycloalkyl;

R$^7$ is selected from H, C$_{1-8}$ alkyl, C$_{2-8}$ alkenyl, C$_{2-8}$ alkynyl, (CH$_2$)$_q$OH, (CH$_2$)$_q$SH, (CH$_2$)$_q$OR$^{7d}$, (CH$_2$)$_q$SR$^{7d}$, (CH$_2$)$_q$NR$^{7a}$R$^{7a'}$, (CH$_2$)$_q$C(O)OH, (CH$_2$)$_q$C(O)R$^{7b}$, (CH$_2$)$_q$C(O)NR$^{7a}$R$^{7a'}$, (CH$_2$)$_q$NR$^{7a}$C(O)R$^{7a}$, (CH$_2$)$_r$C(O)OR$^{7b}$, (CH$_2$)$_q$OC(O)R$^{7b}$, (CH$_2$)$_q$S(O)$_p$R$^{7b}$, (CH$_2$)$_q$S(O)$_2$NR$^{7a}$R$^{7a'}$, (CH$_2$)$_q$NR$^{7a}$S(O)$_2$R$^{7b}$, C$_{1-6}$ haloalkyl, a (CH$_2$)$_r$—C$_{3-10}$ carbocyclic residue substituted with 0–3 R$^{7c}$, and a (CH$_2$)$_r$-5–10 membered heterocyclic system containing 1–4 heteroatoms selected from N, O, and S, substituted with 0–2 R$^{7c}$;

R$^{7a}$ and R$^{7a'}$, at each occurrence, are selected from H, C$_{1-6}$ alkyl, C$_{2-8}$ alkenyl, C$_{2-8}$ alkynyl, (CH$_2$)$_r$C$_{3-6}$ cycloalkyl, a (CH$_2$)$_r$—C$_{3-10}$ carbocyclic residue substituted with 0–5 R$^{7e}$, and a (CH$_2$)$_r$-5–10 membered heterocyclic system containing 1–4 heteroatoms selected from N, O, and S, substituted with 0–3 R$^{7e}$;

R$^{7b}$, at each occurrence, is selected from C$_{1-6}$ alkyl, C$_{2-8}$ alkenyl, C$_{2-8}$ alkynyl, a (CH$_2$)$_r$—C$_{3-6}$ carbocyclic residue substituted with 0–2 R$^{7e}$, and a (CH$_2$)$_r$-5–6 membered heterocyclic system containing 1–4 heteroatoms selected from N, O, and S, substituted with 0–3 R$^{7e}$;

R$^{7c}$, at each occurrence, is selected from C$_{1-4}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{7f}$R$^{7f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{7b}$, (CH$_2$)$_r$C(O)NR$^{7f}$R$^{7f}$, (CH$_2$)$_r$NR$^{7f}$C(O)R$^{7a}$, (CH$_2$)$_r$C(O)OC$_{1-4}$ alkyl, (CH$_2$)$_r$OC(O)R$^{7b}$, (CH$_2$)$_r$C(=NR$^{7f}$)NR$^{7f}$R$^{7f}$, (CH$_2$)$_r$S(O)$_p$R$^{7b}$, (CH$_2$)$_r$NHC(=NR$^{7f}$)NR$^{7f}$R$^{7f}$, (CH$_2$)$_r$S(O)$_2$NR$^{7f}$R$^{7f}$, (CH$_2$)$_r$NR$^{7f}$S(O)$_2$R$^{7b}$, and (CH$_2$)$_r$phenyl substituted with 0–3 R$^{7e}$;

R$^{7d}$, at each occurrence, is selected from C$_{1-6}$ alkyl substituted with 0–3 R$^{7e}$, alkenyl, alkynyl, and a C$_{3-10}$ carbocyclic residue substituted with 0–3 R$^{7c}$;

R$^{7e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{7f}$R$^{7f}$, and (CH$_2$)$_r$phenyl;

R$^{7f}$, at each occurrence, is selected from H, C$_{1-5}$ alkyl, and C$_{3-6}$ cycloalkyl;

R$^8$ is selected from H, C$_{1-6}$ alkyl, C$_{3-6}$ cycloalkyl, and (CH$_2$)$_r$phenyl substituted with 0–3 R$^{8a}$;

R$^{8a}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{7f}$R$^{7f}$, and (CH$_2$)$_r$phenyl;

alternatively, R$^7$ and R$^8$ join to form C$_{3-7}$ cycloalkyl, or =NR$^{8b}$;

R$^{8b}$ is selected from H, C$_{1-6}$ alkyl, C$_{3-6}$ cycloalkyl, OH, CN, and (CH$_2$)$_r$-phenyl;

R$^9$, R$^{9'}$, R$^{10}$, R$^{11}$, R$^{11'}$, and R$^{12}$ are H;

R$^{13}$, at each occurrence, is selected from C$_{1-4}$ alkyl, C$_{2-8}$ alkenyl, C$_{2-8}$ alkynyl, C$_{3-6}$ cycloalkyl, (CF$_2$)$_w$CF$_3$, (CH$_2$)$_q$NR$^{13a}$R$^{13a'}$, (CH$_2$)$_q$OH, (CH$_2$)$_q$OR$^{13b}$, (CH$_2$)$_q$SH, (CH$_2$)$_q$SR$^{13b}$, (CH$_2$)$_w$C(O)OH, (CH$_2$)$_w$C(O)R$^{13b}$, (CH$_2$)$_w$C(O)NR$^{13a}$R$^{13a'}$, (CH$_2$)$_q$NR$^{13d}$C(O)R$^{13a}$, $(CH_2)_wC(O)OR^{13b}$, $(CH_2)_qOC(O)R^{13b}$, $(CH_2)_wS(O)_pR^{13b}$, $(CH_2)_wS(O)_2NR^{13a}R^{13a'}$, $(CH_2)_qNR^{13d}S(O)_2R^{13b}$, and $(CH_2)_w$-phenyl substituted with 0–3 $R^{13c}$;

$R^{13a}$ and $R^{13a'}$, at each occurrence, are selected from H, $C_{1-6}$ alkyl, $C_{3-6}$ cycloalkyl, and phenyl substituted with 0–3 $R^{13c}$;

$R^{13b}$, at each occurrence, is selected from $C_{1-6}$ alkyl, $C_{3-6}$ cycloalkyl, and phenyl substituted with 0–3 $R^{13c}$;

$R^{13c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{13d}R^{13d}$;

$R^{13d}$, at each occurrence, is selected from H, $C_{1-6}$ alkyl, and $C_{3-6}$ cycloalkyl;

$R^{15}$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{15a}R^{15a'}$, $(CHR')_rOH$, $(CHR')_rO(CHR')_rR^{15d}$, $(CHR')_rSH$, $(CHR')_rC(O)H$, $(CHR')_rS(CHR')_rR^{15d}$, $(CHR')_rC(O)OH$, $(CHR')_rC(O)(CHR')_rR^{15b}$, $(CHR')_rC(O)NR^{15a}R^{15a'}$, $(CHR')_rNR^{15f}C(O)(CHR')_rR^{15b}$, $(CHR')_rC(O)O(CHR')_rR^{15d}$, $(CHR')_rOC(O)(CHR')_rR^{15b}$, $(CHR')_rC(=NR^{15f})NR^{15a}R^{15a'}$, $(CHR')_rNHC(=NR^{15f})NR^{15f}R^{15f}$, $(CHR')_rS(O)_p(CHR')_rR^{15b}$, $(CHR')_rS(O)_2NR^{15a}R^{15a'}$, $(CHR')_rNR^{15f}S(O)_2(CHR')_rR^{15b}$, $C_{1-6}$ haloalkyl, $C_{2-8}$ alkenyl substituted with 0–3 R', $C_{2-8}$ alkynyl substituted with 0–3 R', $(CHR')_r$phenyl substituted with 0–3 $R^{15e}$, and a $(CH_2)_r$-5–10 membered heterocyclic system containing 1–4 heteroatoms selected from N, O, and S, substituted with 0–2 $R^{15e}$;

$R^{15a}$ and $R^{15a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{15e}$, and a $(CH_2)_r$-5–10 membered heterocyclic system containing 1–4 heteroatoms selected from N, O, and S, substituted with 0–2 $R^{15e}$;

$R^{15b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–3 $R^{15e}$, and $(CH_2)_r$-5–6 membered heterocyclic system containing 1–4 heteroatoms selected from N, O, and S, substituted with 0–2 $R^{15e}$;

$R^{15d}$, at each occurrence, is selected from $C_{2-8}$ alkenyl, $C_{2-8}$ alkynyl, $C_{1-6}$ alkyl substituted with 0–3 $R^{15e}$, a $(CH_2)_r$—$C_{3-10}$ carbocyclic residue substituted with 0–3 $R^{15e}$, and a $(CH_2)_r$-5–6 membered heterocyclic system containing 1–4 heteroatoms selected from N, O, and S, substituted with 0–3 $R^{15e}$;

$R^{15e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{15f}R^{15f}$, and $(CH_2)_r$phenyl;

$R^{15f}$, at each occurrence, is selected from H, $C_{1-5}$ alkyl, $C_{3-6}$ cycloalkyl, and phenyl;

$R^{16}$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{16a}R^{16a'}$, $(CHR')_rOH$, $(CHR')_rO(CHR')_rR^{16d}$, $(CHR')_rSH$, $(CHR')_rC(O)H$, $(CHR')_rS(CHR')_rR^{16d}$, $(CHR')_rC(O)OH$, $(CHR')_rC(O)(CHR')_rR^{16b}$, $(CHR')_rC(O)NR^{16a}R^{16a'}$, $(CHR')_rNR^{16f}C(O)(CHR')_rR^{16b}$, $(CHR')_rC(O)O(CHR')_rR^{16d}$, $(CHR')_rOC(O)(CHR')_rR^{16b}$, $(CHR')_rC(=NR^{16f})NR^{16a}R^{16a'}$, $(CHR')_rNHC(=NR^{16f})NR^{16f}R^{16f}$, $(CHR')_rS(O)_p(CHR')_rR^{16b}$, $(CHR')_rS(O)_2NR^{16a}R^{16a'}$, $(CHR')_rNR^{16f}S(O)_2(CHR')_rR^{16b}$, $C_{1-6}$ haloalkyl, $C_{2-8}$ alkenyl substituted with 0–3 R', $C_{2-8}$ alkynyl substituted with 0–3 R', and $(CHR')_r$phenyl substituted with 0–3 $R^{16e}$;

$R^{16a}$ and $R^{16a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{16e}$, and a $(CH_2)_r$-5–10 membered heterocyclic system containing 1–4 heteroatoms selected from N, O, and S, substituted with 0–2 $R^{16e}$;

$R^{16b}$, at each occurrence, is selected from $C_{1-6}$ alkyl, $C_{2-8}$ alkenyl, $C_{2-8}$ alkynyl, a $(CH_2)_rC_{3-6}$ carbocyclic residue substituted with 0–3 $R^{16e}$, and a $(CH_2)_r$-5–6 membered heterocyclic system containing 1–4 heteroatoms selected from N, O, and S, substituted with 0–2 $R^{16e}$;

$R^{16d}$, at each occurrence, is selected from $C_{2-8}$ alkenyl, $C_{2-8}$ alkynyl, $C_{1-6}$ alkyl substituted with 0–3 $R^{16e}$, a $(CH_2)_r$—$C_{3-10}$ carbocyclic residue substituted with 0–3 $R^{16e}$, and a $(CH_2)_r$-5–6 membered heterocyclic system containing 1–4 heteroatoms selected from N, O, and S, substituted with 0–3 $R^{16e}$;

$R^{16e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{16f}R^{16f}$, and $(CH_2)_r$phenyl;

$R^{16f}$, at each occurrence, is selected from H, $C_{1-5}$ alkyl, and $C_{3-6}$ cycloalkyl, and phenyl;

v is selected from 0, 1, and 2;

t is selected from 1 and 2;

w is selected from 0 and 1;

r is selected from 0, 1, 2, 3, 4, and 5;

q is selected from 1, 2, 3, 4, and 5; and p is selected from 1, 2, and 3.

2. The compound according to claim 1, wherein:

$R^2$ is selected from H and $C_{1-4}$ alkyl;

$R^6$, at each occurrence, is selected from $C_{1-4}$ alkyl, $C_{2-8}$ alkenyl, $C_{2-8}$ alkynyl, $(CH_2)_rC_{3-6}$ cycloalkyl, $(CF_2)_rCF_3$, CN, $(CH_2)_rOH$, $(CH_2)_rOR^{6b}$, $(CH_2)_rC(O)R^{6b}$, $(CH_2)_rC(O)NR^{6a}R^{6a'}$, $(CH_2)_rNR^{6d}C(O)R^{6a}$, and $(CH_2)_t$ phenyl substituted with 0–3 $R^{6c}$;

$R^{6a}$ and $R^{6a'}$, at each occurrence, are selected from H, $C_{1-6}$ alkyl, $C_{3-6}$ cycloalkyl, and phenyl substituted with 0–3 $R^{6c}$;

$R^{6b}$, at each occurrence, is selected from $C_{1-6}$ alkyl, $C_{3-6}$ cycloalkyl, and phenyl substituted with 0–3 $R^{6c}$;

$R^{6c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{6d}R^{6d}$;

$R^{6d}$, at each occurrence, is selected from H, $C_{1-6}$ alkyl, and $C_{3-6}$ cycloalkyl;

$R^7$, is selected from H, $C_{1-3}$ alkyl, $(CH_2)_rC_{3-6}$ cycloalkyl, $(CH_2)_qOH$, $(CH_2)_qOR^{7d}$, $(CH_2)_qNR^{7a}R^{7a'}$, $(CH_2)_rC(O)R^{7b}$, $(CH_2)_rC(O)NR^{7a}R^{7a'}$, $(CH_2)_qNR^{7a}C(O)R^{7a}$, $C_{1-6}$ haloalkyl, $(CH_2)_r$phenyl with 0–2 $R^{7c}$;

$R^{7a}$ and $R^{7a'}$, at each occurrence, are selected from H, $C_{1-6}$ alkyl, $(CH_2)_rC_{3-6}$ cycloalkyl, a $(CH_2)_r$phenyl substituted with 0–3 $R^{7e}$;

$R^{7b}$, at each occurrence, is selected from $C_{1-6}$ alkyl, $C_{2-8}$ alkenyl, $C_{2-8}$ alkynyl, $(CH_2)_rC_{3-6}$ cycloalkyl, $(CH_2)_r$phenyl substituted with 0–3 $R^{7e}$;

$R^{7c}$, at each occurrence, is selected from $C_{1-4}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{7f}R^{7f}$, $(CH_2)_rOH$, $(CH_2)_rOC_{1-4}$ alkyl, $(CH_2)_rC(O)R^{7b}$, $(CH_2)_rC(O)NR^{7f}R^{7f}$, $(CH_2)_rNR^{7f}C(O)R^{7a}$, $(CH_2)_rS(O)_pR^{7b}$, $(CH_2)_rS(O)_2NR^{7f}R^{7f}$, $(CH_2)_rNR^{7f}S(O)_2R^{7b}$, and $(CH_2)_r$phenyl substituted with 0–2 $R^{7e}$;

$R^{7d}$, at each occurrence, is selected from $C_{1-6}$ alkyl, $(CH_2)_vC_{3-6}$ cycloalkyl, $(CH_2)_r$phenyl substituted with 0–3 $R^{7e}$;

$R^{7e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{7f}R^{7f}$, and $(CH_2)_r$phenyl;

$R^{7f}$, at each occurrence, is selected from H, $C_{1-5}$ alkyl, and $C_{3-6}$ cycloalkyl;

$R^8$ is H or joins with $R^7$ to form $=NR^{8b}$;

$R^{13}$, at each occurrence, is selected from $C_{1-4}$ alkyl, $C_{3-6}$ cycloalkyl, $(CH_2)NR^{13a}R^{13a'}$, $(CH_2)OH$, $(CH_2)OR^{13b}$, $(CH_2)_wC(O)R^{13b}$, $(CH_2)_wC(O)NR^{13a}R^{13a'}$, $(CH_2)NR^{13d}C(O)R^{13a}$, $(CH_2)_wS(O)_2NR^{13a}R^{13a'}$, $(CH_2)NR^{13d}S(O)_2R^{13b}$, and $(CH_2)_w$-phenyl substituted with 0–3 $R^{13c}$;

$R^{13a}$ and $R^{13a'}$, at each occurrence, are selected from H, $C_{1-6}$ alkyl, $C_{3-6}$ cycloalkyl, and phenyl substituted with 0–3 $R^{13c}$;

$R^{13b}$, at each occurrence, is selected from $C_{1-6}$ alkyl, $C_{3-6}$ cycloalkyl, and phenyl substituted with 0–3 $R^{13c}$;

$R^{13c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, and $(CH_2)_rNR^{13d}R^{13d}$;

$R^{13d}$, at each occurrence, is selected from H, $C_{1-6}$ alkyl, and $C_{3-6}$ cycloalkyl;

v is selected from 1 and 2;

q is selected from 1, 2, and 3; and r is selected from 0, 1, 2, and 3.

3. The compound according to claim 2, wherein:

$R^3$ is selected from a $(CR^{3'}H)_r$-carbocyclic residue substituted with 0–5 $R^{15}$, wherein the carbocyclic residue is selected from phenyl, $C_{3-6}$ cycloalkyl, naphthyl, and adamantyl; and a $(CR^{3'}H)_r$-heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, isoindolyl, piperidinyl, pyrrazolyl, 1,2,4-triazolyl, 1,2,3-triazolyl, tetrazolyl, thiazolyl, oxazolyl, pyrazinyl, and pyrimidinyl; and $R^5$ is selected from $(CR^{5'}H)_r$-phenyl substituted with 0–5 $R^{16}$; and a $(CR^{5'}H)_r$-heterocyclic system substituted with 0–3 $R^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, isoindolyl, piperidinyl, pyrrazolyl, 1,2,4-triazolyl, 1,2,3-triazolyl, tetrazolyl, thiazolyl, oxazolyl, pyrazinyl, and pyrimidinyl.

4. The compound according to claim 3, wherein the $R^{16}$, at each occurrence, is selected from $C_{1-8}$ alkyl, $(CH_2)_vC_{3-6}$ cycloalkyl, $CF_3$, Cl, Br, I, F, $(CH_2)_r$ $NR^{16a}R^{16a'}$, $NO_2$, CN, OH, $(CH_2)_rOR^{16d}$, $(CH_2)_rC(O)$ $R^{16b}$, $(CH_2)_rC(O)NR^{16a}R^{16a'}$, $(CH_2)_rNR^{16f}C(O)R^{16b}$, $(CH_2)_rS(O)_pR^{16b}$, $(CH_2)_rS(O)_2NR^{16a}R^{16a'}$, $(CH_2)_r$ $NR^{16f}S(O)_2R^{16b}$, and $(CH_2)_r$phenyl substituted with 0–3 $R^{16e}$;

$R^{16a}$ and $R^{16a'}$, at each occurrence, are selected from H, $C_{1-6}$ alkyl, $C_{3-6}$ cycloalkyl, and $(CH_2)_r$phenyl substituted with 0–3 $R^{16e}$;

$R^{16b}$, at each occurrence, is selected from H, $C_{1-6}$ alkyl, $C_{3-6}$ cycloalkyl, and $(CH_2)_r$phenyl substituted with 0–3 $R^{16e}$;

$R^{16d}$, at each occurrence, is selected from $C_{1-6}$ alkyl and phenyl;

$R^{16e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{16f}$, at each occurrence, is selected from H, and $C_{1-5}$ alkyl.

5. The compound according to claim 4, wherein $R^5$ is $CH_2$-phenyl substituted with 0–3 $R^{16}$.

6. The compound according to claim 5, wherein:

$R^3$ is selected from a carbocyclic residue substituted with 0–3 $R^{15}$, wherein the carbocyclic residue is selected from phenyl and $C_{3-6}$ cycloalkyl; and a heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, isoindolyl, piperidinyl, pyrrazolyl, 1,2,4-triazolyl, 1,2,3-triazolyl, tetrazolyl, thiazolyl, oxazolyl, pyrazinyl, and pyrimidinyl.

7. The compound according to claim 6, wherein:

$R^{15}$, at each occurrence, is selected from $C_{1-8}$ alkyl, $(CH_2)_vC_{3-6}$ cycloalkyl, $CF_3$, Cl, Br, I, F, $(CH_2)_r$ $NR^{15a}R^{15a'}$, $NO_2$, CN, OH, $(CH_2)_rOR^{15d}$, $(CH_2)_rC(O)$ $R^{15b}$, $(CH_2)_rC(O)NR^{15a}R^{15a'}$, $(CH_2)_rNR^{15f}C(O)R^{15b}$, $(CH_2)_rS(O)_pR^{15b}$, $(CH_2)_rS(O)_2NR^{15a}R^{15a'}$, $(CH_2)_r$ $NR^{15f}S(O)_2R^{15b}$, $(CH_2)_r$phenyl substituted with 0–3 $R^{15e}$, and a $(CH_2)_r$-5–6 membered heterocyclic system containing 1–4 heteroatoms selected from N, O, and S, substituted with 0–2 $R^{15e}$;

$R^{15a}$ and $R^{15a'}$, at each occurrence, are selected from H, $C_{1-6}$ alkyl, $C_{3-6}$ cycloalkyl, and $(CH_2)_r$phenyl substituted with 0–3 $R^{15e}$;

$R^{15b}$, at each occurrence, is selected from H, $C_{1-6}$ alkyl, $C_{3-6}$ cycloalkyl, and $(CH_2)_r$phenyl substituted with 0–3 $R^{15e}$;

$R^{15d}$, at each occurrence, is selected from $C_{1-6}$ alkyl and phenyl;

$R^{15e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{15f}$, at each occurrence, is selected from H, and $C_{1-5}$ alkyl.

8. The compound according to claim 7, wherein E is $-CR^7R^8-$.

9. The compound according to claim 8, wherein:

Z is selected from $C(O)NR^2R^3$, $C(=NR^1)NR^2R^3$, $C(=CHCN)NR^2R^3$, $C(=CHNO_2)NR^2R^3$, and $C(=C(CN)_2)NR^2R^3$.

10. The compound according to claim 9, wherein:

$R^6$ is H; and when K is $CHR^5$, either:
1) M is absent, or
2) Z is other than $C(O)NR^2R^3$.

11. The compound according to claim 10, wherein E is $-CH_2-$.

12. The compound according to claim 10, wherein:

Y is selected from:

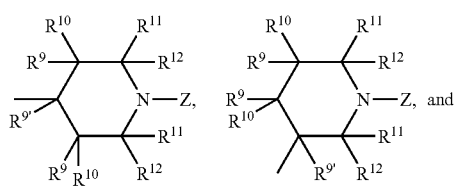

-continued

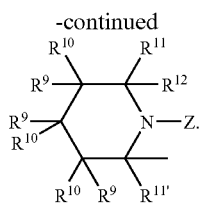

13. The compound according to claim 12, wherein:
Y is selected from:

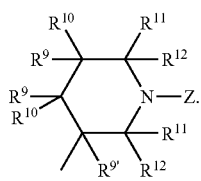

14. The compound according to claim 10, wherein:
$R^{16}$, at each occurrence, is selected from $C_{1-8}$ alkyl, $(CH_2)_rC_{3-6}$ cycloalkyl, $CF_3$, Cl, Br, I, F, $(CH_2)_r$NR$^{16a}$R$^{16a'}$, CN, OH, OCF$_3$, $(CH_2)_r$OR$^{16d}$, $(CH_2)_r$C(O)R$^{16b}$;

$R^{16a}$ and $R^{16a'}$, at each occurrence, are selected from H, $C_{1-6}$ alkyl, and $C_{3-6}$ cycloalkyl;

$R^{16b}$, at each occurrence, is selected from H, $C_{1-6}$ alkyl, $C_{3-6}$ cycloalkyl, and $(CH_2)_r$phenyl substituted with 0–3 $R^{16e}$;

$R^{16d}$, at each occurrence, is selected from $C_{1-6}$ alkyl and phenyl.

15. The compound according to claim 14, wherein $R^{16}$ is selected from F, Cl, Br, OCF$_3$, and CF$_3$.

16. The compound according to claim 10, wherein:
$R^{15}$, at each occurrence, is selected from CN, C(O)R$^{15b}$, and a $(CH_2)_r$-5-6 membered heterocyclic system containing 1–4 heteroatoms selected from N, O, and S, substituted with 0–2 $R^{15e}$;

$R^{15b}$, at each occurrence, is selected from H, $C_{1-6}$ alkyl, $C_{3-6}$ cycloalkyl, and $(CH_2)_r$phenyl substituted with 0–3 $R^{15e}$; and $R^{15e}$, at each occurrence, is selected from $C_{1-6}$ alkyl, Cl, F, Br, I, CN, NO$_2$, $(CF_2)_r$CF$_3$, OH, and $(CH_2)_r$OC$_{1-5}$ alkyl.

17. The compound according to claim 16, wherein:
$R^{15}$, at each occurrence, is selected from CN, C(O)R$^{15b}$, and a $(CH_2)_r$-5-6 membered heterocyclic system containing 1–4 heteroatoms selected from N, O, and S, substituted with 0–2 $R^{15e}$;

$R^{15b}$, at each occurrence, is selected from $C_{1-6}$ alkyl, $C_{3-6}$ cycloalkyl, and $(CH_2)_r$phenyl substituted with 0–3 $R^{15e}$; and $R^{15e}$, at each occurrence, is selected from $C_{1-6}$ alkyl, Cl, F, Br, I, CN, NO$_2$, $(CF_2)_r$CF$_3$, OH, and $(CH_2)_r$OC$_{1-5}$ alkyl.

18. The compound according to claim 10, wherein:
J and Q are CH$_2$; and
M is absent or CH$_2$.

19. The compound according to claim 14, wherein:
E is —CH$_2$—; and
Y is

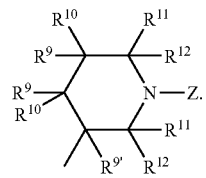

20. The compound according to claim 16, wherein:
E is —CH$_2$—; and
Y is

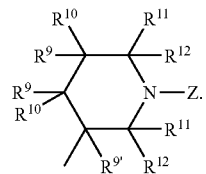

21. The compound according to claim 18, wherein:
Y is:

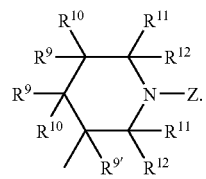

22. The compound according to claim 21, wherein K is CH$_2$.

23. The compound according to claim 1, wherein:
Z is selected from C(=NR$^1$)NR$^2$R$^3$ and C(=C(CN)$_2$)NR$^2$R$^3$.

24. The compound according to claim 2, wherein:
Z is selected from C(=NR$^1$)NR$^2$R$^3$ and C(=C(CN)$_2$)NR$^2$R$^3$.

25. The compound according to claim 4, wherein:
Z is selected from C(=NR$^1$)NR$^2$R$^3$ and C(=C(CN)$_2$)NR$^2$R$^3$.

26. The compound according to claim 6, wherein:
Z is selected from C(=NR$^1$)NR$^2$R$^3$ and C(=C(CN)$_2$)NR$^2$R$^3$.

27. The compound according to claim 12, wherein:
Z is selected from C(=NR$^1$)NR$^2$R$^3$ and C(=C(CN)$_2$)NR$^2$R$^3$.

28. The compound according to claim 21, wherein:
Z is selected from C(=NCN)NR$^2$R$^3$ and C(=C(CN)$_2$)NR$^2$R$^3$.

29. The compound according to claim 22, wherein:
Z is selected from C(=NCN)NHR$^3$ and C(=C(CN)$_2$)NHR$^3$; and R$^{16}$ is selected from F, Cl, Br, OCF$_3$, and CF$_3$.

30. The compound according to claim 13, wherein:
Z is selected from C(=NCN)NR$^2$R$^3$ and C(=C(CN)$_2$)NR$^2$R$^3$.

31. The compound according to claim 10, wherein R$^3$ is phenyl substituted with 0–3 R$^{15}$.

32. The compound according to claim 13, wherein $R^3$ is phenyl substituted with 0–3 $R^{15}$.

33. The compound according to claim 16, wherein $R^3$ is phenyl substituted with 0–3 $R^{15}$.

34. The compound according to claim 13, wherein:
$R^3$ is phenyl substituted with 0–3 $R^{15}$;
Z is selected from $C(=NR^1)NR^2R^3$ and $C(=C(CN)_2)NR^2R^3$;
J and Q are $CH_2$; and
M is absent or $CH_2$.

35. The compound according to claim 1, wherein the compound of formula I is selected from:
- (+/−)-N-phenyl-3-[[4-(phenylmethyl)-1-piperidinyl]methyl]-1-piperidinecarboxamide,
- (+/−)-N-(3-methoxyphenyl)-3-[[4-(phenylmethyl)-1-piperidinyl]methyl]-1-piperidinecarboxamide,
- (+/−)-N-(3-carboethoxyphenyl)-3-[[4-(phenylmethyl)-1-piperidinyl]methyl]-1-piperidinecarboxamide,
- (+/−)-N-(3-cyanophenyl)-3-[[4-(phenylmethyl)-1-piperidinyl]methyl]-1-piperidinecarboxamide,
- (+/−)-N-(1-adamantyl)-3-[[4-(phenylmethyl)-1-piperidinyl]methyl]-1-piperidinecarboxamide,
- N-phenyl-4-[[4-(phenylmethyl)-1-piperidinyl]methyl]-1-piperidinecarboxamide,
- N-(3-cyanophenyl)-4-[[4-(phenylmethyl)-1-piperidinyl]methyl]-1-piperidinecarboxamide,
- N-(1-adamantyl)-4-[[4-(phenylmethyl)-1-piperidinyl]methyl]-1-piperidinecarboxamide,
- N-(3-methoxyphenyl)-4-[[4-(phenylmethyl)-1-piperidinyl]methyl]-1-piperidinecarboxamide,
- N-(3-carboethoxyphenyl)-4-[[4-(phenylmethyl)-1-piperidinyl]methyl]-1-piperidinecarboxamide,
- 1-benzoyl-4-[[4-(phenylmethyl)-1-piperidinyl]methyl]piperidine,
- 1-phenylacetyl-4-[[4-(phenylmethyl)-1-piperidinyl]methyl]piperidine,
- 1-(3,4-dimethoxybenzoyl)-4-[[4-(phenylmethyl)-1-piperidinyl]methyl]piperidine,
- 1-(3,5-dichlorobenzoyl)-4-[[4-(phenylmethyl)-1-piperidinyl]methyl]piperidine,
- 1-(3,5-difluorobenzoyl)-4-[[4-(phenylmethyl)-1-piperidinyl]methyl]piperidine,
- 1-(3,5-dimethoxybenzoyl)-4-[[4-(phenylmethyl)-1-piperidinyl]methyl]piperidine,
- 1-(3,4-methylenedioxybenzoyl)-4-[[4-(phenylmethyl)-1-piperidinyl]methyl]piperidine,
- 1-(2-thiophenesulfonyl)-4-[[(4-(phenylmethyl)-1-piperidinyl]methyl]-piperidinecarboxamide,
- 1-(3-methoxyphenylacetyl)-4-[[4-(phenylmethyl)-1-piperidinyl]methyl]piperidine,
- 1-(4-methoxyphenylacetyl)-4-[[4-(phenylmethyl)-1-piperidinyl]methyl]piperidine,
- (+/−)-N-phenyl-3-[[4-[(4-fluorophenyl)methyl]-1-piperidinyl]methyl]-1-piperidinecarboxamide,
- (+/−)-N-(3-cyanophenyl)-3-[[4-[(4-fluorophenyl)methyl]-1-piperidinyl]methyl]-1-piperidinecarboxamide,
- (+/−)-N-(1-adamantylphenyl)-3-[[4-[(4-fluorophenyl)methyl]-1-piperidinyl]methyl]-1-piperidinecarboxamide,
- (+/−)-N-(3-carboethoxyphenyl)-3-[[4-[(4-fluorophenyl)methyl]-1-piperidinyl]methyl]-1-piperidinecarboxamide,
- (+/−)-N-(4-fluorophenyl)-3-[[4-[(4-fluorophenyl)methyl]-1-piperidinyl]methyl]-1-piperidinecarboxamide,
- (+/−)-N-(3-methoxyphenyl)-3-[[4-[(4-fluorophenyl)methyl]-1-piperidinyl]methyl]-1-piperidinecarboxamide,
- (+/−)-N-(3-cyanophenyl)-3-[[4-[(4-fluorophenyl)methyl]-1-piperidinyl]ethyl]-1-piperidinecarboxamide,
- (+/−)-N-(3-carboethoxyphenyl)-3-[[4-[(4-fluorophenyl)methyl]-1-piperidinyl]ethyl]-1-piperidinecarboxamide,
- (+/−)-N-(4-carboethoxyphenyl)-3-[[4-[(4-fluorophenyl)methyl]-1-piperidinyl]ethyl]-1-piperidinecarboxamide,
- (+/−)-N-(4-fluorophenyl)-3-[[4-[(4-fluorophenyl)methyl]-1-piperidinyl]ethyl]-1-piperidinecarboxamide,
- (+/−)-N-(1-adamantylphenyl)-3-[[4-[(4-fluorophenyl)methyl]-1-piperidinyl]ethyl]-1-piperidinecarboxamide,
- (+/−)-N-phenyl-3-[[4-[(4-fluorophenyl)methyl]-1-piperidinyl]ethyl]-1-piperidinecarboxamide,
- (+/−)-N-(3-methoxyphenyl)-3-[[4-[(4-fluorophenyl)methyl]-1-piperidinyl]ethyl]-1-piperidinecarboxamide,
- (+/−)-1-phenylsulfonyl-3-[[4-[(4-fluorophenyl)methyl]-1-piperidinyl]ethyl]-piperidinecarboxamide,
- (+/−)-1-benzoyl-3-[[4-[(4-fluorophenyl)methyl]-1-piperidinyl]ethyl]-1-piperidinecarboxamide,
- (+/−)-1-benzyloxycarbonyl-3-[[4-[(4-fluorophenyl)methyl]-1-piperidinyl]ethyl]-1-piperidinecarboxamide,
- (+/−)-N-(4-fluorophenyl)-3-[[4-[(4-fluorophenyl)methyl]-1-piperidinyl]methyl]-1-piperidinecarboxamide,
- (+/−)-N-phenyl-2-[[4-[(4-fluorophenyl)methyl]-1-piperidinyl]methyl]-1-pyrrolidinecarboxamide,
- (+/−)-N-(3-cyanophenyl)-2-[[4-[(4-fluorophenyl)methyl]-1-piperidinyl]methyl]-1-pyrrolidinecarboxamide,
- (+/−)-N-(3-methoxyphenyl)-2-[[4-[(4-fluorophenyl)methyl]-1-piperidinyl]methyl]-1-pyrrolidinecarboxamide,
- (+/−)-N-(4-fluorophenyl)-2-[[4-[(4-fluorophenyl)methyl]-1-piperidinyl]methyl]-1-piperidinecarboxamide,
- (+/−)-N-(3-carboethoxyphenyl)-2-[[4-[(4-fluorophenyl)methyl]-1-piperidinyl]methyl]-1-pyrrolidinecarboxamide,
- (+/−)-N-(4-carboethoxyphenyl)-2-[[4-[(4-fluorophenyl)methyl]-1-piperidinyl]methyl]-1-pyrrolidinecarboxamide,
- (+/−)-N-(1-adamantylphenyl)-2-[[4-[(4-fluorophenyl)methyl]-1-piperidinyl]methyl]-1-pyrrolidinecarboxamide,
- (+/−)-N-phenyl-2-[[4-[(4-fluorophenyl)methyl]-1-piperidinyl]ethyl]-1-piperidinecarboxamide,
- (+/−)-N-(3-cyanophenyl)-2-[[4-[(4-fluorophenyl)methyl]-1-piperidinyl]ethyl]-1-piperidinecarboxamide,
- (+/−)-N-(3-methoxyphenyl)-2-[[4-[(4-fluorophenyl)methyl]-1-piperidinyl]ethyl]-1-piperidinecarboxamide,
- (+/−)-N-(4-fluorophenyl)-2-[[4-[(4-fluorophenyl)methyl]-1-piperidinyl]ethyl]-1-piperidinecarboxamide,
- (+/−)-N-(3-carboethoxyphenyl)-2-[[4-[(4-fluorophenyl)methyl]-1-piperidinyl]ethyl]-1-piperidinecarboxamide,
- (+/−)-N-(4-carboethoxyphenyl)-2-[[4-[(4-fluorophenyl)methyl]-1-piperidinyl]ethyl]-1-piperidinecarboxamide,
- (+/−)-N-(1-adamantylphenyl)-2-[[4-[(4-fluorophenyl)methyl]-1-piperidinyl]ethyl]-1-piperidinecarboxamide,
- (+/−)-N-(3-cyanophenyl)-3-[[4-[(4-fluorophenyl)methyl]-1-piperidinyl]methyl]-3-hydroxy-1-piperidinecarboxamide,
- (+/−)-N-(3-carboethoxyphenyl)-3-[[4-[(4-fluorophenyl)methyl]-1-piperidinyl]methyl]-3-hydroxy-1-piperidinecarboxamide,
- (+/−)-N-(4-carboethoxyphenyl)-3-[[4-[(4-fluorophenyl)methyl]-1-piperidinyl]methyl]-3-hydroxy-1-piperidinecarboxamide,
- (+/−)-N-(4-fluorophenyl)-3-[[4-[(4-fluorophenyl)methyl]-1-piperidinyl]methyl]-3-hydroxy-1-piperidinecarboxamide,
- (+/−)-N-phenyl-3-[[4-[(4-fluorophenyl)methyl]-1-piperidinyl]methyl]-3-hydroxy-1-piperidinecarboxamide, (+/−)-N-(3-methoxyphenyl)-3-[[4-[(4-fluorophenyl)methyl]-1-piperidinyl]methyl]-3-hydroxy-1-piperidinecarboxamide, (+/−)-N-(3-cyanophenyl)-3-[[4-[(4-fluorophenyl)methyl]-1-piperidinyl]methyl]-3-phenylmethyl-1-piperidine-carboxamide, (+/−)-N-(4-fluorophenyl)-3-[[4-[(4-fluorophenyl)methyl]-1-piperidinyl]methyl]-3-phenylmethyl-1-piperidine-carboxamide, (+/−)-N-phenyl-3-[[4-[(4-fluorophenyl)methyl]-1-piperidinyl]methyl]-3-phenylmethyl-1-piperidinecarboxamide, (+/−)-N-(3-methoxyphenyl)-3-[[4-[(4-fluorophenyl)methyl]-1-piperidinyl]methyl]-3-phenylmethyl-1-piperidine-carboxamide, (+/−)-(cis)-N-(3-cyanophenyl)-3-[[4-[(4-fluorophenyl)methyl]-1-piperidinyl]methyl]-2-phenylmethyl-1-piperidine-carboxamide, (+/−)-(cis)-N-(3-carboethoxyphenyl)-3-[[4-[(4-fluorophenyl)methyl]-1-piperidinyl]methyl]-2-phenylmethyl-1-piperidinecarboxamide, (+/−)-(cis)-N-(4-carboethoxyphenyl)-3-[[4-[(4-fluorophenyl)methyl]-1-piperidinyl]methyl]-2-phenylmethyl-1-piperidinecarboxamide, (+/−)-(cis)-N-(4-fluorophenyl)-3-[[4-[(4-fluorophenyl)methyl]-1-piperidinyl]methyl]-2-phenylmethyl-1-piperidine carboxamide, (+/−)-(cis)-N-phenyl-3-[[4-[(4-fluorophenyl)methyl]-1-piperidinyl]methyl]-2-phenylmethyl-1-piperidine-carboxamide, (+/−)-(cis)-N-(3-methoxyphenyl)-3-[[4-[(4-fluorophenyl)methyl]-1-piperidinyl]methyl]-2-phenylmethyl-1-piperidinecarboxamide, (+/−)-(trans)-N-(3-cyanophenyl)-3-[[4-[(4-fluorophenyl)methyl]-1-piperidinyl]methyl]-2-phenylmethyl-1-piperidinecarboxamide, (+/−)-(trans)-N-(3-carboethoxyphenyl)-3-[[4-[(4-fluorophenyl)methyl]-1-piperidinyl]methyl]-2-phenylmethyl-1-piperidinecarboxamide, (+/−)-(trans)-N-(4-carboethoxyphenyl)-3-[[4-[(4-fluorophenyl)methyl]-1-piperidinyl]methyl]-2-phenylmethyl-1-piperidinecarboxamide, (+/−)-(trans)-N-(4-fluorophenyl)-3-[[4-[(4-fluorophenyl)methyl]-1-piperidinyl]methyl]-2-phenylmethyl-1-piperidinecarboxamide, (+/−)-(trans)-N-phenyl-3-[[4-[(4-fluorophenyl)methyl]-1-piperidinyl]methyl]-2-phenylmethyl-1-piperidine carboxamide, (+/−)-(trans)-N-(3-methoxyphenyl)-3-[[4-[(4-fluorophenyl)methyl]-1-piperidinyl]methyl]-2-phenylmethyl-1-piperidinecarboxamide, (+/−)-(trans)-N-(3-carboethoxyphenyl)-3-[[4-(4-flourophenyl) methyl]-1-piperidinyl]methyl]-2-phenylmethyl-1-piperidinecarboxamide, 3-{[3-(4-fluorobenzyl)-1-pyrrolidinyl]methyl}-N-phenyl-1-piperidinecarboxamide, N-(3-cyanophenyl)-3-{[3-(4-fluorobenzyl)-1-pyrrolidinyl]methyl}-1-piperidinecarboxamide, N-(3-acetylphenyl)-3-{[3-(4-fluorobenzyl)-1-pyrrolidinyl]methyl}-1-piperidinecarboxamide, 3-{[(3S)-3-(4-fluorobenzyl)piperidinyl]methyl}-N-phenyl-1-piperidinecarboxamide, N-(3-cyanophenyl)-3-{[(3S)-3-(4-fluorobenzyl)piperidinyl]methyl}-1-piperidinecarboxamide, and N-(3-acetylphenyl)-3-{[(3S)-3-(4-fluorobenzyl)piperidinyl]methyl}-1-piperidinecarboxamide.

36. A pharmaceutical composition comprising a pharmaceutically acceptable carrier and a therapeutically effective amount of a compound according to claim 1.

37. A pharmaceutical composition comprising a pharmaceutically acceptable carrier and a therapeutically effective amount of a compound according to claim 10.

38. A method of treating disorders comprising administering to a patient in need thereof a therapeutically effective amount of a compound according to claim 1, wherein the disorder is selected from asthma, allergic rhinitis, atopic dermatitis, inflammatory bowel diseases, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, HIV infection, cystic fibrosis, Churg-Strauss syndrome, lymphoma, Hodgkin's disease, and colonic carcinoma.

39. The method according to claim 38, wherein the disorder is selected from asthma, allergic rhinitis, atopic dermatitis, and inflammatory bowel diseases.

40. The method according to claim 39, wherein the disorder is asthma.

41. A method of treating disorders comprising administering to a patient in need thereof a therapeutically effective amount of a compound according to claim 10, wherein the disorder is selected from asthma, allergic rhinitis, atopic dermatitis, inflammatory bowel diseases, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, HIV infection, cystic fibrosis, Churg-Strauss syndrome, lymphoma, Hodgkin's disease, and colonic carcinoma.

42. The method according to claim 41, wherein the disorder is selected from asthma, allergic rhinitis, atopic dermatitis, and inflammatory bowel diseases.

43. The method according to claim 42, wherein the disorder is asthma.

* * * * *

UNITED STATES PATENT AND TRADEMARK OFFICE
CERTIFICATE OF CORRECTION

PATENT NO. : 7,312,222 B2  Page 1 of 1
APPLICATION NO. : 10/809772
DATED : December 25, 2007
INVENTOR(S) : Soo S. Ko et al.

It is certified that error appears in the above-identified patent and that said Letters Patent is hereby corrected as shown below:

Column 115, Claim 17, line 52, please delete "16" and insert -- 14 --.

Signed and Sealed this

Ninth Day of December, 2008

JON W. DUDAS
*Director of the United States Patent and Trademark Office*